(12) United States Patent
Chatterjee et al.

(10) Patent No.: US 11,267,899 B2
(45) Date of Patent: Mar. 8, 2022

(54) AFUCOSYLATED PROTEIN, CELL EXPRESSING SAID PROTEIN AND ASSOCIATED METHODS

(71) Applicant: Zumutor Biologies, Inc., Woburn, MA (US)

(72) Inventors: Sohang Chatterjee, Bangalore (IN); Kavitha Iyer Rodrigues, Bangalore (IN); Maloy Ghosh, Bangalore (IN); Sunit Maity, Bangalore (IN); Divya Unnikrishnan, Bangalore (IN); Jahnabi Hazarika, Bangalore (IN); Yogendra Manjunath Bangalore Muniraju, Bangalore (IN); Sathyabalan Murugesan, Bangalore (IN); Pavithra Mukunda, Kundapur (IN); Bhargav Prasad, Chennai (IN); Veeresha Kamanagowda, Bangalore (IN); Sanghamitra Bhattacharjee, Bangalore (IN); Pravin Kumar Dakshinamurthy, Chennai (IN); Vivek Halan, Aravenu (IN); Sankaranarayanan Srinivasan, Bangalore (IN); Anuradha Hora, Sitapur (IN); Bairavabalakumar Natarajan, Chennai (IN); Karthika Nair, Bangalore (IN); Aswini Thanigaivel, Chennai (IN); Amol Maliwalave, Bangalore (IN); Bharath Ravindra Shenoy, Bangalore (IN); Sahana Bhima Rao, Bangalore (IN); Subhra Prakash Chakrabarty, Bangalore (IN); Ashvini Kumar Dubey, Bangalore (IN); Amir Khan, Aligarh (IN); Ankurina Sharma, Bangalore (IN)

(73) Assignee: Zumutor Biologics Inc., San Francisco, CA (US)

(*) Notice: Subject to any disclaimer, the term of this patent is extended or adjusted under 35 U.S.C. 154(b) by 736 days.

(21) Appl. No.: 15/573,702

(22) PCT Filed: May 13, 2016

(86) PCT No.: PCT/IB2016/052774
§ 371 (c)(1),
(2) Date: Nov. 13, 2017

(87) PCT Pub. No.: WO2016/181357
PCT Pub. Date: Nov. 17, 2016

(65) Prior Publication Data
US 2018/0171028 A1 Jun. 21, 2018

(30) Foreign Application Priority Data
May 13, 2015 (IN) .............................. 194/CHE/2015

(51) Int. Cl.
| | |
|---|---|
| C12N 5/00 | (2006.01) |
| C07K 16/32 | (2006.01) |
| C12N 15/113 | (2010.01) |
| C07K 16/06 | (2006.01) |
| C12N 9/22 | (2006.01) |
| C12N 15/90 | (2006.01) |

(52) U.S. Cl.
CPC ............ *C07K 16/32* (2013.01); *C07K 16/065* (2013.01); *C12N 9/22* (2013.01); *C12N 15/1137* (2013.01); *C12N 15/907* (2013.01); *C07K 2317/14* (2013.01); *C07K 2317/41* (2013.01); *C07K 2317/73* (2013.01); *C07K 2317/732* (2013.01); *C07K 2317/76* (2013.01); *C12N 2310/10* (2013.01); *C12N 2310/20* (2017.05); *C12N 2800/80* (2013.01); *C12Y 204/01068* (2013.01)

(58) Field of Classification Search
CPC .. C07K 16/32; C07K 16/065; C07K 2317/14; C07K 2317/41; C07K 2317/73; C07K 2317/732; C07K 2317/76; C12N 9/22; C12N 15/1137; C12N 15/907; C12N 2310/20; C12N 2310/10; C12N 2800/80; C12Y 204/01068
See application file for complete search history.

(56) References Cited

U.S. PATENT DOCUMENTS

2019/0112358 A1* 4/2019 Prasad ................. C12N 15/102

FOREIGN PATENT DOCUMENTS

| EP | 1705251 | 9/2006 |
|---|---|---|
| WO | WO2015/010114 | 1/2015 |

(Continued)

OTHER PUBLICATIONS

Suzuki et al. (Clin Cancer Res 2007: vol. 13, No. 6, pp. 1875-1882, published Mar. 15, 2007). (Year: 2007).*

(Continued)

*Primary Examiner* — Catherine S Hibbert
(74) *Attorney, Agent, or Firm* — Fish & Richardson P.C.

(57) ABSTRACT

The present disclosure relates to methods of obtaining cell with disrupted fucosylation and obtaining afucosylated protein. The present disclosure employs the Clustered Regularly Interspaced Short Palindromic Repeats (CRISPR) technology in a protein producing cell line to produce afucosylated protein. The resulting protein, specifically the resulting monoclonal antibody is completely afucosylated and reveals higher degree of antibody dependent cellular cytotoxicity.

9 Claims, 21 Drawing Sheets
Specification includes a Sequence Listing.

(56) References Cited

FOREIGN PATENT DOCUMENTS

WO     WO2016/075662     5/2016
WO     WO2016/181357     11/2016

OTHER PUBLICATIONS

Carlotta Ronda et al., "Accelerating genome editing in CHO cells using CRISPR Cas9 and CRISPy, a web-based target finding tool", Biotechnology and Bioengineering, vol. 111, No. 8, Aug. 22, 2014, pp. 1604-1616.
International Search Report and Written Opinion dated Sep. 28, 2016 for Int'l. Appln. No. PCT/IB2016/052774 (20 pgs.).
International Preliminary Report on Patentability dated Sep. 5, 2017 for Int'l. Appln. No. PCT/IB2016/052774 (28 pgs.).
Written Opinion dated Jun. 16, 2017 for Int'l. Appln. No. PCT/IB2016/052774 (14 pgs.).

* cited by examiner

Figure 1B

MRAWTGSWRWIMLILFAWGTLLFYIGGHLVRDNDHPDHSSRELSKILAKLERLKQQNEDLRRMAESLRIPEGPID
QGTATGRVRVLEEQLVKAKEQIENYKKQARNDLGKDHEILRRRIENGAKELWFFLQSELKKLKKLEGNELQRHAD
EILLDLGHHERSIMTDLYYLSQTDGAGEWREKEAKDLTELVQRRITYLQNPKDCSKARKLVCNINKGCGYGCQLH
HVVYCFMIAYGTQRTLILESQNWRYATGGWETVFRPVSETCTDRSGLSTGHWSGEVKDKNVQVVELPIVDSLHPR
PPYLPLAVPEDLADRLLRVHGDPAVWWVSQFVKYLIRPQPWLEREIEETTKKLGFKHPVIGVHVRRTDKVGTEAA
FHPIEEYMVHVEEHFQLLERRMKVDKKRVYLATDDPSLLKEAKTKYSNYEFISDNSISWSAGLHNRYTENSLRGV
ILDIHFLSQADFLVCTFSSQVCRVAYEIMQTLHPDASANFHSLDDIYYFGGQNAHNQIAVYPHQPRTKEEIPMEP
GDIIGVAGNHWNGYSKGVNRKLGKTGLYPSYKVREKIETVKYPTYPEAEK

Figure 2

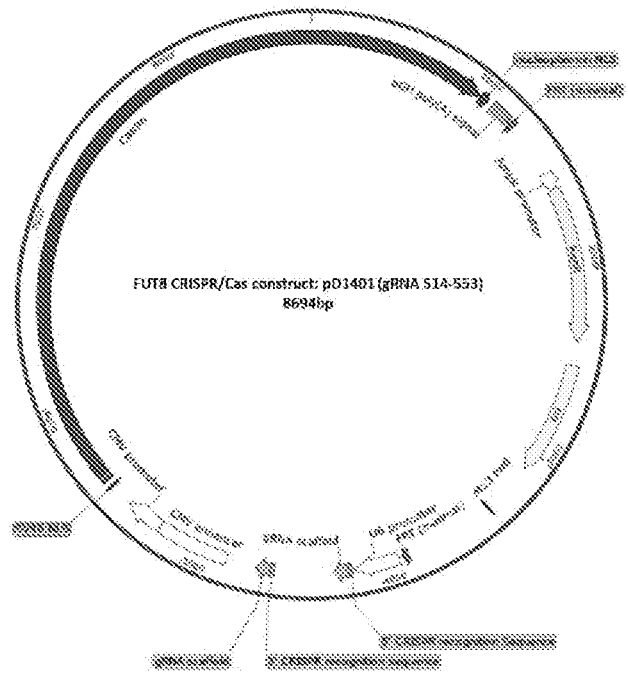

Figure 3A

CACCCAGCG▲ACACTCATCTTGGAATCTCAG<u>AATTGGCGCTATGCTACTGG</u>AGGATG
GTGGGT<u>CGCTTGTGAGTAGAACCTTA</u>GAGTCTTAACCGCGATACGATG▼CCTCCTAC

| Bright field image | Red fluorescence image | Overlay image |
| A | B | C |

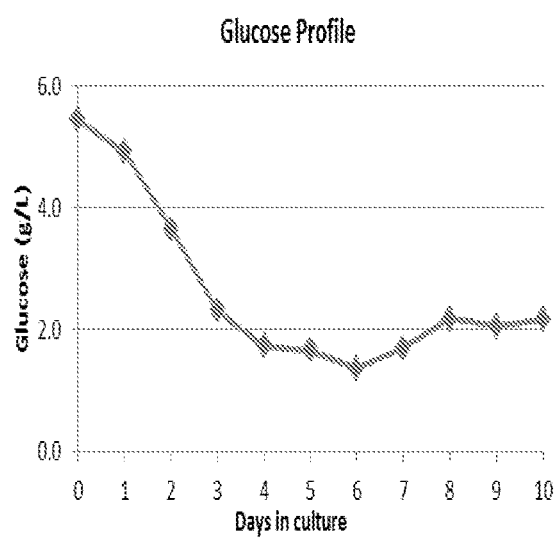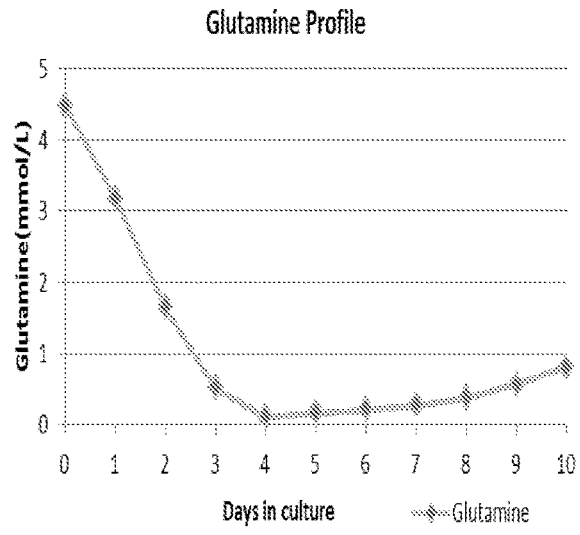
Figure 12A and 12B
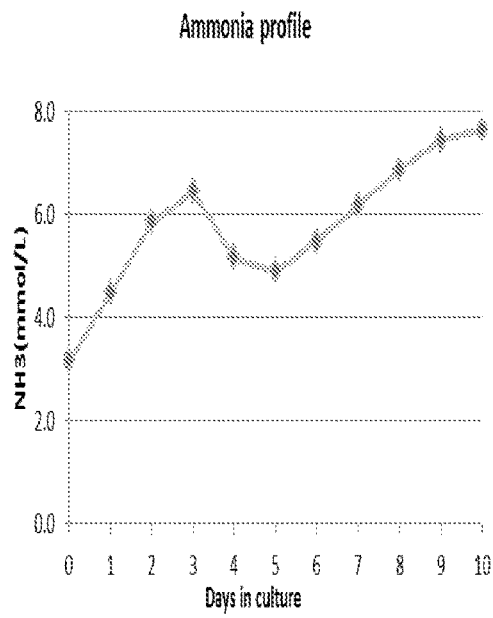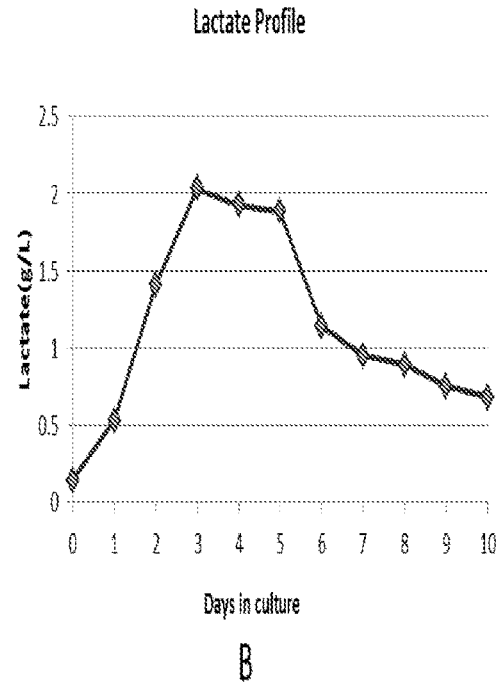
Figure 13A and 13B

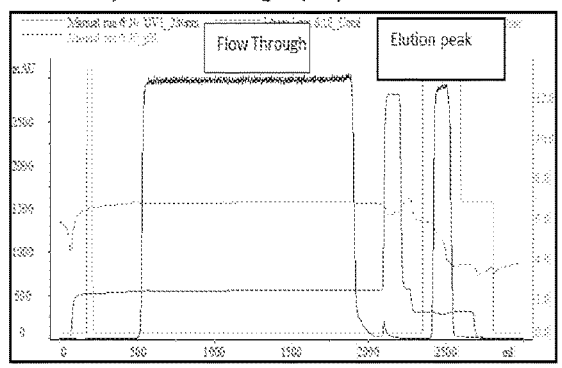
14A
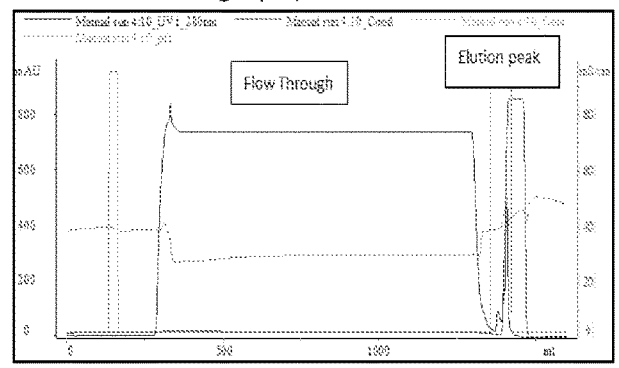
14B
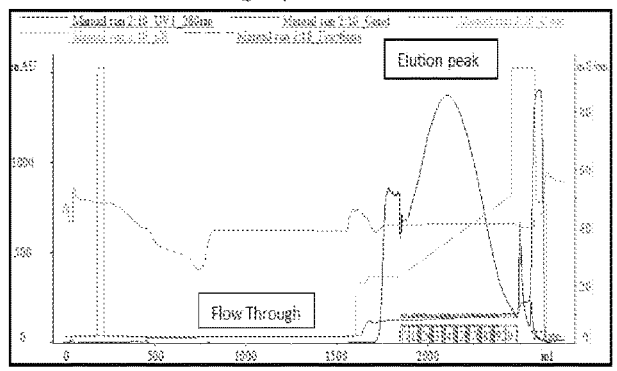
14C
Figure 14

Lane1: Trastuzumab
Lane2: Afucosylated antiHer2 antibody

SDS-PAGE

| 1 | 2 | 3 | 4 | 5 | Lane Details |
|---|---|---|---|---|---|
| | | | | | Lane 1: Trastuzumab (Intact) |
| | | | | | Lane 2: AFUCOSYLATED ANTI-HER2 ANTIBODY (Intact) |
| | | | | | Protein Standard Marker |
| | | | | | Lane 4: Trastuzumab (Reduced) |
| | | | | | Lane 5: AFUCOSYLATED ANTI-HER2 ANTIBODY (Reduced) |

Figure 16

Western Blot

| 1 | 2 | 3 | 4 | 5 | Lane Details |
|---|---|---|---|---|---|
| | | | | | Lane 1: Trastuzumab (Intact) |
| | | | | | Lane 2: AFUCOSYLATED ANTI-HER2 ANTIBODY (Intact) |
| | | | | | Protein Standard Marker |
| | | | | | Lane 4: Trastuzumab (Reduced) |
| | | | | | Lane 5: AFUCOSYLATED ANTI-HER2 ANTIBODY (Reduced) |

Figure 17

▨ Trastuzumab
▨ Afucosylated anti-HER2 antibody

AFUCOSYLATED PROTEIN, CELL EXPRESSING SAID PROTEIN AND ASSOCIATED METHODS

CROSS-REFERENCE TO RELATED APPLICATIONS

This application is a National Stage application under 35 U.S.C. § 371 of International Application No. PCT/IB2016/052774 having an International Filing Date of May 13, 2016, which claims the benefit of priority from Indian Application Serial No. 194/CHE/2015, having a filing date of May 13, 2015.

The disclosures of the prior applications are considered part of (and are incorporated by reference in) the disclosure of this application.

SEQUENCE LISTING

This application contains a Sequence Listing that has been submitted electronically as an ASCII text file named SEQ.txt. The ASCII text file, created on Feb. 10, 2020, is 45,066 bytes in size. The material in the ASCII text file is hereby incorporated by reference in its entirety.

TECHNICAL FIELD

The present disclosure pertains to the field of biotechnology, genetic engineering and immunology. Particularly, the present disclosure relates to developing cell lines where specific biological pathways are modified. Such modifications are in the enzymes of the cell, particularly in enzymes involved in glycosylation of proteins. The present disclosure develops protein expression systems wherein specific modification of glycan chain of the protein is achieved. The specific modification of the glycan chain produces afucosylated proteins, including antibodies. The present disclosure employs the Clustered Regularly Interspaced Short Palindromic Repeats (CRISPR) technology in a protein producing cell line, specifically an antibody producing cell line. The resulting monoclonal antibody is completely afucosylated and reveals higher degree of antibody dependent cellular cytotoxicity.

BACKGROUND AND PRIOR ART OF THE DISCLOSURE

Glycosylation in eukaryotes has been studied intensively for decades as the most common covalent post translational protein modification mechanism. About 1-2% of the human transcriptome (about 250-500 glycogenes) is predicted to translate proteins which are responsible for glycosylation (Campbell and Yarema 2005). Glycosylation of cellular proteins plays many key biological functions such as protein folding, stability, intracellular and inter-cellular trafficking, cell-cell interaction and cell matrix interaction.

There are four distinct groups of Glycoproteins: N-linked, O-linked, glycosaminoglycans, and glycosylphosphatidylinositol-anchored proteins. N-linked glycosylation occurs through the side chain amide nitrogen of asparagine residues, and takes place in the amino acid sequence of Asn-X-Ser/Thr, where X can be any amino acid except proline and aspartic acid (Helenius and Aebi 2004). O-linked glycosylation uses the oxygen atom in the side chain of serine or threonine residues.

Fucose (6-deoxy-L-galactose) is a monosaccharide that is present in many glycoproteins and glycolipids present in vertebrates, invertebrates, plants, and bacteria. Fucosylation is the process of transferring a fucose residue to various proteins and oligosaccharides. Fucosylation is regulated by several molecules, including fucosyltransferases, guanosine diphosphate (GDP)-fucose synthetic enzymes, and GDP-fucose transporter(s). A large number of fucosylated glycoproteins are secretory proteins or membrane proteins on the cell surface.

The most prominent change in oncology drug development in the last 20 years has been the shift from classic cytotoxics to drugs that affect signaling pathways implicated in cancer, known as "Monoclonal Antibodies" or mAbs. Improvement of monoclonal antibody therapeutics through technologies described here will pave the way for better clinical outcome for patients.

Human IgG1 antibody is a highly fucosylated glycoprotein. Two N-linked biantennary oligosaccharides consisting of core hepta-saccharide with variable addition of fucose, galactose, bisecting N-acetylglucosamine and sialic acid are present at Asn-297 of IgG1. Antibody glycosylation leads to unique biological functions known as "effector functions"—Antibody Dependent Cellular Cytotoxicity (ADCC) and Complement Dependent Cytotoxicity (CDC).

The effector function of IgG molecule is defined by the interaction of antibody Fc region with leukocyte receptors, known as FcγRs, or interactions with complement components. The composition of the oligosaccharide structure is critically important for effector function through FcγR binding (Shields et al. 2002; Shinkawa et al. 2003; Niwa et al. 2004; Niwa, Shoji-Hosaka, et al. 2004; Yamane-Ohnuki et al. 2004). Crystal structure analysis of human IgG1 has revealed intricate interaction of the oligosaccharide chains with the CH2 domain (Harris et al. 1998; Radaev et al. 2001).

The efficiency of the ADCC mechanism is considerably dependent on the level of antibody fucosylation. The lower the fucosylation, the higher is the rate of ADCC. Therefore, loss of fucosylation has significant biological consequences. The loss could be due to non-functional fucosyltransferase enzymes, resulting in non-fucosylation of cellular proteins. The absence of fucose from the primary N-acetylglucosamine results in the IgG1 antibody having increased binding affinity for the FcγRIIIα receptor, with consequent increase of 50-100 times higher efficacy of ADCC. Improvement of ADCC with non-fucosylated IgG is directly proportional to the increased affinity for FcγRIIIα, which allows the non-fucosylated IgG Fc to overcome the competition from high concentrations of fucosylated IgG in normal serum. Plausible rationale for the increased affinity of non-fucosylated IgG Fc for FcγRIIIα may be the reduction or absence of steric inhibition at the receptor-ligand interface (Harris, 1998; Radaev, 2001).

In mammalian expression systems, GDP-fucose, an essential substrate of fucosylation, is synthesized in the cytoplasm through de novo and salvage pathways. In the de novo pathway of fucosylation, GDP-fucose is synthesized through conversion of GDP-mannose to GDP-4-keto-6-deoxy-mannose, catalyzed by the enzyme GDP-mannose 4,6-dehydratase (GMD). This GDP-Fucose is then transported inside the golgi and used as a substrate for protein fucosylation by the enzyme α1-6 fucosyltransferase (encoded by FUT8 gene).

Non-fucosylated forms of therapeutic antibodies developed in mammalian platforms, where fucose biosynthesis is impaired, may have clinical advantage over the fucosylated forms due to the enhanced efficiency of ADCC towards target tumor cells.

Historically, gene knock out systems completely depended on Homologous recombination (HR) mediated targeted mutation, deletion and/or insertion. The HR system, although very specific, is highly inefficient, as thousands of clones need to be screened to find one mutated clone. Moreover, deleting allelic variations would take even further time and much larger screening.

Zinc Finger Nuclease (ZFN) is one of the most frequently used techniques for gene disruption. It requires three bases at the DNA level for each zinc finger tandem array. Moreover, target site overlap and cross-talk between individual fingers in a zinc-finger array considerably complicate the production of sequence-specific ZFNs. Additionally, major drawback of ZFNs includes elaborate and time-consuming experimental selection process to identify the ZFN motifs for specific DNA sequence recognition.

There are methods in the prior art for disruption of Fut8 genomic locus. However, none of the methods target the specific location on the FUT8 genomic locus by the CRISPR technology to produce afucosylated proteins from cells that encode for such proteins.

The present disclosure overcomes the disadvantages or limitations associated with methods of the prior art by using the CRISPR technology to target a specific location on the FUT8 genomic locus, which results in complete disruption of the gene and related function, providing a cell that produces non-fucosylated proteins.

STATEMENT OF THE DISCLOSURE

Accordingly, the present disclosure relates to a cell comprising a gene encoding antibody involved in Antibody-dependent cell-mediated cytotoxicity (ADCC) and vector comprising a CRISPR DNA binding domain selected from the group consisting of SEQ ID No. 11 and SEQ ID No. 13 or combination thereof; a method of obtaining a fucose knockout cell, said method comprising a step of transfecting a cell with a CRISPR nuclease construct to obtain a fucose knockout cell; a method of obtaining afucosylated protein, said method comprising step of obtaining a protein expressed by the fucose knockout cell obtained by the method mentioned above; an afucosylated protein; a composition comprising the protein as mentioned above, optionally along with pharmaceutically acceptable excipient; afucosylated protein as mentioned above for use in managing disorder selected from the group consisting of cancer, autoimmune disorder, viral infectious disease, bacterial infectious disease, inflammation and tumour or combinations thereof; and a method of managing disorder selected from the group consisting of cancer, autoimmune disorder, viral infectious disease, bacterial infectious disease, inflammation and tumour or combinations thereof, said method comprising step of administering the afucosylated protein as mentioned above, to a subject in need thereof

BRIEF DESCRIPTION OF THE ACCOMPANYING FIGURES

The features of the present disclosure will become fully apparent from the following description taken in conjunction with the accompanying drawings. With the understanding that the drawings depict only several embodiments in accordance with the disclosure and are therefore, not to be considered limiting of its scope, the disclosure will be described with additional specificity and detail through use of the accompanying drawings:

FIG. 1B depicts Fut 8 exon7 genomic locus, respective amino acid sequence and position of important structural motifs and CRISPR target locations. The nucleotide sequence is set forth in SEQ ID No.29 (top strand) and SEQ ID No.42 (bottom strand), and the amino acid sequence is set forth in SEQ ID No.5.

FIG. 2 depicts CHO-S genome analysis of FUT8 gene. Each exon is represented with arrow marks. The sequence is set forth in SEQ ID No.30.

FIG. 3A depicts FUT8 CRISPR/Cas construct pD1401 (gRNA 514-553), targeting Exon 7 of FUT8 gene.

Figures 3B, 4:
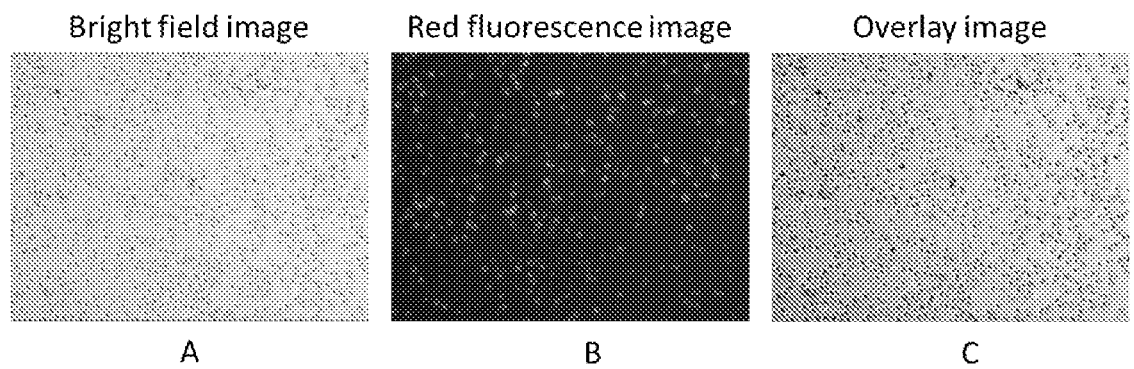

FIG. 3B depicts Target sequence of FUT8 exon 7, CRISPR recognition sequences are underlined. The CRISPR recognition sequences are set forth in SEQ ID Nos. 6 and 11, and the entire sequences of the 5' to 3' strands are set forth in SEQ ID No. 41 (top strand) and SEQ ID No.43 (bottom strand).

FIG. 4 depicts Transfection efficiency of CHO S cell line with Red fluorescence protein expression plasmid. The data suggests high level of transfection efficiency. Panel A represents Bright field microscope image. Panel B represents Fluorescence image. Panel C represents overlay image showing large number of red fluorescent cells.

Figure 5A:
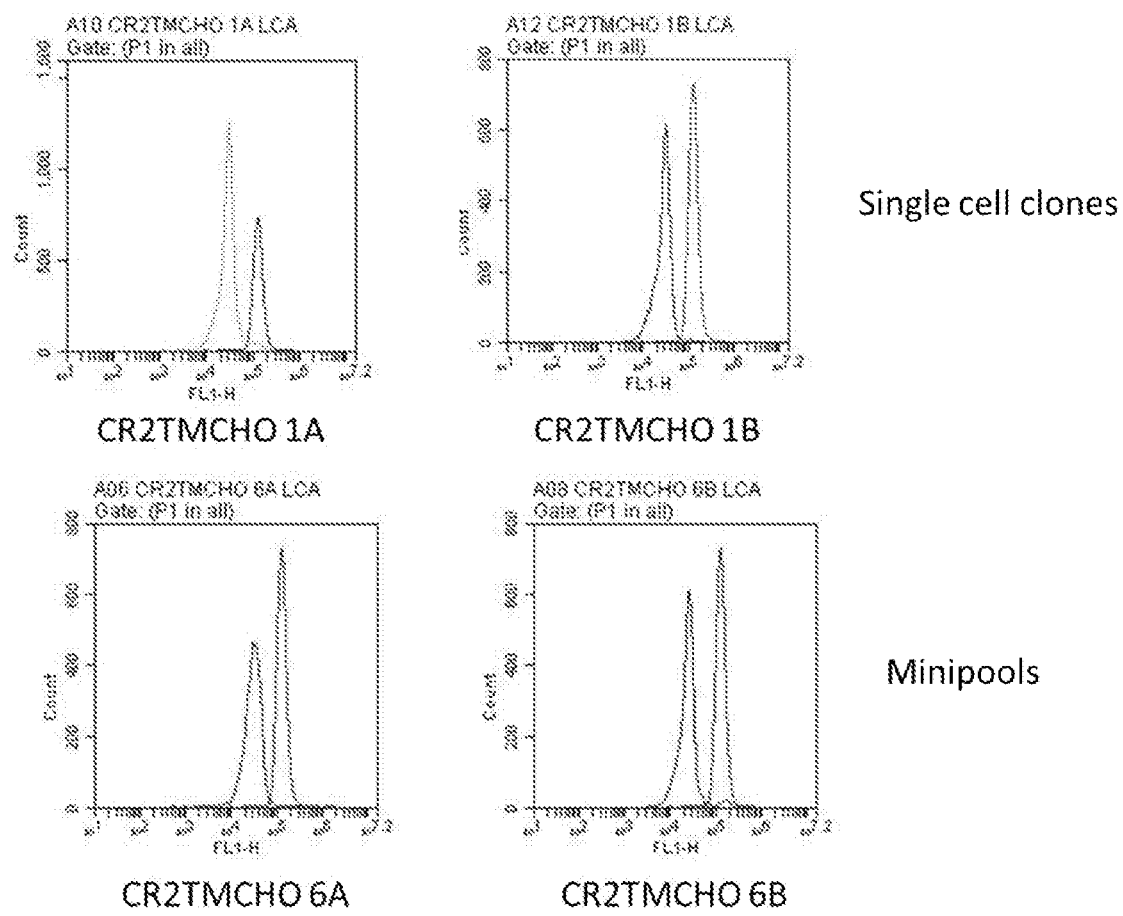

FIG. 5A depicts Fluorescence shift observed in LCA-FITC assay of CHO S cells transfected with CRISPR/Cas system targeting FUT8 gene. The profiles of multiple single clonal cell lines and minipool cell lines suggest Fucose knock out phenotype.

Figure 5B:
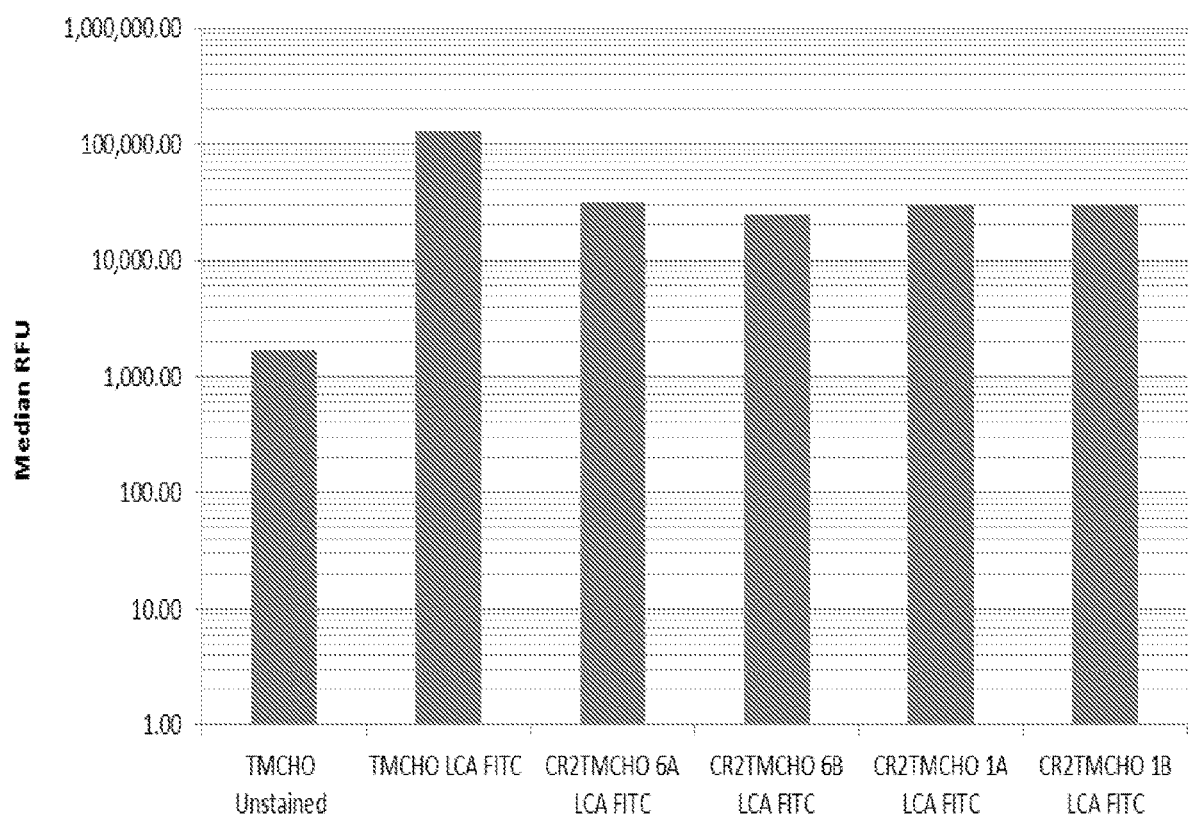

FIG. 5B depicts Fluorescence shift observed in LCA-FITC assay of CHO S cells transfected with CRISPR/Cas system targeting FUT8 gene. The single cell clonal cell lines and the minipool cell lines reveal 4-5 folds reduction in fluorescence indicating Fucose knock out phenotype of these cell lines.

Figure 6:
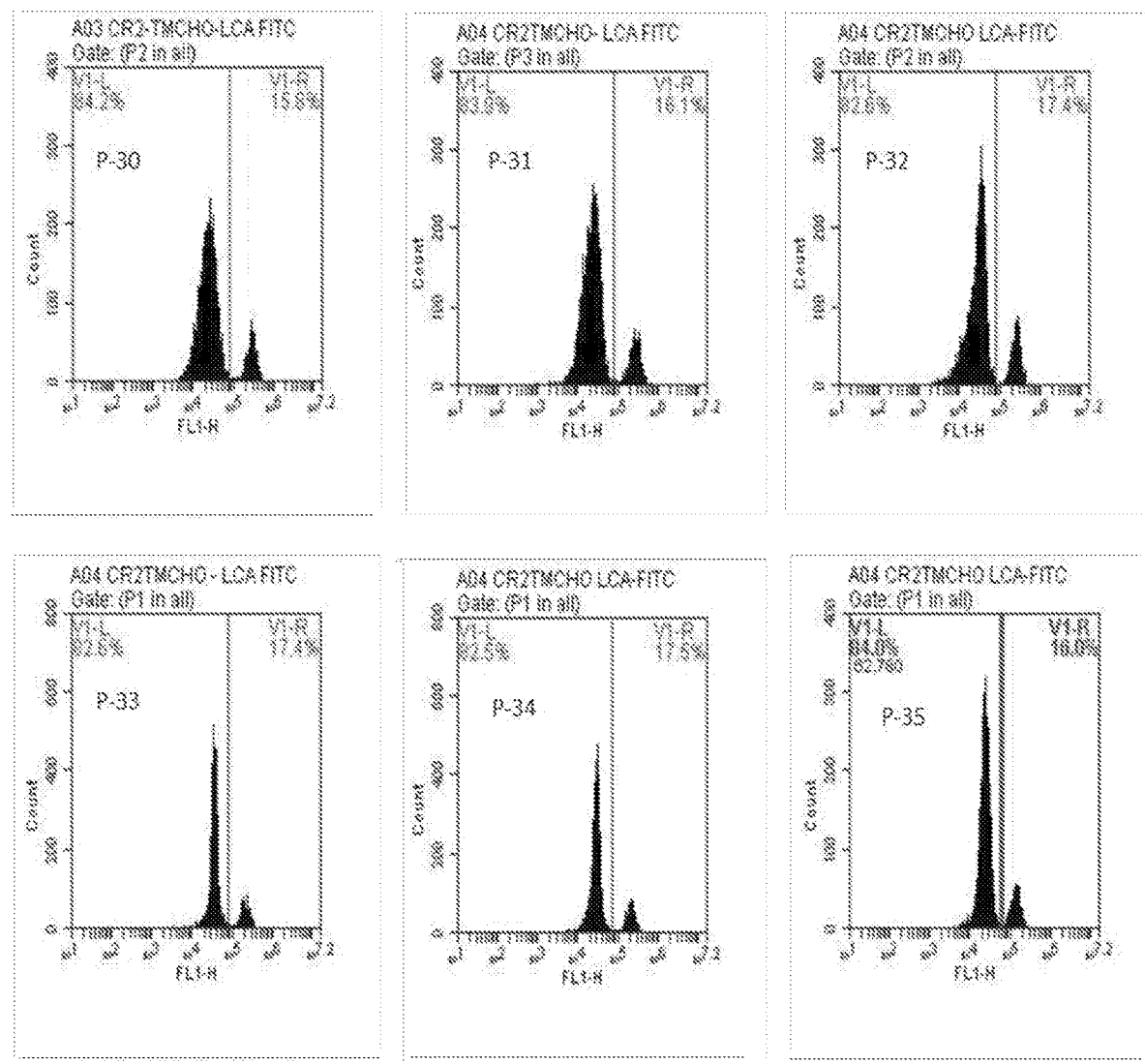

FIG. 6 depicts LCA-FITC binding profile of transfected pool over multiple passages indicating stability of Fucose knock out phenotype over multiple generations.

Figure 7:
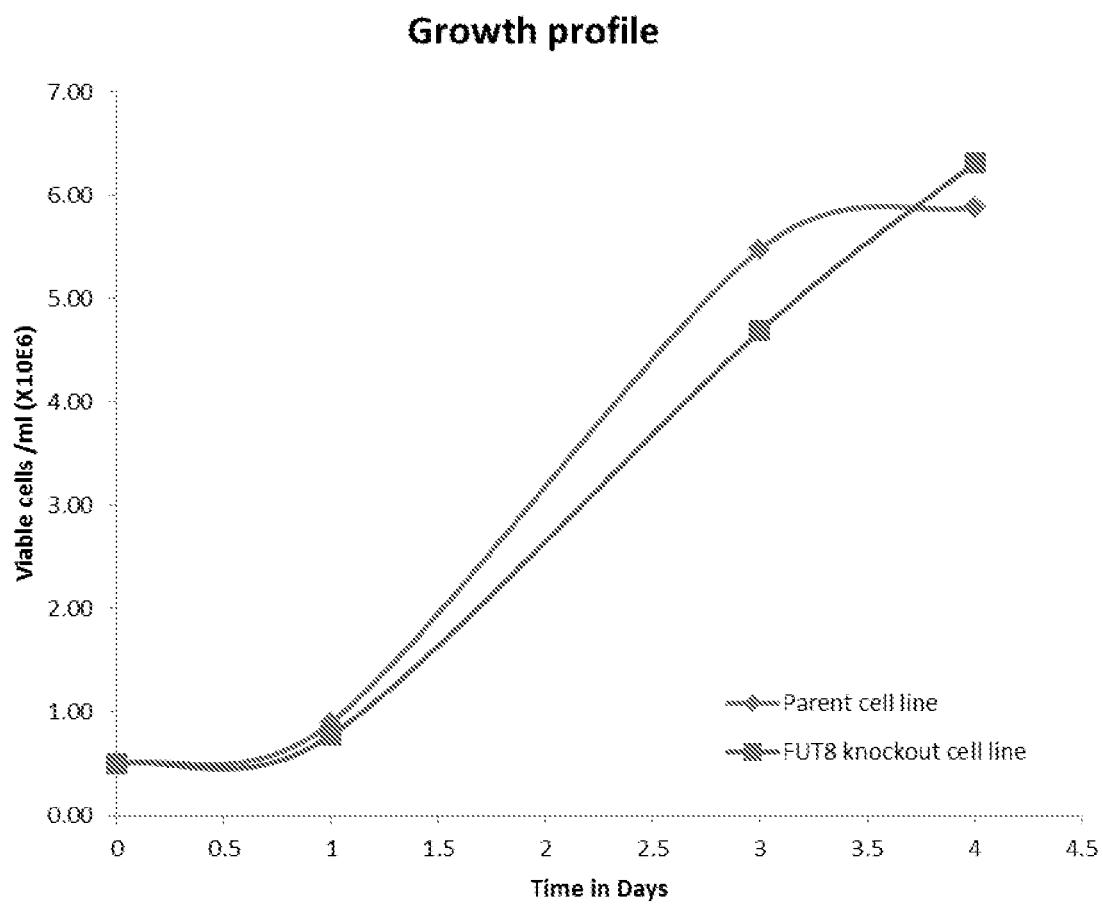

FIG. 7 depicts Growth profile of representative Fucose knock out CHO-S cell line over expressing Afucosylated Anti Her2 Antibody compared to parental CHO S cell line.

Figure 8A:
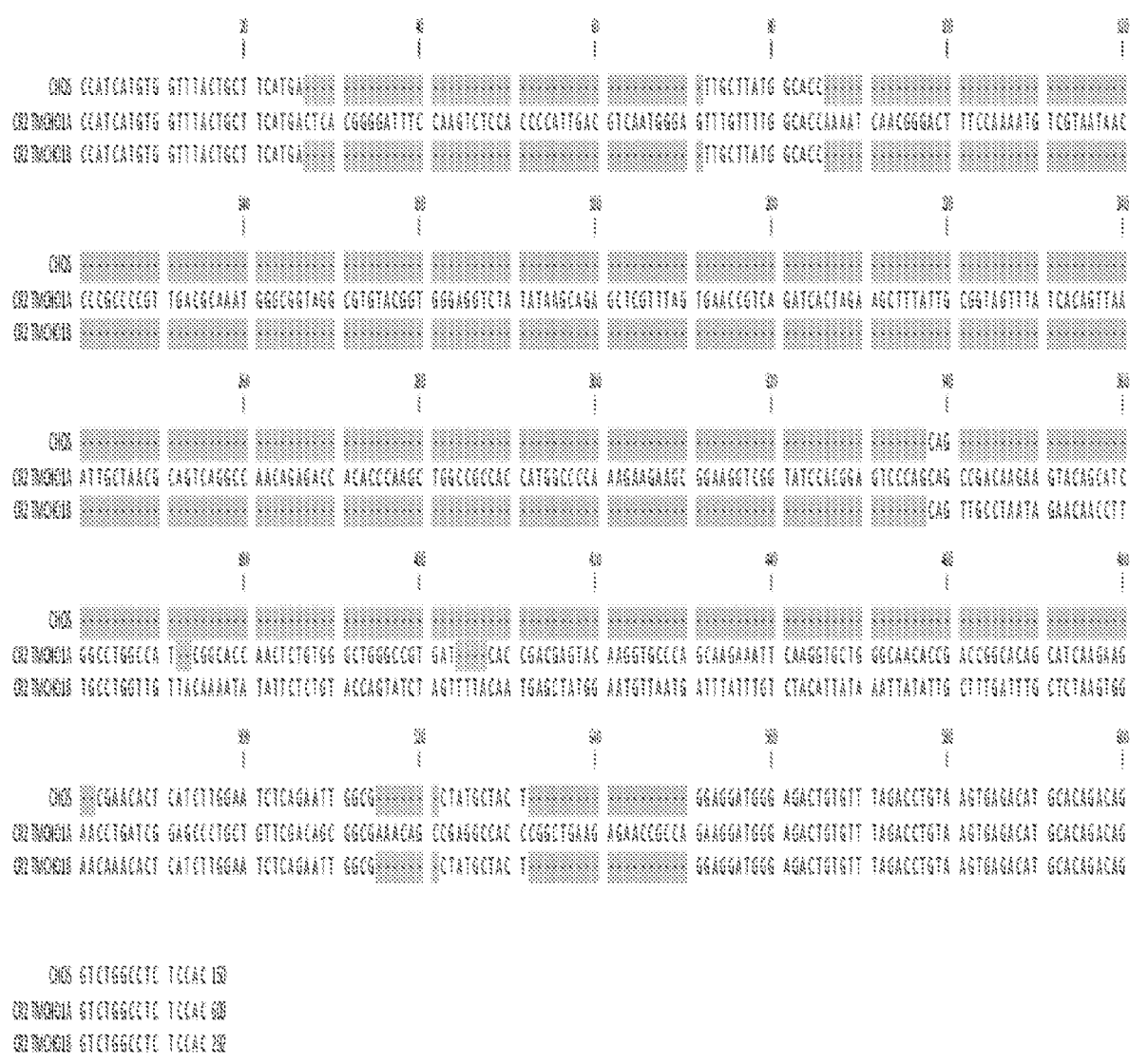

FIG. 8A depicts Genome data analysis at the FUT8 locus reveals long insertion and deletion of nucleotide in alleles of Fucose knock out CHO S cell lines transfected with CRISPR/Cas system targeting FUT8 locus. The sequences are set forth in SEQ ID No. 31 (CHOS), SEQ ID NO.32 (Clone CR2TMCHO1A), and SEQ ID No. 33 (Clone CR2TMCHO 1B).

Figures 8B, 9:
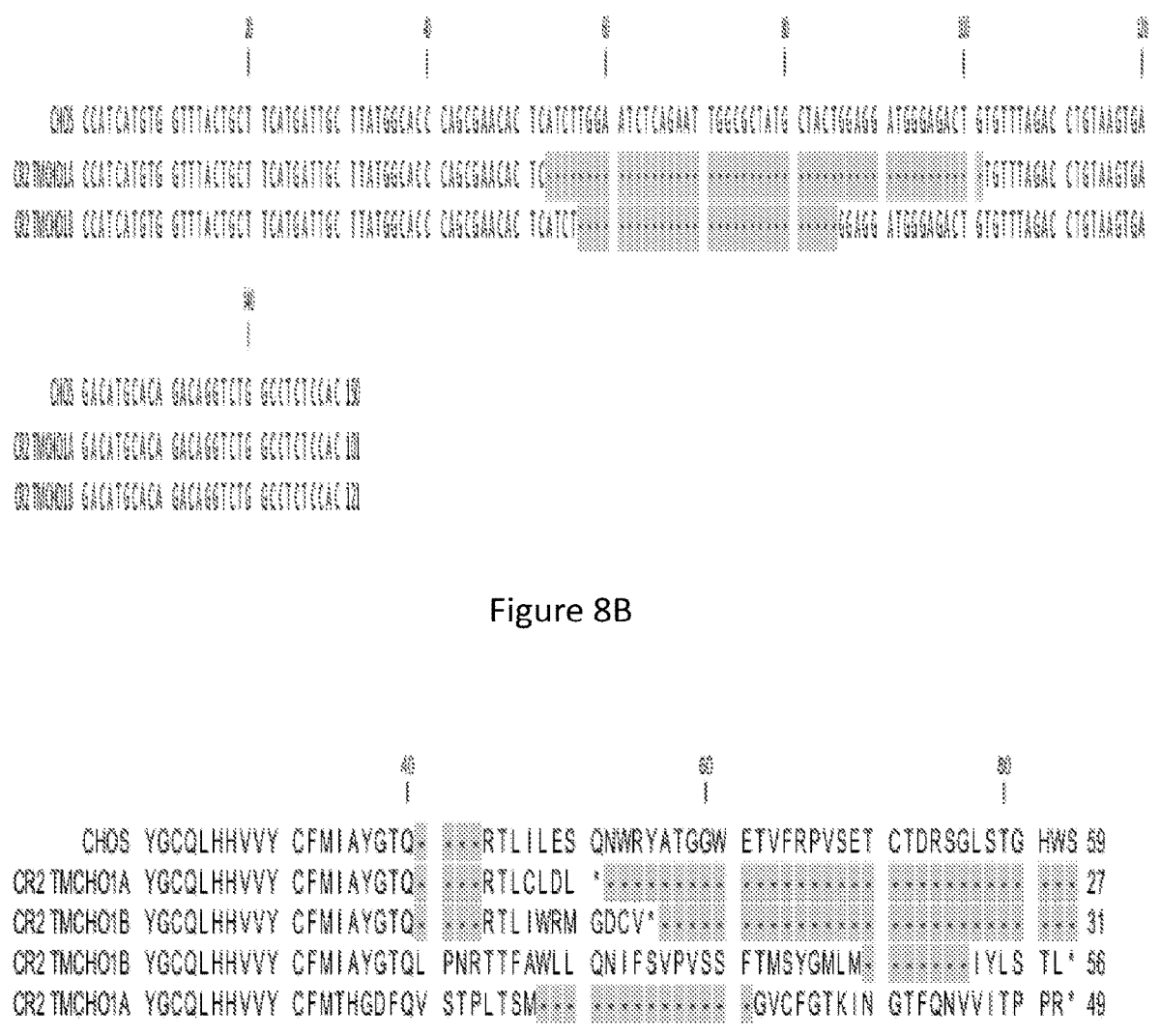

FIG. 8B depicts Genome data analysis at the FUT8 locus reveals deletions of nucleotide in alleles of Fucose knock out CHO S cell lines transfected with CRISPR/Cas system targeting FUT8 locus. The sequences are set forth in SEQ ID No. 31 (CHOS), SEQ ID NO.34 (Clone CR2TMCHO1A), and SEQ ID No. 35 (Clone CR2TMCHO 1B).

FIG. 9 depicts Amino acid sequence analysis of alleles of Fucose knock out CHO S cell lines transfected with CRISPR/Cas system targeting FUT8 locus reveals frame shift mutations and introduction of stop codons. These mutations have resulted in non-functional FUT8 gene. The sequences are set forth in SEQ ID No. 36 (CHOS), SEQ ID No. 37 (first Clone CR2TMCHO1A variant), SEQ ID No. 38 (first Clone CR2TMCHO 1B variant), SEQ ID No.39 (second Clone CR2TMCHO 1B variant), and SEQ ID NO.40 (second Clone CR2TMCHO1A variant.

Figures 10A, 10B:
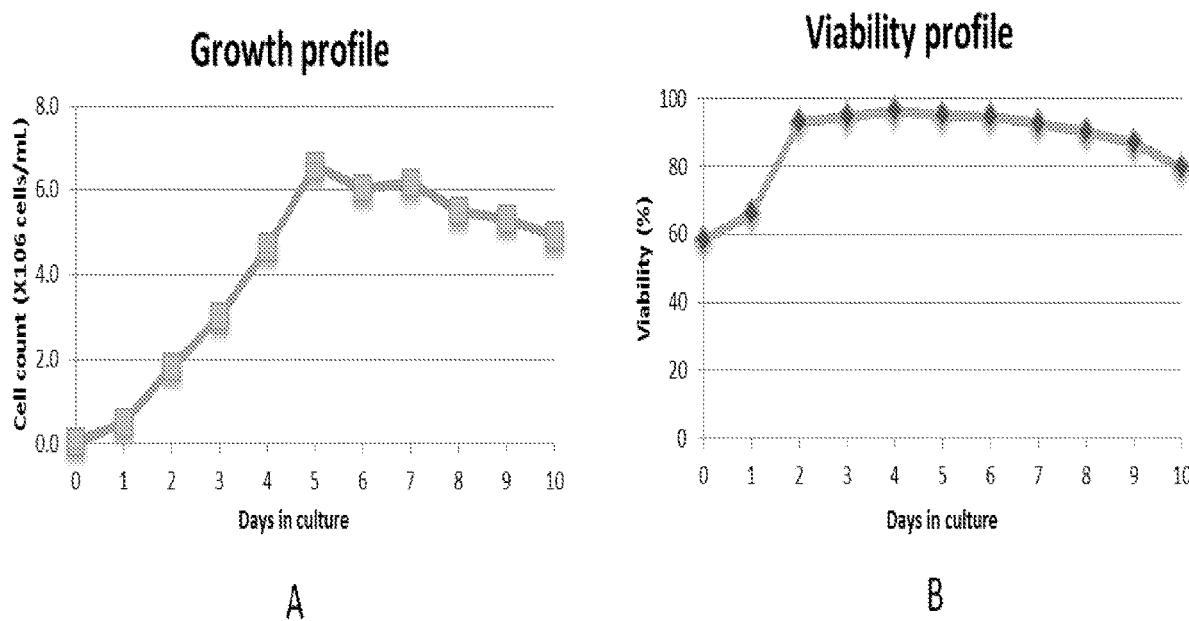

FIGS. 10A and 10B depict Cell count and viability profiles of CHO S clonal cell line producing Afucosylated AntiHer2 Antibody in 2 liter bioreactor fed batch culture.

Figures 11A, 11B:
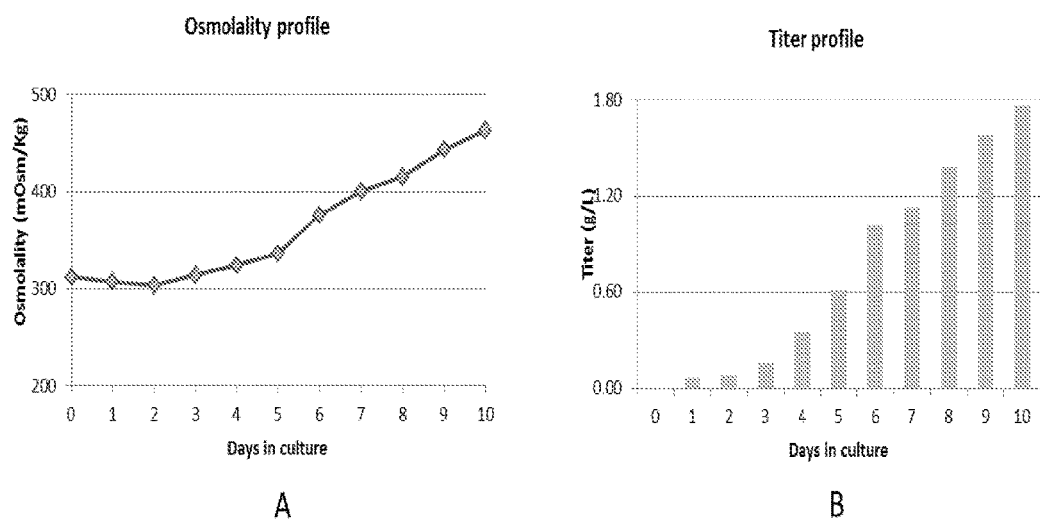

FIGS. 11A and 11B depict Osmolality and Antibody titer profiles of CHO S clonal cell line producing Afucosylated AntiHer2 Antibody in 2 liter bioreactor fed batch culture.

FIGS. 12A and 12B depict Glucose and Glutamine profiles of CHO S clonal cell line producing Afucosylated AntiHer2 Antibody in 2 liter bioreactor fed batch culture.

FIGS. 13A and 13B depict Ammonia and Lactate profiles of CHO S clonal cell line producing Afucosylated AntiHer2 Antibody in 2 liter bioreactor fed batch culture.

FIG. 14 depicts Afucosylated AntiHer2 Antibody purification from 2 liter Bioreactor fed batch culture of fucose knock CHO S cell clone. Panel A represents Affinity chromatography with protein A purification. Panel B represents Anion exchange chromatography. Panel C represents Cation exchange chromatography.

Figure 15:
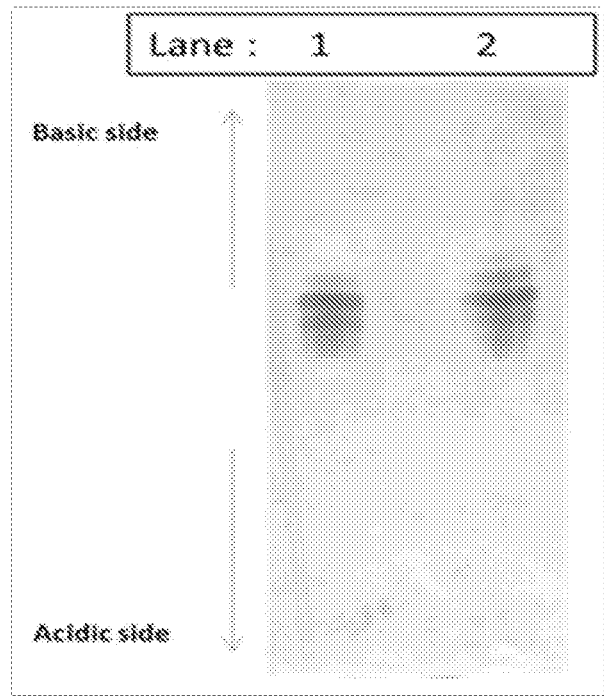

FIG. 15 depicts Comparative IEF study of Trastuzumab and Afucosylated AntiHer2 Antibody produced from the Fucose knock out CHO S clone.

FIG. 16 depicts Comparative SDS PAGE study of Trastuzumab and Afucosylated AntiHer2 Antibody produced from the Fucose knock out CHO S clone.

FIG. 17 depicts Comparative Western blot analysis of Trastuzumab and Afucosylated AntiHer2 Antibody produced from the Fucose knock out CHO S clone.

Figure 18:
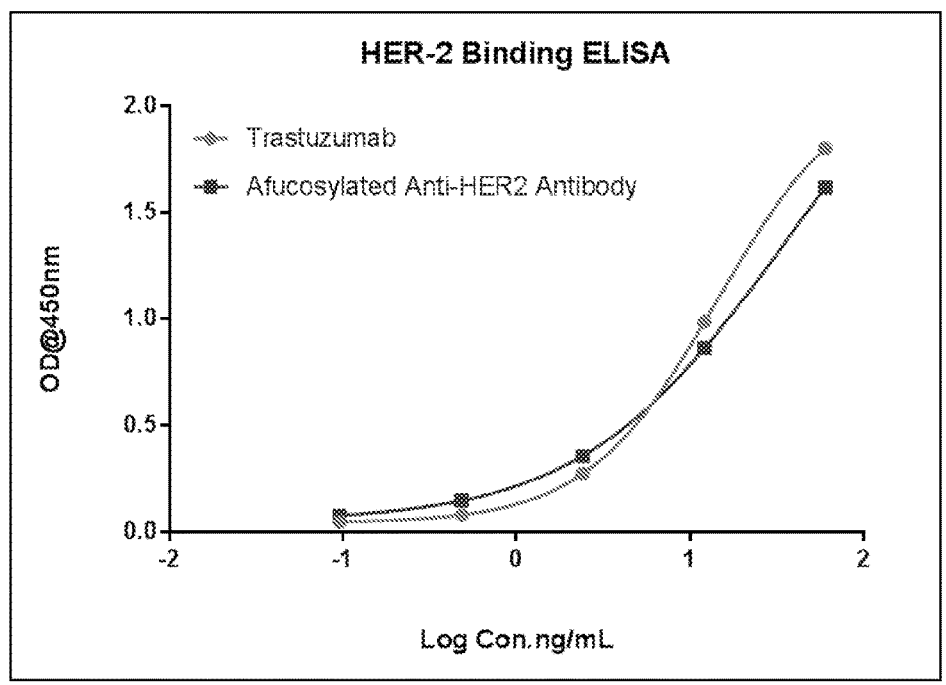

FIG. 18 depicts Comparative Her2 binding ELISA study of Trastuzumab and Afucosylated AntiHer2 Antibody produced from the Fucose knock out CHO S clone. Data suggests very similar HER2 antigen binding profiles.

Figure 19:
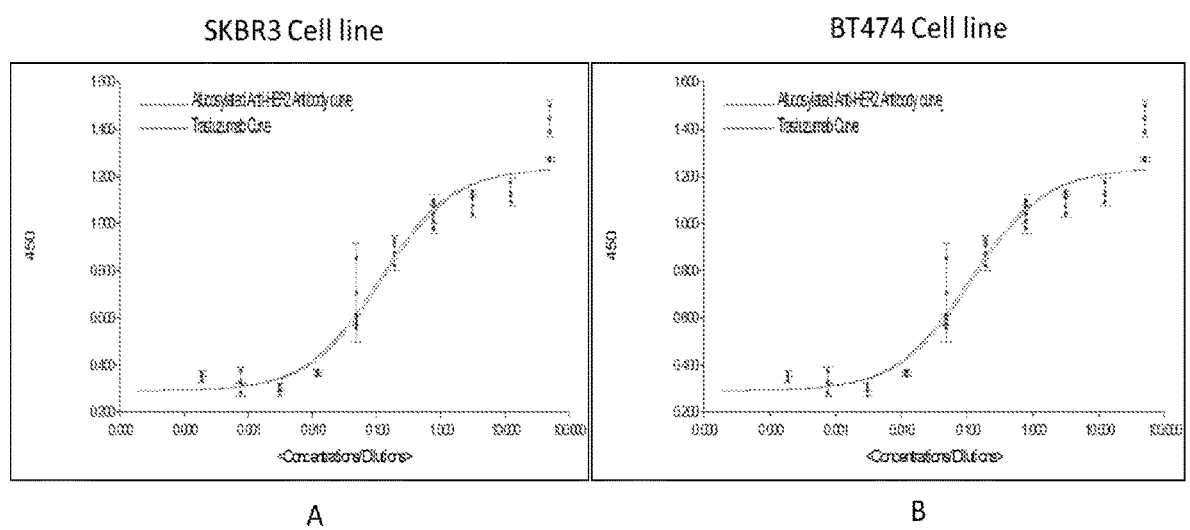

FIG. 19 depicts Comparative cell based ELISA study of Trastuzumab and Afucosylated AntiHer2 Antibody produced from the Fucose knock out CHO S clone. Panel A represents experiments with SKBR3 cell line. Panel B represents experiments with BT474 cell line.

Figure 20:
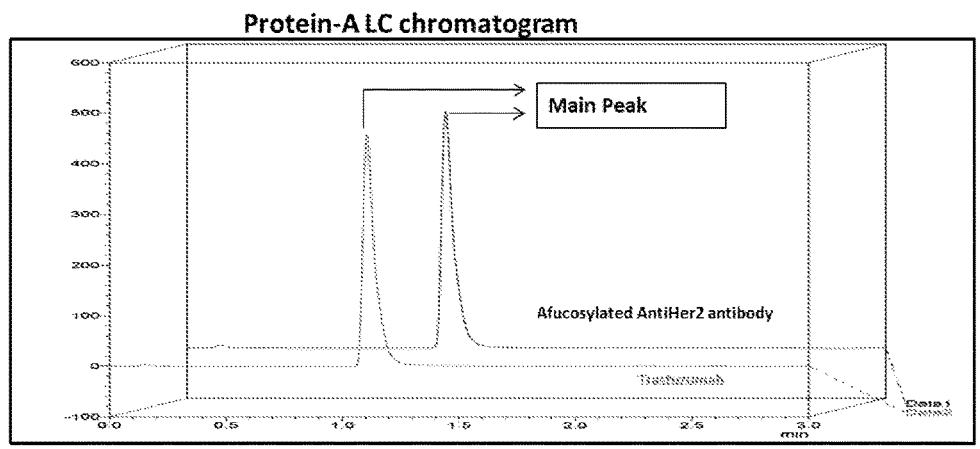

FIG. 20 depicts Comparative protein A liquid chromatography with Trastuzumab and Afucosylated AntiHer2 Antibody produced from the Fucose knock out CHO S clone. Data suggests very similar chromatogram.

Figure 21:
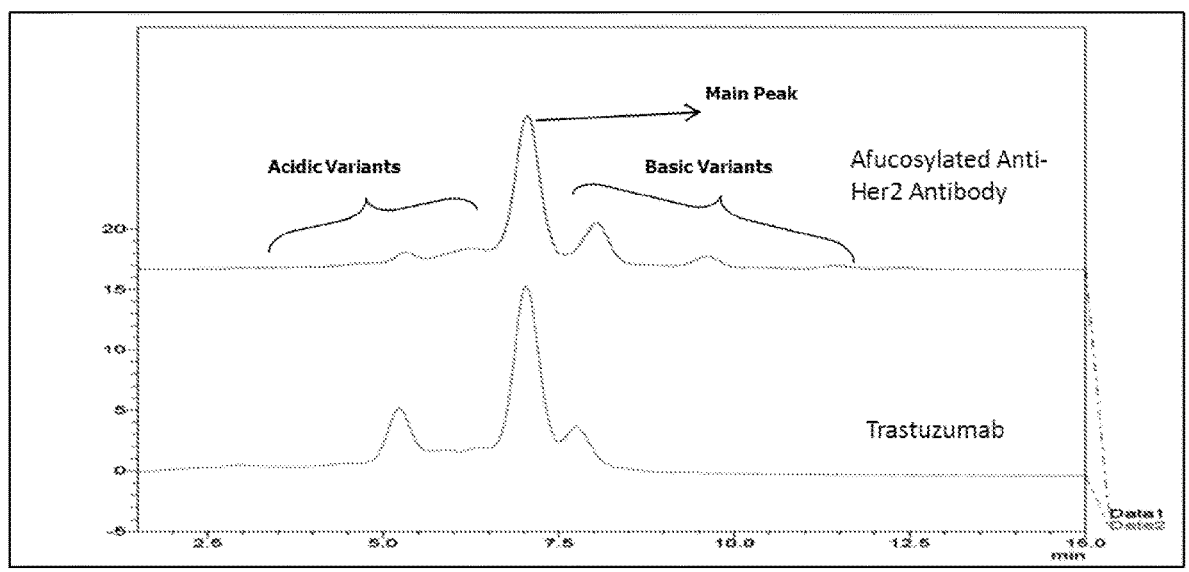

FIG. 21 depicts Comparative Ion exchange chromatography of Trastuzumab and Afucosylated AntiHer2 Antibody produced from the Fucose knock out CHO S clone. Data suggests very similar main peak, acidic and basic variants in both cases.

Figure 22:
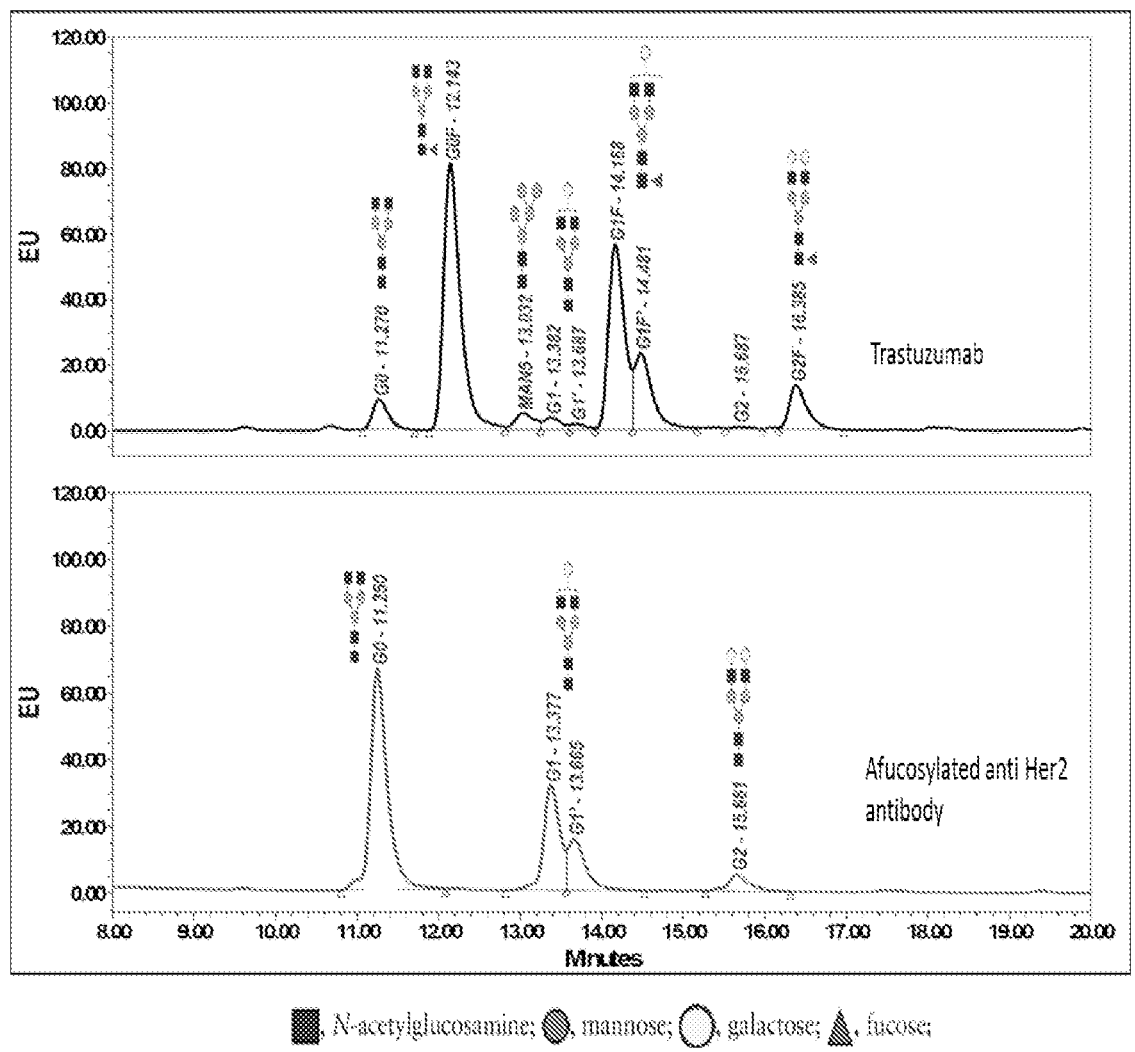

FIG. 22 depicts Comparative glycan analysis of Trastuzumab and Afucosylated AntiHer2 Antibody produced from the Fucose knock out CHO S clone. Major glycan peaks are identified and compared. Glycan analysis of Afucosylated AntiHer2 Antibody product shows complete afucosylation of major glycans represented by complete shift of the peaks to Afucosylated glycan position in lower panel.

Figure 23:
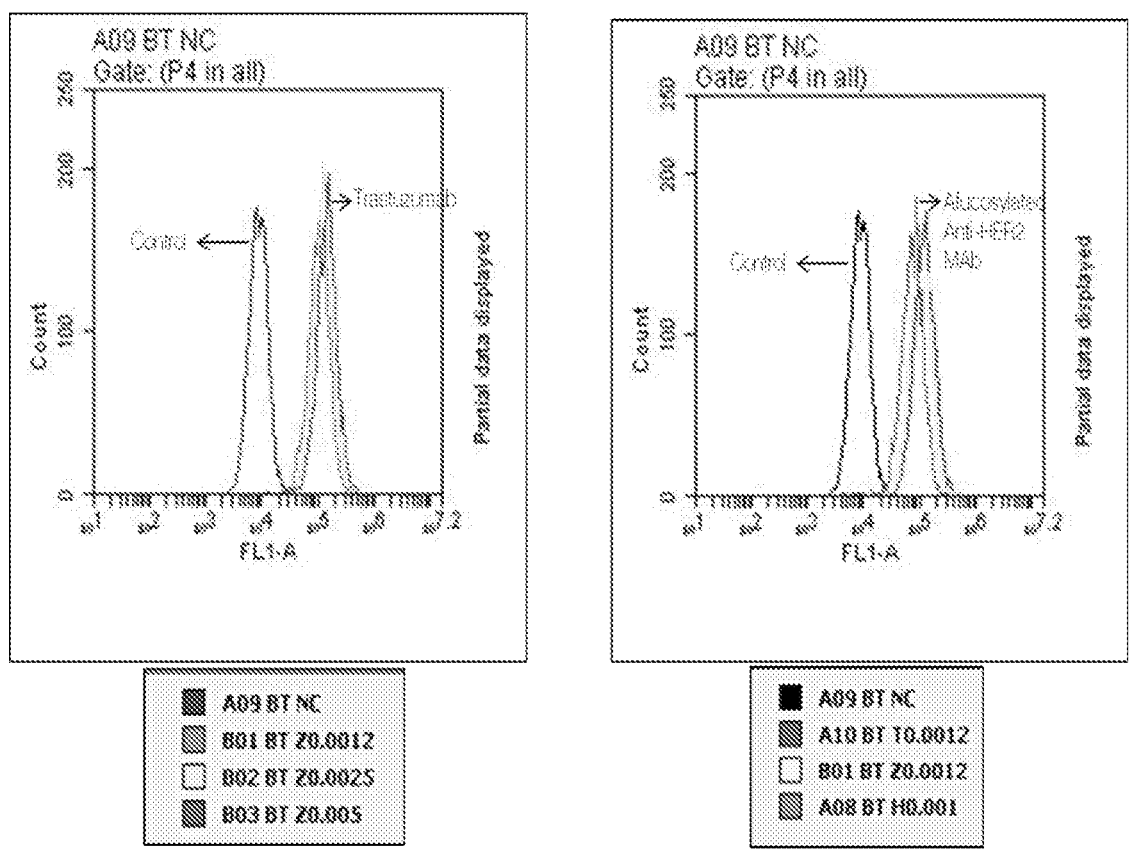

FIG. 23 depicts Flow cytometry analysis of Afucosylated Anti Her2 Antibody and Trastuzumab product. Data reveals equivalent binding of Her2 antigen by both products indicating afucosylation of the antibody did not alter Her2 antigen recognition by the product.

Figure 24:
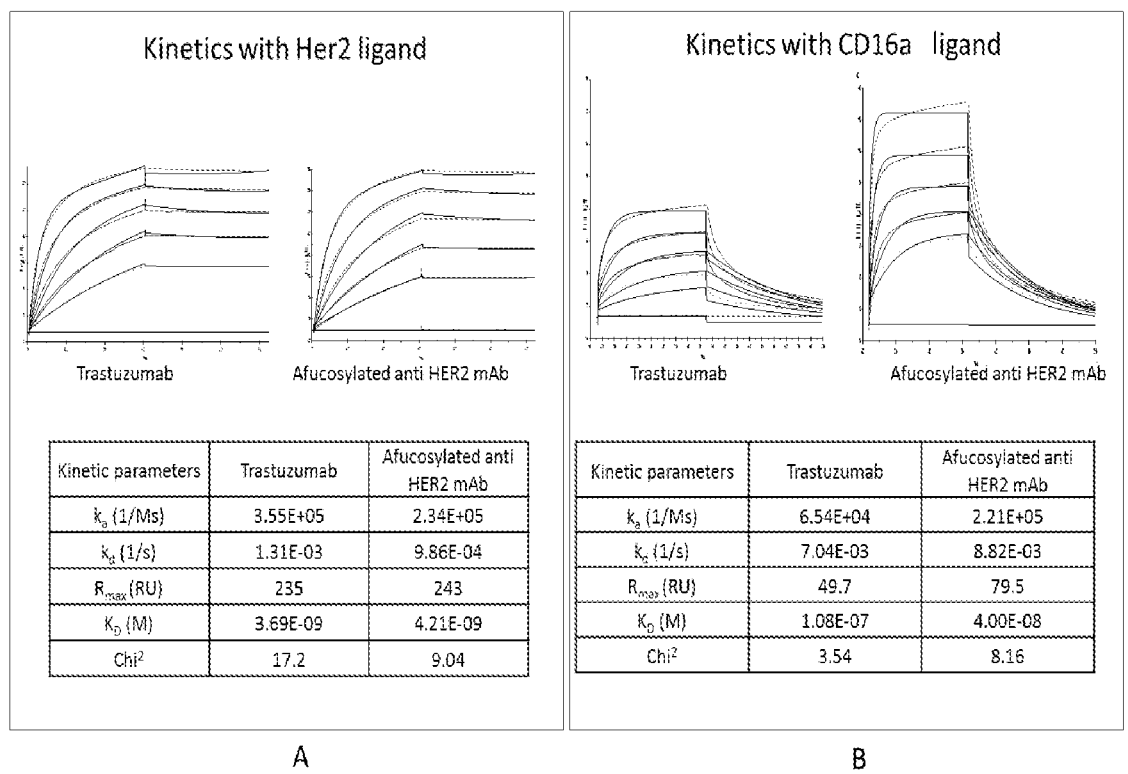

FIG. 24 depicts Surface Plasmon Resonance (SPR) analysis of Afucosylated Anti Her2 Antibody and Trastuzumab product. Panel A indicates binding kinetics of Afucosylated Anti Her2 Antibody and Trastuzumab products with Her2 ligand. Panel B indicates binding kinetics of Afucosylated Anti Her2 Antibody and Trastuzumab products with CD16a ligand.

Figure 25:
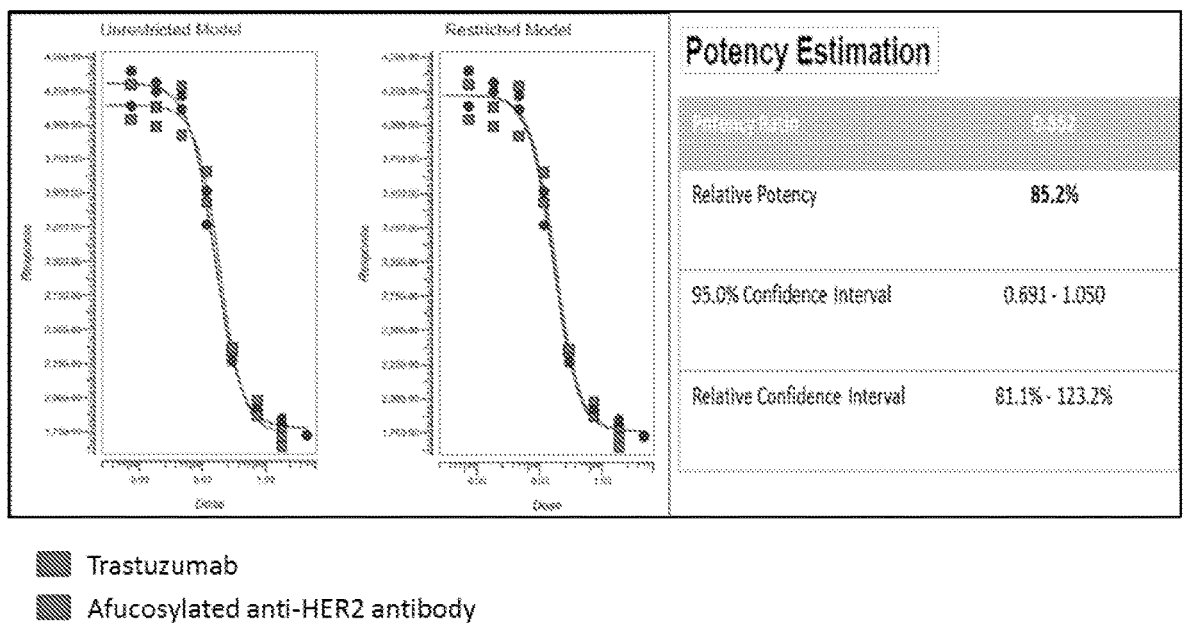

FIG. 25 depicts Antiproliferation assay of Afucosylated Anti Her2 Antibody and Trastuzumab product using BT474 cell line. The data suggests cytostatic relative potency of Afucosylated anti-Her2 Antibody product is comparable to Trastuzumab.

Figure 26:
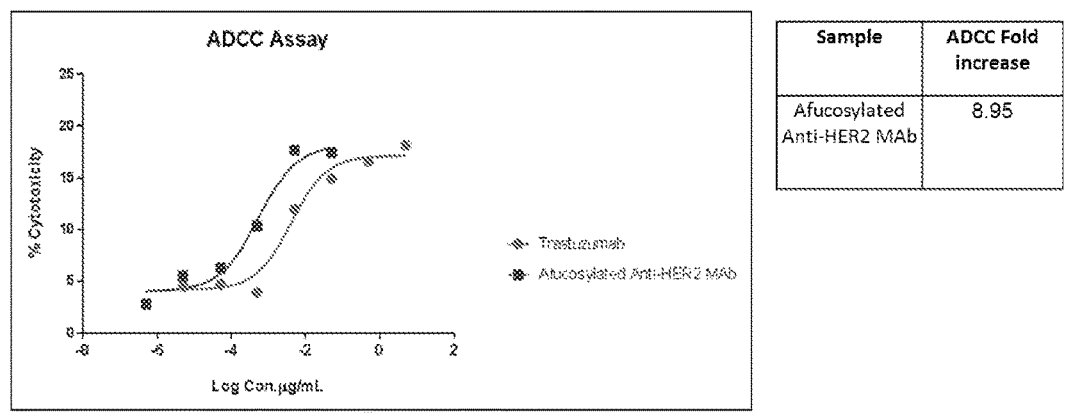

FIG. 26 depicts Antibody dependent cellular cytotoxicity (ADCC) assay of Afucosylated Anti Her2 Antibody and Trastuzumab product using BT474 cell line as target cell line and isolated PBMCs as effector in 1:20 ratio. The data suggests about 9 folds improvement in ADCC efficiency of the Afucosylated AntiHer2 Antibody product.

DETAILED DESCRIPTION OF THE DISCLOSURE

The present disclosure relates to a cell comprising a gene encoding antibody involved in Antibody-dependent cell-mediated cytotoxicity (ADCC) and vector comprising a CRISPR DNA binding domain selected from the group consisting of SEQ ID No. 11 and SEQ ID No. 13 or combination thereof.

In an embodiment of the present disclosure, the vector further comprises a nuclease.

In another embodiment of the present disclosure, the cell is an antibody producing cell; and the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

In yet another embodiment of the present disclosure, the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

In still another embodiment of the present disclosure, the cell is a CHO cell; and wherein the antibody is anti-Her2 antibody.

The present disclosure also relates to a method of obtaining a fucose knockout cell, said method comprising a step of transfecting a cell with a CRISPR nuclease construct to obtain a fucose knockout cell.

In an embodiment of the present disclosure, the cell comprises a gene encoding antibody involved in Antibody-dependent cell-mediated cytotoxicity (ADCC).

In another embodiment of the present disclosure, the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

In yet another embodiment of the present disclosure, the CRISPR nuclease construct comprises CRISPR DNA binding domain selected from the group consisting of SEQ ID No. 11 and SEQ ID No. 13 or combination thereof.

In still another embodiment of the present disclosure, the CRISPR-nuclease construct disrupts Fut8 gene of the cell; and wherein the Fut8 gene sequence is disrupted by cleavage at Exon 7.

In still another embodiment of the present disclosure, the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

The present disclosure also relates to a method of obtaining afucosylated protein, said method comprising step of obtaining a protein expressed by the fucose knockout cell obtained by the method mentioned above.

In an embodiment of the present disclosure, the protein is an antibody involved in Antibody-dependent cell-mediated cytotoxicity (ADCC).

In another embodiment of the present disclosure, the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

In yet another embodiment of the present disclosure, the antibody is an anti-Her2 antibody.

In still another embodiment of the present disclosure, the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

The present disclosure also relates to an afucosylated protein.

In an embodiment of the present disclosure, the protein is an antibody involved in Antibody-dependent cell-mediated cytotoxicity (ADCC).

In another embodiment of the present disclosure, the protein is an antibody selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

In yet another embodiment of the present disclosure, the antibody is an anti-Her2 antibody.

In still another embodiment of the present disclosure, the protein is obtained by the method as mentioned above.

The present disclosure also relates to a composition comprising the protein as mentioned above, optionally along with pharmaceutically acceptable excipient.

The present disclosure also relates to Afucosylated protein as mentioned above, for use in managing disorder selected from the group consisting of cancer, autoimmune disorder, viral infectious disease, bacterial infectious disease, inflammation and tumour or combinations thereof.

The present disclosure also relates to a method of managing disorder selected from the group consisting of cancer, autoimmune disorder, viral infectious disease, bacterial infectious disease, inflammation and tumour or combinations thereof, said method comprising step of administering the afucosylated protein as mentioned above to a subject in need thereof.

In an embodiment of the present disclosure, the method of managing disorder and use in managing disorder is in a suitable subject, including man.

In the present disclosure, a cell without fucosylation activity is also referred to as "Fucose Knockout" of "FKO" cell.

The terms "non-fucosylated antibody", "afucosylated antibody" 0% fucosylated antibody", "afucosylated monoclonal antibody", afucosylated Mab" and "100% non-fucosylated antibody" have the same scope and meaning, and are used interchangeably throughout the disclosure.

The present disclosure relates to production of non-fucosylated or afucosylated proteins, from cell encoding said protein.

In an embodiment, the cell produces non-fucosylated monoclonal antibody.

In a non-limiting embodiment, the non-fucosylated antibody is IgG1 monoclonal antibody.

In a non-limiting embodiment, the non-fucosylated antibody is anti-Her2 monoclonal antibody.

The terms "Innovator", "Herclon", "Trastuzumab Innovator", "Innovator Herclon", have the same meaning and scope and are used interchangeably. All the terms relate to an anti-Her2 antibody, which is the first available and commercialized antibody for use in Breast Cancer.

The present disclosure employs the CRISPR technology to disrupt Fut8 gene and produce non-fucosylated proteins.

The CRISPR (Clustered, Regularly Interspaced, Short Palindromic Repeat) system is an adaptable, naturally occurring immune mechanism, used by many bacteria to protect themselves from foreign nucleic acids, such as viruses or plasmids. CRISPRs are segments of prokaryotic DNA containing short repetitions of base sequences, followed by short segments of "spacer DNA". This Spacer DNA is foreign DNA obtained from previous exposures to a bacterial virus or plasmid. A set of enzymes called Cas (CRISPR-associated proteins) enzymes are found in association with these CRISPR sequences, and Cas are nucleases which can precisely snip DNA.

The bacterium copies the genetic material in each spacer DNA into an RNA molecule. Cas enzymes then take up one of the RNA molecules, which are referred to as the guide RNAs (gRNA). Together they form the CRISPR-Cas system. When the system encounters DNA from a virus that matches the CRISPR RNA, the RNA hybridises to the DNA sequence and the Cas enzyme then cleaves the DNA in two, preventing the virus from replicating.

There are various Cas enzymes that work in conjunction with CRISPR, but the most well-known and frequently employed in genetic engineering is Cas9 nuclease, which is derived from *Streptococcus pyogenes*. Together, they form the CRISPR/Cas9 system, called the type II CRISPR system.

Cas9 has been shown to be a key player in certain CRISPR mechanisms, specifically type II CRISPR systems where only one Cas protein is required. In this system, the endonuclease Cas9 participates in the cleaving of the target DNA. The Cas9 function is dependent on presence of two nuclease domains, a RuvC-like nuclease domain located at the amino terminus and a HNH-like nuclease domain that resides in the mid-region of the protein.

For site specific DNA recognition and cleavage, the nuclease Cas9 must complex with two RNA sequences, a crRNA (CRISPR RNA) and a separate trans-activating crRNA (tracrRNA or trRNA), that is partially complementary to the crRNA. The tracrRNA is required for crRNA maturation from a primary transcript encoding multiple pre-crRNAs. This occurs in the presence of RNase III and Cas9. During the cleavage of target DNA, the HNH and RuvC-like nuclease domains of the Cas9 nuclease cut both DNA strands, generating double-stranded breaks (DSBs). The recognition sites are defined by 20-nucleotide target sequence within an associated crRNA transcript. The HNH domain cleaves the complementary strand, while the RuvC domain cleaves the non-complementary strand. The double-stranded endonuclease activity of Cas9 also requires that a short conserved sequence, (2-5 nts) known as Protospacer-Associated Motif (PAM), follows immediately 3'—of the crRNA complementary sequence in the target DNA. The requirement of PAM sequence is obligatory for CRISPR/Cas function.

In general, a two vector system is used for CRISPR mediated gene editing, 1) a Cas9 endonuclease and 2) a complex of crRNA (CRISPR RNA) and tracrRNA (trans-activating crRNA). When these two constructs are co-expressed in mammalian cells, they form a complex and are recruited to target DNA sequence. The crRNA and tracrRNA are combined to form a chimeric guide RNA (gRNA) with the same function—to guide Cas9 to target gene sequences.

Homologous recombination mediated gene editing technologies are the first of its kind to be used for gene editing. However, frequency of successful events is very rare using HR, 1 in every $3 \times 10^4$ cells.

In recent days, Zinc finger nuclease is becoming popular as it allows higher specificity of targeting with higher frequency of successful mutant events. It uses DNA binding proteins with nuclease activity, that binds to DNA and creates site-specific DSBs. While effective, these methods require extensive protein engineering tools to be successful and thereby limit flexibility in targeting complex genome sequences. The adaptation of CRISPR for mammalian cells has revolutionized genome editing with higher accuracy and ease of designing. Unlike ZFN, CRISPR/Cas does not require protein engineering for every gene being targeted.

The CRISPR system only requires a few simple DNA constructs to encode the gRNA and Cas9.

Although it is rare for a 20 bp gRNA sequence to have 100% homology at multiple sites throughout the genome, sgRNA-Cas9 complexes are tolerant of several mismatches in their targets. Cas9 has been reported to bind multiple locations in genome nonspecifically. However, it creates DNA double strand break only at a handful of those sites. Experimental data also suggests that certain levels of mismatch at the DNA target site allows DNA double strand break. Therefore, strategies for increasing CRISPR/Cas specificity are pursued.

One such observation is a point mutation of Aspartate to Alanine (D10A) mutation at the RuvC catalytic domain resulting in single strand breaks (nicks) instead of double strand breaks. The mutant Cas9 is known as Cas9n. Using Cas9n at two neighbouring DNA target site allows DNA nicks at close proximity, and if the target sites are appropriately spaced, it creates a double strand break.

Therefore, the specificity of DSB creation is higher, which is eventually repaired by NHEJ mechanism. Nonspecifically bound Cas9n creates only nicks which is generally repaired through HR mediated repair and rarely causes mutation or off target effects. In this disclosure, Cas9n and CRISPR are used to knockout Fut8 gene.

In an embodiment of the present disclosure, the nuclease used in the CRISPR complex is a Cas nuclease.

In an embodiment of the present disclosure, the nuclease used in the CRISPR complex is a Cas9 nuclease.

In an embodiment of the present disclosure, the nuclease used in the CRISPR complex is a Cas9n nuclease.

In an embodiment of the present disclosure, the CRISPR-nuclease construct is a CRISPR Cas construct.

In the present disclosure, CRISPR-Cas construct upon expression in a cell provides CRISPR-Cas complex.

In the present disclosure, the terms CRISPR-Cas complex and CRISPR-Cas system have the same meaning and scope and are used interchangeably.

The present disclosure relates to a method for obtaining non-fucosylated protein, by disruption or inactivation of the fucosylating machinery in a cell.

In an embodiment, the protein is an antibody.

In a preferred but non-limiting embodiment, the antibody is a monoclonal antibody.

In the most preferred embodiment, the antibody is an anti-Her2 monoclonal antibody.

The present disclosure particularly relates to disruption or inactivation of the FUT8 gene in a cell. The FUT8 gene encodes the enzyme $\alpha$-1,6 fucosyltransferase.

In an embodiment of the present disclosure, the cell is a cell that already expresses a protein.

In an embodiment of the present disclosure, the cell is a cell that already expresses an antibody.

In an embodiment of the present disclosure, the cell is a cell that is known to expresses a protein.

In an embodiment of the present disclosure, the cell is a cell that is known to express an antibody.

In an embodiment of the present disclosure, the cell is a cell that expresses an antibody, and a gene encoding an antibody is introduced into the cell.

In an embodiment, the antibody produced by the method of the present disclosure is a therapeutic antibody.

In an embodiment, the cell is a eukaryotic cell.

In an embodiment, the cell is mammalian cell.

In embodiments of the present disclosure, the cell line is selected from the group consisting of COS, CHO-S, CHO-K1, CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, Hybridoma cell which produces antibody, embryonic stem cell, Namalwa cell, insect cell line from *Spodoptera fugiperda* (Sf), *Pichia, Saccharomyces* and *Schizosaccharomyces*.

In a non-limiting embodiment, the cell is Chinese Hamster Ovary cell.

In a non-limiting embodiment, the cell is Chinese Hamster Ovary S (CHO-S) cell.

In a non-limiting embodiment of the present disclosure, the cell is a cell with Glutamine synthetase knockout (GS−/−), preferably a CHO S cell with Glutamine synthetase knockout (GS−/−).

In an embodiment, the CHO S cell is an antibody producing cell.

In an embodiment, the CHO S cell produces Anti Her2 monoclonal antibody.

GPEx® technology, used in an embodiment of the present disclosure, is a well known technique and is based on a highly efficient retroviral vector that transfects 100% of target cells. The advantage of GPEx® is:

Single integration site for each copy of the vector

No selection marker required.

A person skilled in the art would know how to use GPEx® technology in conjunction with the methods of the present disclosure.

In an embodiment, the method of the present disclosure relates to using parental CHO-S cell line overexpressing Anti-Her2 antibody to obtain Fucose KO cell line and subsequently afucosylated Anti-her2 antibody product development, the method comprising the following steps:

a) Obtaining fucose knock out cell line by transfection with CRISPR Nuclease construct;

b) Confirming fucose knock out status of the cell line through flow cytometry assay;
c) Growing Fucose knock out cell line expressing anti-Her 2 monoclonal antibody in fermentor using optimized media and feed composition;
d) Purification of anti-Her 2 monoclonal antibody produced from Fucose knock out clonal cell line; and
e) Analysis of purified afucosylated anti-her2 antibody.

The methods of the present disclosure are useful for developing any monoclonal antibody developed against targets which require ADCC for functionality. If any of these targets are produced in a CHO S (or other cell type), a similar strategy of Fucose knock out, as seen in the methods of the present disclosure, could be adopted.

Antibody-dependent cell-mediated cytotoxicity (ADCC) is a cell mediated immune system where immune cells (like natural killer cells) lyse the target cells identified through antibodies against cell surface antigens. A person skilled in the art would know which antibody would be involved in the ADCC mechanism.

Examples of specific antibodies that may be produced using the methods of the present disclosure are in from the field of oncology, viz monoclonal antibodies against targets like CD20, EGFR, Her2, CD19, LAG3, CD40, EpHA3 etc.

A monoclonal antibody may also be produced towards the treatment of autoimmune disorder Rheumatoid Arthritis.

Also, neutralizing antibody against antigens of HIV, HCV, Dengue and other diseases where the infectious organisms are removed through ADCC mechanism, may also be produced by the methods of the present disclosure.

In the present disclosure, the term "managing" or "management" or "manage" of a disorder, includes therapeutic and prophylactic activities. It includes the treatment and healing of a disease or disorder, or ill effects or side effects of the disease or the disorder. It also includes prevention of further progress of the disease or disorder, or ill effects or side effects of the disease or the disorder. It further includes maintenance of the optimum state of an individual.

In an embodiment of the present disclosure, the afucosylated monoclonal antibody of the present disclosure is used in—
 combination therapy with any monoclonal antibody which targets tumor cell death through ADCC,
 bispecific antibody based therapy,
 allogenic NK cell based therapy with Chimeric Antigen Receptor (CAR) vehicles,
 autologous NK cell transplant,
 cytokine stimulated NK cell based therapy, and
 combination therapy with Chimeric Antigen Receptor-T cell therapy (CAR-T cell therapy).

In an embodiment, the cell is referred to as a "Fucose Knockout" cell or "FKO" cell or "Fucose Knockout" platform or "FKO" platform.

In an embodiment, the cell is referred to as a Recombinant cell.

In an embodiment, CRISPR (Clustered Regularly Interspaced Short Palindromic Repeats)—Cas complex is used to disrupt or inactivate the Fucosylation pathway of a cell.

In the de novo pathway of fucosylation, GDP-fucose is synthesized through conversion of GDP-mannose to GDP-4-keto-6-deoxy-mannose, catalyzed by the enzyme GDP-mannose 4, 6-dehydratase (GMD). This GDP-Fucose is then transported inside the golgi and used as a substrate for protein fucosylation by the enzyme α-(1-6) fucosyltransferase. The enzyme transfers the fucose moiety from GDP-fucose to N-acetyl glucosamine of the N-glycan chain.

In an embodiment, CRISPR (Clustered Regularly Interspaced Short Palindromic Repeats)—Cas complex) is used to disrupt the Fut8 gene encoding the α-1,6 fucosyltransferase enzyme.

In an embodiment of the present disclosure, the N-terminal catalytic region of fucosyl transferase enzyme is targeted by CRISPR/Cas complex.

In a particular embodiment, Exon 7 of the gene sequence of Fut8 is targeted by CRISPR (Clustered Regularly Interspaced Short Palindromic Repeats)—Cas complex.

In an embodiment of the present disclosure, the Fu.cosyltransferase enzyme is mutated at an amino acid position selected from the group consisting of amino acid sequence at the beta 2 strand and amino acid sequence at 3H2 helix region, both coded by exon 7 coding sequence.

The resulting clones may result in premature translation stop, therefore absence of downstream amino acids such as Arg-365, Arg-366, Asp-368, Lys-369, Glu-373, Tyr-382, Asp-409, Asp-410, Asp-453, Ser-469 and combinations thereof provides a non-functional Fut8 gene.

The CRISPR/Cas constructs are designed as a two vector system, in general. One construct codes for the Cas9 endonuclease expression and the second vector expresses the gRNA—which is made up of the crRNA and tracrRNA. The crRNA is usually designed as a 20 nucleotide long fragment that recognizes the target sequence, depending on proper positioning of tracrRNA, PAM sequence and the functional complex of crRNA-Cas9-tracrRNA. In certain cases, one single vector expresses both gRNA and the Cas9 protein for higher activity and ease of use. Target recognition specificity comes from the crRNA design.

In embodiments of the present disclosure, the DNA binding domain is also referred to as the DNA recognition domain.

In an embodiment of the present disclosure, polynucleotides encoding said CRISPR/Cas complex are also provided, as are cells comprising said polynucleotides.

In a particular embodiment, nucleotides encoding for the DNA binding domain of CRISPR Cas9 complex are provided. In another embodiment, nucleotides encoding for the nuclease domain of CRISPR Cas9 complex are provided.

In an embodiment, the nuclease is Cas9.

In another embodiment, the nuclease is Cas9n (nickase) D10A mutant.

In an embodiment of the present disclosure, the CRISPR/Cas complex recognizes target site in FUT8 gene. In an embodiment of the present disclosure, the nuclease is a homing endonuclease. In another embodiment, the nuclease is a meganuclease. It is also known that the specificity of homing endonucleases and meganucleases can be engineered to bind non-natural target sites. Further, in exemplary embodiments, homing endonucleases include I-SceI, I-CeuI, PI-PspI, PI-Sce, I-SceIY, I-CsmI, I-PanI, I-SceII, I-PpoI, I-SceIII, I-CreI, I-TevI, I-TevII and I-TevIII. Their recognition sequences are known.

In an embodiment, a combination of one or more of the above-mentioned nucleases is used with the DNA binding domain of the CRISPR-Cas protein complex.

In an embodiment, transfection is used to introduce a CRISPR/Cas complex into a cell. Though a lipofection protocol is provided as an exemplary embodiment, any method of transfection known to one skilled in the art is equally applicable to the methods of the present disclosure.

In another embodiment, the present disclosure provides methodologies for producing recombinant proteins in any host cell where the host cell has endogenous FUT8 gene expression which is targeted through CRISPR/Cas technology to disrupt endogenous FUT8 gene as described herein. The resulting cell line is null for FUT8 gene expression and is further used for expression of gene of interest.

In the present disclosure, seventeen FUT8 knock out clonal cell lines are created from a screen of less than 120 clonal cell lines generated after transfection with pD1401 (gRNA 514-553) CRISPR/Cas complex. In comparison, only three FUT8 −/− cell lines could be selected from approximately 120,000 clonal cell lines as reported in the art.

The specificity, safety and simplicity of the protocol are some of the advantages offered by CRISPR/Cas complex and the method of the present disclosure over the prior art methods. CRISPR mediated gene disruption provides a unique advantage of specificity of target locus that allows customized CRISPR/Cas complex to recognize user defined target sequence of any complexity. CRISPR/Cas complex are more effective than ZFN in terms of genome editing efficiency and significantly less toxic, thereby allowing higher efficiency in generating mutant clones against a particular locus. In the present disclosure, FUT8 genomic loci are targeted for sequence specific modification through CRISPR gRNAs.

The methodology described herein has achieved an efficiency of more than 3% success rate of generating FUT8 knock out CHO-S cell line expressing anti Her2 antibody. is This unanticipated achievement following the methodology and the specific CRISPR constructs of the present disclosure has vastly improved the FUT8 knock out cell line development.

Also, in an embodiment, the present disclosure has used only one set of CRISPR constructs targeting a very specific genomic location in the FUT8 DNA sequence of the anti Her2 antibody expressing cell line. Surprisingly, the CRISPR/Cas complex results in not only disrupting the targeted amino acids but also produced long deletions which introduced frame shift mutations and premature stop codon. Thereby, the present disclosure has achieved FUT8 knock out cell lines from the anti Her2 antibody expressing cell line with very minimal DNA modifications at the target locus as well as large genome level modifications at the targeted FUT8. Generation of such a large number of FUT8 knock out cell lines is unexpected, considering the small number of clonal populations screened for fucose knock out phenotype. This surprising achievement provides a unique method where any monoclonal antibody expressing cell line could be used for generating fucose knock out lines and thereby an afucosylated monoclonal antibody product could be generated. The method allows screening of only few cell lines to achieve multiple FUT8 knock out cell lines to establish best performing clonal lines for over expression of afucosylated monoclonal antibody.

In embodiments, inactivating a FUT8 gene in a cell line, results in a cell line which produces proteins at higher levels.

In certain embodiments, inactivating a FUT8 gene provides a cell line in which one or more activities (functions) of a protein is increased, as compared to proteins produced in cells where the FUT8 gene is not inactivated.

In an embodiment, the non-fucosylated antibody exhibits greater effector function than a corresponding fucosylated antibody.

In an embodiment, the non-fucosylated antibody exhibits more efficacious therapeutic properties than a corresponding fucosylated antibody.

In an embodiment, the non-fucosylated antibody exhibits higher Antibody dependent Cellular Toxicity (ADCC) than a corresponding fucosylated antibody.

In an embodiment, the non-fucosylated antibody exhibits up to about 7 to 20 folds higher Antibody dependent Cellular Toxicity (ADCC) than a corresponding fucosylated antibody.

In a non-limiting embodiment, the non-fucosylated antibody exhibits about 8.95 folds higher Antibody dependent Cellular Toxicity (ADCC) than a corresponding fucosylated antibody.

In the present disclosure, the methods, preparation and use of the proteins disclosed employ, unless otherwise indicated, conventional techniques in molecular biology, biochemistry, computational chemistry, cell culture, recombinant DNA technology, Polymerase Chain Reaction (PCR) and related fields. These techniques, their principles, and requirements are explained in the literature and known to a person skilled in the art. The techniques for determining nucleic acid and amino acid sequence identity are known to one skilled in the art.

In the present disclosure, the cell with the disrupted fucosylation machinery is a cell that naturally produces antibodies A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid.

The term "antibody" used here includes both polyclonal and monoclonal antibody preparations and also includes the following: Chimeric antibody molecules, F(ab')2 and F(ab) fragments, Fv molecules, single chain Fv molecules (ScFv), dimeric and trimeric antibody fragments, minibodies, humanized monoclonal antibody molecules, human antibodies, fusion proteins comprising Fc region of antibody and any functional fragments arising out of these molecules, where derivative molecules retain immunological functionality of the parent antibody molecule.

The term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

It is to be noted that clones/cells of the present disclosure are referred to by terms such as CR2TMCHO 1A, CR2TMCHO 1B etc., which are internal denominations and do not represent any particular feature of the cell. These cell lines are developed using pD1401 (gRNA 514-553) CRISPR/Cas complex.

In an embodiment, a composition comprising the non-fucosylated antibody, optionally along with a pharmaceutically acceptable carrier or additive or excipient is provided. Pharmaceutically acceptable carrier or additive or excipient is determined by the composition being administered, as well as by the particular method used to administer the composition and is known to a person skilled in the art.

All sequences provided in the present disclosure are read in the 5' to 3' direction, unless stated otherwise.

Excipients are important for achieving protein stabilization and improving other qualities of biologics. A variety of excipients are added to compositions to stabilize proteins, act as antimicrobials, aid in the manufacture of the dosage form, control or target drug delivery, and minimize pain upon injection.

Excipients can be broadly divided into five categories based on their modes of action:

1. Protein stabilizers: These excipients stabilize the protein native conformation. Examples include polyols, sugars, amino acids, amines, and salting out salts. Sucrose and trehalose are the most frequently used sugars and large polyols are better stabilizers than smaller polyols.
2. Polymers and proteins: Hydrophilic polymers, such as Polyethylene Glycols (PEGs), polysaccharides, and inert proteins, are used non-specifically to stabilize proteins and enhance protein assembly. Examples include Dextran, Hydroxyl Ethyl Starch (HETA), PEG-4000, and gelatin.
3. Surfactants: Non-ionic surfactants are widely used to stabilize proteins, suppress aggregation, and assist in protein refolding. Polysorbate 80 and Polysorbate 20, also known as Tween 80 and Tween 20, respectively, are generally used in mAb therapeutics. Other examples include Brij 35, Triton X-10, Pluronic F127, and Sodium Doceyl Sulfate (SDS).
4. Amino acids: These excipients stabilize proteins by a variety of mechanisms. Examples include Histidine, Arginine, and Glycine. Other amino acids used as formulation excipients include Methionine, Proline, Lysine, Glutamic acid, and Arginine mixtures.
5. Preservatives: These compounds are included in formulations to prevent microbial growth. Examples include Benzyl alcohol, m-Cresol, and Phenol.

The biological material used in the present disclosure is obtained from outside India.

Rationale for Targeting Specific Genomic Sequence in FUT 8 Locus

FUT8 is comprised of three domains, an N-terminal coiled-coil domain, a catalytic domain, and a C-terminal SH3 domain.

Fut8 protein structure is studied extensively to understand the functional domain of the enzyme amino acid sequence. Three dimensional crystal structure of FUT8 enzyme revealed 15 strands and 16 helices. There are at least three regions, N terminus (residues 68-107), C-terminus (573-575) and residues 368-372 which are disordered.

The putative catalytic domain of the FUT8 enzyme is consisted of two domains, an open sheet alpha/beta domain and the Rossmann fold widely known for nucleotide binding region. The alpha/beta domain consisted of five helices and three beta strands, which are alpha 4, 3H1, 3H2, 3H3, beta 1, beta 2 and beta3 strands. The domain is located in the N terminus of the protein sequence. There is no clear evidence how the N terminus catalytic domain is responsible for enzyme functionality.

The Rossmann fold is located downstream at residue 359-492 and contains several alpha helix and beta strands. A series of residues Arg 365, Arg 366, Asp-368, Lys-369, Glu-373, Tyr-382, Asp-409, Asp-410, Asp-453, and Ser-469 play an important role in catalytic domain of FUT8 enzyme.

Ten amino acid residues, Arg 365, Arg 366, Asp-368, Lys-369, Glu-373, Tyr-382, Asp-409, Asp-410, Asp-453, and Ser-469 of human FLITS enzyme protein are conserved among various species, including vertebrates, insectnematode and ascidian.

Rationale for Targeting FUT8 Genes in CHO S Cell Line

Fucose knock out platform is useful to achieve non fucosylated monoclonal antibody molecule. In many instances, developing completely non-fucosylated antibody is a preferred outcome and therefore strategies are made in this disclosure to create complete knock out of Fucose biosynthetic pathway genes.

Fut8 enzyme functions downstream of GDP-Fucose biosynthesis step and is the last enzymatic step for fucosylation of cellular proteins in golgi. Fucosylation precursors from both de novo and salvage pathway use FUT8 enzyme for final fucose moiety transfer. Therefore, knocking out Fut8 gene essentially stops both de novo and salvage pathway of cellular protein fucosylation. This approach results in 100% defucosylation of proteins, including monoclonal antibodies produced in the Fut8 knock out cell line.

The CRISPR/Cas target sequences are targeted in this region. Fut 8 exon7 genomic locus, respective amino acid sequence and position of important structural motifs and CRISPR target locations are depicted in FIG. 1B.

This targeting is not a random selection, but has been arrived at, in the present disclosure, by experimentation to determine the highly specific location on the gene or enzyme, the disruption of which ensures that partial fucosylation that is caused by truncated or partially functional enzyme is avoided.

The Rossmann fold on the other hand, is located downstream at residue 359-492 and contains several alpha helix and beta strands. A series of residues Arg 365, Arg 366, Asp-368, Lys-369, Glu-373, Tyr-382, Asp-409, Asp-410, Asp-453, and Ser-469 play an important role in catalytic domain of FUT8 enzyme.

Thus, targeting the region equivalent to the active site of the enzyme ensures complete disruption of the Fut8 gene and provides efficacious results in comparison to either a technique that is unable to target a precise location on the Fut8 gene or a technique that targets another location on the Fut8 gene, which might result in partial disruption of Fut8 gene and enzyme activity. A cell with partially functional fucosylated machinery produces partially fucosylated proteins, which exhibits lower therapeutic functions as compared to non-fucosylated proteins.

The cells produced by the method of the present disclosure produce completely or 100% non-fucosylated proteins, including 100% non-fucosylated antibodies.

The present disclosure introduces mutations at critical amino acid positions at the catalytic site of the FUT8 codon sequence through CRISPR/Cas complex. The CRISPR design is aimed to primarily target the N-terminal catalytic domain, specifically the beta 2 strand and the 3H2 helix region by incorporating single stranded breaks. The cellular DNA repair system introduces nucleotide changes while carrying out the single stand break repair and creates non-functional FUT8 enzyme.

The CRISPR system is well known for deletion and insertion in a localized manner and therefore creates frameshift mutation at the targeted exon7 and inserts stop codons. Introduction of stop codons ensures premature translation termination and the downstream Rossmann fold is excluded from enzyme structure, resulting in non-functional FUT8 enzyme.

In an embodiment of the present disclosure, the subsequent genomic DNA analysis of the modified CHO-S cell lines reveals deletion, insertion, stop codon as well as frame shift mutations. Thus, the present disclosure envisages disruption of Fut8 gene and Fucosyltransferase enzyme by targeting amino acid positions in the beta 2 strand and the 3H2 helix through deletions, insertions and/or frame shift mutations.

The resulting clones may result in premature translation stop, therefore causing extensive changes in critical downstream sequences such as Arg-365, Arg-366, Asp-368, Lys-369, Glu-373, Tyr-382, Asp-409, Asp-410, Asp-453, Ser-469 and combinations thereof.

In the present disclosure, the FUT8 amino acid sequence from CHO-S genomic database is analyzed and it is confirmed that these critical amino acids are conserved in the FUT8 gene derived from CHO-S cell line as well. Sequence specific CRISPR/Cas complex is designed, targeting gene sequences upstream of these amino acid motifs to introduce genomic modifications. It is analysed how altering amino acid sequences upstream of the critical FUT8 enzyme catalytic domain disrupts the enzyme function.

It is stated that mutation of these critical amino acids provides complete disruption of FUT8 gene functionality. Gene targeting using CRISPR/Cas technology is a novel approach to create a Fucose knock out cell line platform. CRISPR/Cas transfected cells are screened through FUT8 gene functionality assays. Selected clones are confirmed through sequencing of genomic FUT8 loci for mutations. The mutant fucose knock out CHO-S cell line is then used for expressing non-fucosylated therapeutic proteins, including non-fucosylated therapeutic monoclonal antibodies or part of antibody.

CRISPR/Cas constructs specifically targeting the amino acid codon sequences in genomic locations are designed, and cloned in expression vectors, for e.g. pD1401 or pD1301 depending on the type of Cas9 gene. The CRISPR/Cas complex is transiently transfected in CHO-S cells; the cells are plated in 96 well plates for single colony generation. Each clone is then screened for fucosylation of cellular proteins using fluorescence based *Lens Culinaris* Agglutinin assay (LCA). Clones positive for FUT8 gene disruption are further tested through enzymatic assays and kinetic analysis of mutant alleles of FUT8 gene. Finally, the genomic sequence at the FUT8 loci is analyzed for any mutation carried out through CRISPR/Cas. These mutations involve deletions or insertions, thereby introducing frame shift mutations of the FUT8 codon sequence, and rendering the sequence disrupted and the enzymes non-functional.

The fucose knock out Anti Her2 antibody expressing cell line obtained from the method of the present disclosure is used as a cell line for expressing afucosylated anti Her2 antibody product for therapeutic purposes, and any other uses. The method has been used to develop afucosylated Antiher2 antibody product.

Any CHO cell line which produces Anti Her2 Antibody at a higher titer is selected as the starting cell line. The said cell line is transfected with the CRISPR-Cas complex against FUT8 gene and is selected for afucosylation through fluorescence based *Lens Culinaris* Agglutinin assay. Clonal cell lines positive for fluorescence based *Lens Culinaris* Agglutinin assay are developed and used for expression of afucosylated AntiHer2 antibody product.

The present disclosure describes the characterization of completely Afucosylated Anti Her2 antibody product and its biological significance. The present disclosure describes significant improvement of the Afucosylated AntiHer2 antibody interaction with FcγRIII receptor compared to innovator Trastuzumab molecule. The corresponding Antibody Dependent Cellular Cytotoxicity (ADCC) assay clearly established the improved efficacy of the afucosylated AntiHer2 Antibody. This improvement has translated to more than 9 fold cytotoxicity of Her2 overexpressing breast cancer cell lines compared to Trastuzumab. The results are significant improvement as this Afucosylated AntiHer2 antibody product is more efficacious in breast cancer treatment in patients.

The Afucosylated AntiHer2 antibody therefore represents a more efficious molecule for improved treatment options for breast cancer patients in terms of—

1. Treatment option at earlier stages of breast cancer patients—the Afucosylated AntiHer2 antibody product is usable in cancer patients with tumors expressing lower levels of tumor antigen, in this case Her2 antigens.
2. Treatment options with lower doses of the drug—the Afucosylated AntiHer2 antibody product is usable at a lower doses for effective treatment of breast cancer patients
3. Treatment options with lesser harmful side effects with this drug—The Afucosylated AntiHer2 antibody product requires less dosage for effective treatment of breast cancer patients and therefore produces lesser harmful side effects.
4. Treatment options with lower immunogenicity effects with this drug—The Afucosylated AntiHer2 antibody product is structurally exactly similar with that the innovator Trastuzumab product except that the Afucosylated AntiHer2 antibody product does not have any Fucose at the glycan chain. The Afucosylated AntiHer2 antibody product is usable used at a lower dosage and therefore the product causes lower immunogenicity.
5. Treatment options with lower cost of treatment—Treatment with Afucosylated AntiHer2 antibody product requires much lesser dosage compared to Trastuzumab. Therefore, this product brings down the cost of treatment per patient.

The present disclosure is further described with reference to the following examples, which are only illustrative in nature and should not be construed to limit the scope of the present disclosure in any manner.

Reagent Preparation

Advanced DMEM Complete Growth Medium—500 ml 1. 50 ml FBS (final concentration 10%) is added to the upper chamber of the 500 ml filter unit.
2. 10 ml of 200 mM Glutamine (final concentration 4 mM) is added.
3. 5 ml of 100× Pen-Strep solution (final concentration 1×) is added.
4. The volume is adjusted up to 500 ml with advanced DMEM medium.
5. The complete medium is filtered through 0.22 μm filter.
6. The upper chamber is dismantled and the reservoir or media bottle is closed.
7. The medium can be used within 30 days of preparation.
8. The medium is stored at 2° C. to 8° C. and away from continuous exposure to light.
9. In cases where LCA selection medium is prepared, 10 ml of 10 mg/ml stock LCA reagent is mixed with 500 ml of prepared DMEM medium to achieve final 200 μg/ml LCA concentration in DMEM medium.

Reagent Preparation

1. Power CHO-2 CD complete growth medium—500 ml is taken.
2. 10 ml of 200 mM Glutamine (final concentration 4 mM) is added to the upper chamber of the 500 ml filter unit.
3. 5 ml of 100× Pen-strep solution (final concentration 1×) is added.
4. The volume is adjusted to up to 500 ml with Power CHO-2 CD media.
5. The complete media is filtered through 0.22 μm filter.
6. The upper chamber is dismantled and the reservoir or media bottle is closed.
7. The media can be used within 30 days of preparation.
8. It is stored at 2°-8° C. and away from continuous exposure to light.

Materials & Equipment
1. Bio safety cabinet
2. Sorvall ST 16R centrifuge
3. Water bath
4. Inverted phase contrast microscope
5. Millipore GUAVA 8HT easyCyte benchtop flowcytometer
6. Vi-cell XR cell viability analyser
7. Hemocytometer
8. Refrigerator
9. Eppendorf minispin centrifuge
10. Micropipettes
11. Micro tips
12. 96 well tissue culture plates
13. 12 well tissue culture plates
14. 6 well tissue culture plates
15. Serological pipettes (10 ml, 25 ml and 50 ml)
16. 1000 ml filtration unit—0.22 µm pore size
17. 70% ethanol
18. Advanced DMEM
19. DPBS
20. Fetal Bovine Serum
21. Penstrep
22. Glutamine
23. 0.05% Trypsin EDTA
24. 0.4% Trypan blue
25. Microfuge tubes (1.5 ml and 2 ml)
26. Falcon tubes (15 ml and 50 ml)
27. Bovine serum albumin fraction V
28. Fluorescein lens culinaris agglutinin (LCA-FITC)
29. Fluorescein streptavidin (Strep-FITC)

TABLE 1

Reagents used in this disclosure

| S. No. | Reagent | Composition |
|---|---|---|
| 1 | Agarose | Agarose (SIGMA, Cat-A9539) |
| 2 | 1 kb DNA ladder | 1 kb ladder (Thermoscientific Cat-SM0311) |
| 3 | 100 bp DNA ladder | 100 bp ladder (Thermoscientific, Cat-SM0322) |
| 4 | QIAGEN genomic DNA isolation kit | DNeasy Blood & Tissue Kit (QIAGEN, Cat-69504) |
| 5 | Taq DNA polymerase | Taq DNA polymerase with thermopol (NEB, Cat-M0267 & M0273L) |
| 6 | Phusion high-fidelity DNA polymerase | Phusion high-fidelity DNA polymerase (Thermo Scientific, Cat-F530L) |
| 7 | InsTAclone PCR cloning | TA cloning vector pTZ57R/T (Thermo Scientific, Cat-K1214) |
| 8 | Competent cells DH10B cells | Max Efficiency DH10B competent cells (Invitrogen, Cat-18297-010) |
| 9 | Competent cells DH5alpha cells | NEB 5-alpha competent cells (NEB, Cat-C2987P) |
| 10 | Ethanol absolute (99.9%) | Sdfine chem, Cat-58051 L05 |
| 11 | Plasmid DNA isolation | QiaPrep spin miniprep Kit (QIAGEN, Cat-27104) |
| 12 | DNA elution kit | QIAGEN Gel Extraction kit (Cat-20021 and 20051) |
| 13 | Restriction enzymes | EcoRI-HF (NEB, Cat-R3101) Hind III-HF (NEB, Cat-R3104) |
| 14 | T4 ligase | T4 DNA Ligase (NEB, Cat-M0202) |

TABLE 2

Media and buffers used in this disclosure

| S. No. | Media/Buffers | Composition |
|---|---|---|
| 1 | 6X loading DNA dye | Sucrose-4 g, Bromophenol blue - 0.025 g, made up to 10 mL using purified water. |
| 3 | 50X TAE buffer | Tris base-121 g, Glacial acetic acid - 28.6 mL, EDTA (0.5M) pH-8 - 50 mL, made up to a volume of 500 mL with purified water. |

Example 1: Designing of CRISPR/Cas Constructs

The objective of this example is to design CRISPR/Cas complex for specific inactivation of FUT8 allele.

1.1—CRISPR Constructs

CRISPR is based on a class of RNA-guided endonucleases known as Cas9 from the microbial adaptive immune system found in Streptococcus pyogenes. Cas9 nuclease is directed to specific sites on the genome by guide RNAs (gRNAs). The Cas9/gRNA complex binds to a 20 bp target sequence that is followed by a 3 bp Protospacer Activation Motif (PAM) NGG or NAG on the specific gene that needs to be edited (Jinek, 2012; Mali, 2013). Thus, the binding of this whole complex creates Double Stranded Breaks (DSBs).

A crucial step in targeted genome editing at genomic loci that need to be modified, is the introduction of these DSBs. Once, DSBs are introduced, they are repaired either by non-homologous end joining (NHEJ) or homology directed repair (HDR).

NHEJ is known for the efficient introduction of insertion/deletion mutations (indels) that in turn cause disruption of the translational reading frame of the target coding sequence or at binding sites of trans-acting factors in promoters or enhancers. On the other hand, HDR mediated repair can insert specific point mutations or sequences at the target locus. Thus, co-transfection of cell types with vectors that express the Cas9 nuclease and the gRNAs targeted to a specific gene locus can efficiently knock down the expression of target genes. The expected frequency of mutations at these specific sites ranges from >1% to 50% (Sander 2014).

Selection of mutants is performed by simple screening using sequencing, without the use of drug resistance marker selection. In order to increase the specificity of gene disruption, the present disclosure uses mutant Cas9 (D10A) that is guided by two guide RNAs for a single gene locus and that introduces two single stranded breaks or nicks. This also reduces the chances of non-specific binding at other random sites. A vector encoding Cas9-D10A and the 2 gRNAs are used to cause efficient gene knock-out.

The Fut8 genomic loci is targeted for sequence specific deletions through CRISPR/CAS9 technology and generate defucosylated mammalian expression systems.

Figure 1A:
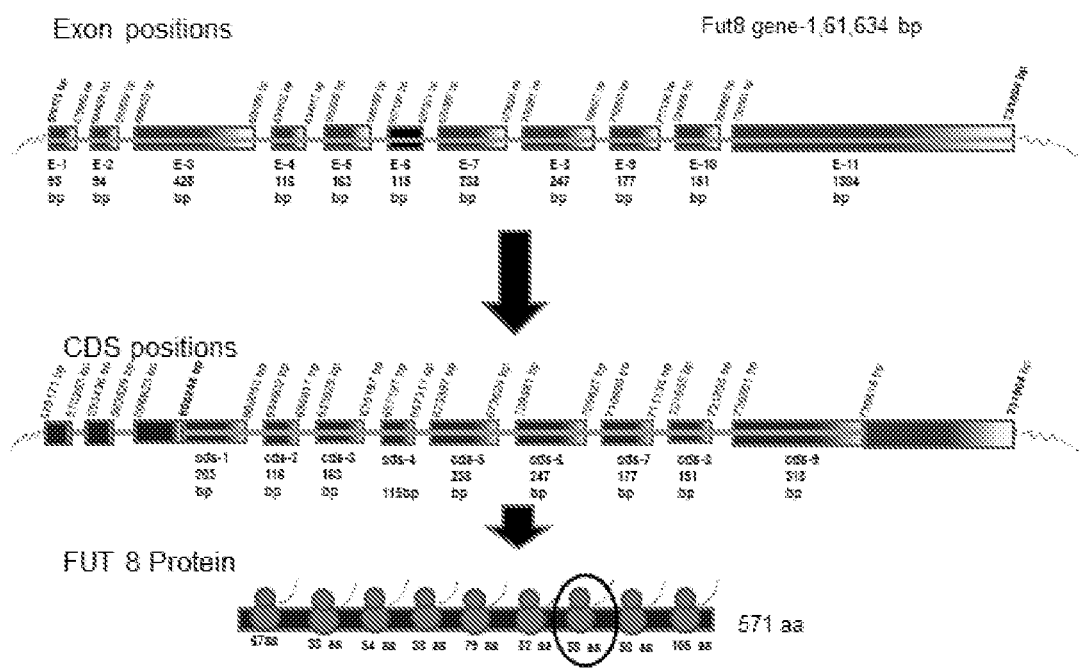
FIG. 1A depicts Fut8 gene genome organization.
Figure 1B:
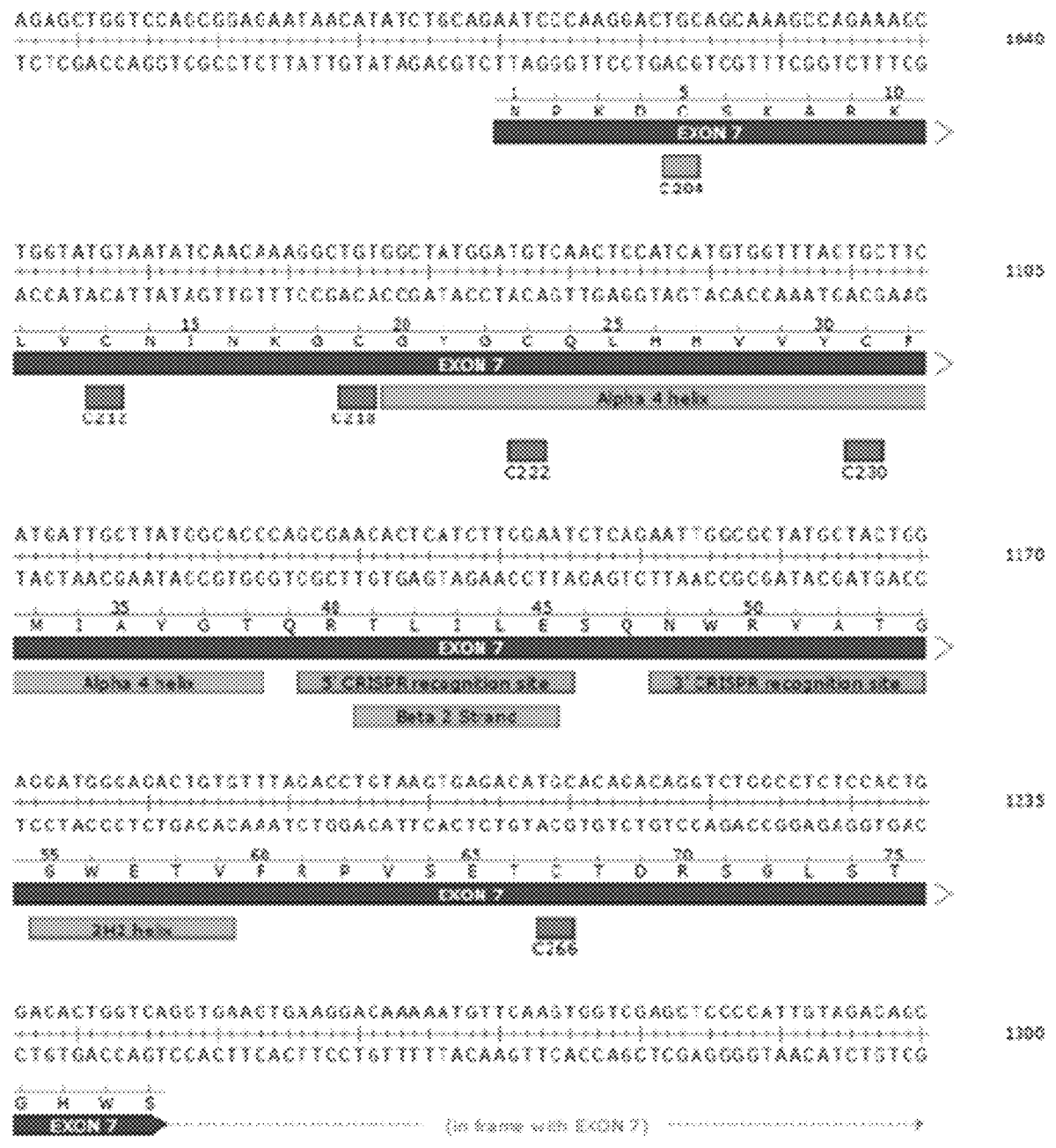

FIG. 1A of the present disclosure depicts the Fut8 coding sequence and protein sequence. FUT8 genomic sequence is analyzed from database sequence, sequence ID NW 003613860. FUT8 genomic sequence spans from 570171-731804 bases and contains eleven exons depicted as E1 to E11 in the figure. Base pairs locations for each exon are also indicated. E1, E2 and part of E3 constitute un-translated region in the upstream sequence, and part of E11 is also part of un-translated region. Translated regions are described as CDS 1 to CDS 9. Length of each CDS is indicated below the CDS number. CDS1 to CDS9 code for amino acid sequences varying from 38 amino acids to 105 amino acids.

*Cricetulus griseus* or Chinese Hamster fucosyltransferase 8 (Fut8) mRNA (3126 bp) is derived from NCBI Reference Sequence: XM_003501735.1, also represented by SEQ ID No. 1 of the present disclosure.

CAGGTTGCTGCTCTGGCTTAGGCCATCTATGACCCTGGTGGTGTTTTCA

TTCACTATAAGTCCTTCCCATCTTTATTAACTGAGCAAGTTCAGctagt aattttagagaccgaggttcaagcaataacacctatctctgcaataccg tgtggctttcttcaatgtcttacatcctaaggaaaggaagCATGTAGAG

CCCAGGAAGCACAGGACAAGAAAGCTGCCTCCTTGTATCACCAGGAAGA

TCTTTTTGTAAGAGTCATCACAGTATACCAGAGAGACTAATTTTGTCTG

AAGCATCATGTGTTGAAACAACAGAAACTTATTTTCCTGTGTGGCTAAC

TAGAACCAGAGTACAATGTTTCCAATTCTTTGAGCTCCGAGAAGACAGA

AGGGAGTTGAAACTCTGAAAATGCGGGCATGGACTGGTTCCTGGCGTTG

GATTATGCTCATTCTTTTTGCCTGGGGGACCTTATTGTTTTATATAGGT

GGTCATTTGGTTCGAGATAATGACCACCCTGACCATTCTAGCAGAGAAC

TCTCCAAGATTCTTGCAAAGCTGGAGCGCTTAAAACAACAAAATGAAGA

CTTGAGGAGAATGGCTGAGTCTCTCCGaataccagaaggccctattgat caggggacagctacaggaagagtccgtgttttagaagaacagcttgtta aggccaaagaacagattgaaaattacaagaaacaagctaggaatgATCT

GGGAAAGGATCATGAAATCTTAAGGAGGAGGATTGAAAATGGAGCTAAA

GAGCTCTGGTTTTTTCTACAAAGTGAATTGAAGAAATTAAAGAAATTAG

AAGGAAACGAACTCCAAAGACATGCAGATGAAATTCTTTTGGATTTAGG

ACATCATGAAAGgtctatcatgacagatctatactacctcagtcaaaca gatggagcaggtgagtggcgggaaaaagaagccaaagatctgacagagc tggtccagcggagaataacatatctgcagAATCCCAAGGACTGCAGCAA

AGCCAGAAAGCTGGTATGTAATATCAACAAAGGCTGTGGCTATGGATGT

CAACTCCATCATGTGGTTTACTGCTTCATGATTGCTTATGGCACCCAGC

GAACACTCATCTTGGAATCTCAGAATTGGCGCTATGCTACTGGAGGATG

GGAGACTGTGTTTAGACCTGTAAGTGAGACATGCACAGACAGGTCTGGC

CTCTCCACTGGACACTGGTCAGgtgaagtgaaggacaaaaatgttcaag tggtcgagctcccattgtagacagcctccatcctcgtcctccttactt accttggctgtaccagaagaccttgcagatcgactcctgagagtccat ggtgatcctgcagtgtggtgggtatcccagtttgtcaaatacttgatcc gtccacaaccttggctggaaagggaaatagaagaaaccaccaagaagct tggcttcaaacatccagttattggAGTCCATGTCAGACGCACTGACAAA

GTGGGAACAGAAGCAGCCTTCCATCCCATTGAGGAATACATGGTACACG

TTGAAGAACATTTTCAGCTTCTCGAACGCAGAATGAAAGTGGATAAAAA

AAGAGTGTATCTGGCCACTGATGACCCTTCTTTGTTAAAGGAGGCAAAG

ACAAAgtactccaattatgaatttattagtgataactctatttcttggt cagctggactacacaaccgatacacagaaaattcacttcggggcgtgat cctggatatacactttctctcccaggctgacttccttgtgtgtactttt tcatcccagGTCTGTAGGGTTGCTTATGAAATCATGCAAACACTGCATC

CTGATGCCTCTGCAAACTTCCATTCTTTAGATGACATCTACTATTTTGG

AGGCCAAAATGCCCACAACCAGATTGCAGTTTATCCTCACCAACCTCGA

ACTAAAGAGGAAATCCCCATGGAACCTGGAGATATCATTGGTGTGGCTG

GAAACCATTGGAATGGTTACTCTAAAGGTGTCAACAGAAAACTAGGAAA

AACAGGCCTGTACCCTTCCTACAAAGTCCGAGAGAAGATAGAAACAGTC

AAATACCCTACATATCCTGAAGCTGAAAAATAGAGATGGAGTGTAAGAG

ATTAACAACAGAATTTAGTTCAGACCATCTCAGCCAAGCAGAAGACCCA

GACTAACATATGGTTCATTGACAGACATGCTCCGCACCAAGAGCAAGTG

GGAACCCTCAGATGCTGCACTGGTGGAACGCCTCTTTGTGAAGGGCTGC

TGTGCCCTCAAGCCCATGCACAGTAAAATAATGTACTCACACATAACAT

ACAAATGGATTATTTTCTACTTTGCCCTTTAAATATTCTGTCCCCATGA

AACAAACACTGCCACATTATGTAATTTAAGTGACACAGACGTTTTGTGT

GAGACTTCAAACATGGTGCCTATATCTGAGAGACCTCTGTGATTTACTG

AGAAGATGAGAACAGCTCCCTTCTGTGGGGAAGTTGGTTCTTAGTCAGT

GGTGGACTGGCCACTGAATTCACTGCAATCAACAGATTCAGAATGAGAA

TGGATGTTTTTCCTTTATATGGTTGTCTGGATTTTTTTTAAAGTAATTT

CATCAGTTCAGTTCATCCACCTCATTAATAAATGAAGGAATATACCAAT

AAAATCAAATGAAATATTCACTGTCCATTAGGAAGTTTTATAAAACAAT

GCCATGAACAAAAAATTCTTTAGTACTCAATGTTTCTGGACATTCTCTT

TGATAACAAAAATAAATTTTAAAAAGGAATTTTGTAAAGTTTCTGGGAT

TCTGTATCACTGGATGATGTAGTTATAAGCTTTGTAGTAGAAATATGGG

AAGTGGGTTTATAGCTTTTAAGATTTTTTTCTACTTTTGTCCTACTTTT

TCTATTTCTGATAGAATAATCATATTTCAAGAGAAGCATTGGTCCCCTC

TAATACTAGTAACTGCCTTTAGTCATGCATATTATATGAAGTTGCTAAG

AACACGCTTTGGGGGAGGTGTTCACTCTCTTAGTTTGATATTGTTGACT

TGATATAATTGAATGAAATAGTCATTCTCTTGCTTCCAG

Alternative exons are represented in upper and lower case letters

Fut8 protein structure is studied extensively to understand the functional domain of the enzyme. Three dimensional crystal structure of FUT8 enzyme revealed 15 strands and 16 helices.

Amino acid sequence of FUT8 gene is provided in FIG. 2.

The CRISPR/Cas binding regions are designed in such a way that the specificity of site recognition is high and at the same time the CRISPR/Cas complex carries out the intended DNA single strand break.

In an embodiment, Cas9n (D10A mutant of Cas9 endonuclease) is used for the CRISPR/Cas complex. The Cas9n endonuclease causes single strand DNA break. The two CRISPR recognition sites (5' recognition site and 3' recognition site are spaced at 5 base pair distance, allowing two single stand breaks at close proximity. The resulting breaks allow the NHEJ process of DNA break repair and that introduces mutations in this region.

The CRISPR construct has two unique 20 basepair CRISPR recognition sequences flanked by gRNA scaffolds in tandem with U6 promoter elements for efficient expression of the gRNA sequences. The unique design allows one single vector to express two separate gRNA scaffolds and two unique CRISPR recognition sequences on the genomic DNA.

The nucleotide sequence of wild type Cas9 gene is provided in Seq ID No. 2.

The nucleotide sequence of the Cas9n endonuclease is provided in Seq ID No. 3.

The CRISPR/Cas design is uniquely positioned to target beta 2 strand and the 3H2 helix region by incorporating single stranded breaks. The design is compatible with two single strand breaks at close proximity, thereby imparting higher specificity of target recognition as NHEJ repair mechanism occurs only at these targeted genomic locations. Nonspecific single stand breaks, if created are usually repaired by homologous recombination which is accurate and rarely creates any mutation.

The primary target of the present disclosure is to create mutations at the N-terminal catalytic domain, the beta 2 strand and 3H2 helix. Insertion and deletions through CRISPR/Cas at this location makes the FUT8 enzyme non-functional. In addition, frame shift mutations also cause premature translation stop codons, the Rossmann fold which is downstream of this region does not express then. Amino acid residues at Rossmann fold such as Arg 365, Arg 366, Asp-368, Lys-369, Glu-373, Tyr-382, Asp-409, Asp-410, Asp-453, and Ser-469 are very important for FUT8 functionality. The truncated enzyme is non-functional and leads to Fucose Knock out cell line.

FIG. 2 of the present disclosure depicts the CHO-S Fut8 amino-acid sequence. Complete amino acid sequence of FUT8 gene is provided. Amino acid sequence from each CDS is indicated with large arrowheads. Small arrows indicate critical amino acids present in Exon 7 (CDS5) which are targeted in the Fut8 gene by CRISPR constructs.

The CHO whole cell genome shotgun sequencing data with accession number NW_003613860 for the Fut8 gene corresponds to a total of 161634 bp. The Pubmed accession number for the coding region or mRNA of the Fut8 gene is XM 003501735.1. The mRNA sequence, as shown in FIG. 1A, encompasses the complete coding sequence for expression of the FUT8 gene product, which is α-1,6 fucosyltransferase.

The Spidey alignment tool (http://www.ncbi.nlm.nih.gov/spidey/spideyweb.cgi) is used to identify the exons in the genomic DNA by aligning the mRNA sequence with the genomic DNA sequence. A total of 11 exons with the boundaries as shown in Table 3 are identified.

TABLE 3

Characterization of Fut8 mRNA

| EXON | Genomic coordinates | mRNA coordinates | Length (nucleotides) |
|---|---|---|---|
| Exon 1 | 570171-570263 | 1-93 | 93 |
| Exon 2 | 593436-593529 | 94-187 | 94 |
| Exon 3 | 608623-609050 | 188-615 | 428 |
| Exon 4 | 634802-634917 | 616-731 | 116 |
| Exon 5 | 635025-635187 | 732-894 | 163 |
| Exon 6 | 657197-657311 | 895-1009 | 115 |
| Exon 7 | 673387-673624 | 1010-1247 | 238 |
| Exon 8 | 709381-709627 | 1248-1494 | 247 |
| Exon 9 | 710960-711136 | 1495-1671 | 177 |
| Exon 10 | 721655-721805 | 1672-1822 | 151 |
| Exon 11 | 730501-731804 | 1823-3126 | 1304 |

FUT8 enzyme functionalities through site directed mutagenesis studies of critically important amino acid residues in the catalytic domain has been confirmed.

A 100% identity between the genomic DNA and mRNA sequence is observed. Organization of the Fut8 gene showing all the 11 exons and position of the gRNAs targeting exon7 is shown in FIG. 1A of the present disclosure. The construct with mutant Cas9 nuclease (Cas9n) is designed, which creates single strand break (nick) at the target site. Two separate gRNAs are designed at close proximity in exon7 to create two nicks for eventual DNA repair.

In the present disclosure, CRISPR/Cas9 technology target sites are localized to the first few exons of the Fut8 gene. This is done to avoid partial fucosylation that can be caused by truncated or partially functional enzyme.

Exon-7 (CDS-5) nucleotide sequence of Fut8 is represented by SEQ ID No. 4 of the present disclosure.

```
AATCCCAAGGACTGCAGCAAAGCCAGAAAGCTGGTATGTAATATCAACA

AAGGCTGTGGCTATGGATGTCAACTCCATCATGTGGTTTACTGCTTCAT

GATTGCTTATGGCACCCAGCGAACACTCATCTTGGAATCTCAGAATTGG

CGCTATGCTACTGGAGGATGGGAGACTGTGTTTAGACCTGTAAGTGAGA

CATGCACAGACAGGTCTGGCCTCTCCACTGGACACTGGTCAG
```

Exon-7 (CDS-5) amino acid sequence of Fut8 of CHO cell is represented by SEQ ID No. 5 of the present disclosure. The targeted amino acid positions in the protein/peptide sequence are underlined.

```
NPKDCSKARKLVCNINKGCGYGCQLHHVVYCFMIAYGTQRTLILESQNW
RYATGGWETVFRPVSETCTDRSGLSTGHWS
```

1.2—Sequence of Interest in Fut8 Gene to be Targeted Using CRISPR

In Exon 7 of the Fut8 gene, the sequences provided below are used to bind to CRISPR-Cas complex.

```
CRISPR recognition sequence 1 on Fut8 gene is
represented by SEQ ID No. 6-
AATTGGCGCTATGCTACTGGAGG gRNA1- is represented by SEQ ID No. -7
AAUUGGCGCUAUGCUACUGGAGG CRISPR recognition sequence 2 on Fut8 gene is
represented by SEQ ID No. -8
CCAGCGAACACTCATCTTGGAAT gRNA2- is represented by SEQ ID No. -9
CCAGCGAACACUCAUCUUGGAAU
```

The target sequence in Fut8 gene that is used in an embodiment of the present method is shown in FIG. 3B of the present disclosure. The sites of cleavage are indicated with an arrow. The distance between the two gRNAs is 5 bases. The gRNA recognition sequence is underlined in FIG. 3B. The corresponding synthesized fragment is incorporated into the pD1401 vector (FIG. 3A) and named as pD1401 gRNA 514-553, the features of which are described subsequently in the disclosure.

This method of the present disclosure uses Cas9n (nickase mutant) in targeting Fut8 genomic sequence, exon 7 with CRISPR/Cas system. The Cas9n endonuclease makes single stand break (SSB) in opposite strand of DNA. The CRISPR/Cas recognition sequences in the upper and lower strands are underlined. Corresponding single strand break sites are indicated as black arrow heads. The three nucleotide PAM sequences are indicated in bold letters.

The CRISPR/Cas vector construct for this design is termed as pD1401 gRNA (514-553).

The 5' and 3' CRISPR recognition sequence is indicated in small and italicized, two separate sites complementary to this recognition sequence are recognized at the FUT8 genomic sequence. The sequence represented with bold letters indicate gRNA scaffold sequence for CRISPR/Cas complex to get engaged.

SEQ ID No. 10- gRNA + scaffold for Fut8 Exon 7
*attccaagatgagtgttcgc*GTTTTAGAGCTAGAAATAGCAAGTTAA

AATAAGGCTAGTCCGTTATCAACTTGAAAAAGTGGCACCGAGTCGGT

GCTTTTTTGCTCCGCGGCACGAGAACTCAAAGCCCCGGGGCCTGGGT

CCCACGCGGGGTCCCTTACCCAGGGTGCCCCGGGCGCTCATTTGCAT

GTCCCACCCAACAGGTAAACCTGACAGGTCATCGCGGCCAGGTACGA

CCTGGCGGTCAGAGCACCAAACATACGAGCCTTGTGATGAGTTCCGT

TGCATGAAATTCTCCCAAAGGCTCCAAGATGGACAGGAAAGGGCGCG

GTTCGGTCACCGTAAGTAGAATAGGTGAAAGACTCCCGTGCCTTATA

AGGCCTGTGGGTGACTTCTTCTCACCG*aattggcgctatgctactgg*

GTTTTAGAGCTAGAAATAGCAAGTTAAAATAAGGCTAGTCCGTTATC

AACTTGAAAAAGTGGCACCGAGTCGGTGC

5' CRISPR recognition sequence in the
synthesized DNA from DNA2.0 or DNA binding
domain 1-
                                        SEQ ID No. 11
ATTCCAAGATGAGTGTTCGC Target specific crRNA sequence (5' to 3' direction)- Seq ID No. 12
AUUCCAAGAUGAGUGUUCGC 3' CRISPR recognition sequence in the
synthesized DNA from DNA2.0 or DNA binding
domain 2-
                                        SEQ ID No. 13
AATTGGCGCTATGCTACTGG Target specific crRNA sequence (5' to 3' direction)-
                                        Seq ID No. 14
AAUUGGCGCUAUGCUACUGG gRNA scaffold from DNA2.0-
                                        SEQ ID NO. 15
GTTTTAGAGCTAGAAATAGCAAGTTAAAATAAGGCTAGTCCGTTATC
AACTTGAAAAAGTGGCACCGAGTCGGTGC The construct map is provided in FIG. 3A and important sequence regions are marked.

1.3—CRISPR/Cas Complex Synthesis

Two components must be introduced and/or expressed in cells or an organism to perform CRISPR based genome editing: the Cas9 nuclease; and a 'guide RNA' (gRNA).

A twenty nucleotides long recognition sequence at the 5' end of the gRNA directs Cas9 to a specific target DNA site using standard RNA-DNA complementarity base pairing rules. These target sites must lie immediately 5' of a PAM sequence that matches the canonical form 5-NGG.

A mutant Cas9 nuclease (D10A), known as Cas9n is used to target Fut8 Exon 7 locus, the constructs create single strand breaks instead of a double strand DNA break. This design is aimed to improve specificity of CRISPR/Cas constructs.

In case of single strand breaks, two DNA target sites are targeted at close proximity where single stand break or nicks happen in opposite DNA stands. Thereby, it recruits DNA repair machinery (NHEJ) to repair the DNA damage. Recruiting two gRNA/Cas9n complex at a specific interval to initiate DNA repair improves the specificity to the targeted site. Nonspecific binding of only one of the gRNA/Cas9n complex to unrelated sites causes nicks which are usually repaired through homologous recombination based repair with very low rate of mutation. Therefore, this approach increases the specificity of targeting the Fut8 gene.

Unique regions of FUT 8 gene are targeted based on the enzyme structure information in a way to abolish enzyme catalytic function or by disrupting higher order structure.

The important features of the vectors are:

a) Cas9—a nuclease that is first discovered as a component of the CRISPR system in *Streptococcus pyogenes* and has been adapted for utility in mammalian cells. RNA-guided Cas9 nuclease is able to efficiently introduce precise double-stranded breaks at endogenous genomic loci in mammalian cells with high efficiencies.

b) Cas9-D10A—A D10A mutant of Cas9 nuclease (Cas9n) nicks single strands and combined with a pair of offset guide RNAs complementary to opposite strands of target genomic loci. This helps reduce off-target activity seen with wild type Cas9.

c) Chimeric gRNA scaffold—The chimeric guide RNA (gRNA) scaffold consists of a 20-nucleotide target specific complementary region, a 42-nucleotide Cas9-binding RNA structure and a 40-nucleotide transcription terminator derived from *S. pyogenes* that directs Cas9 nuclease to the target site for genome modification. In this case there are two gRNA scaffolds, one for each gRNA.

d) Kanamycin-r—An effective bacteriocidal agent that inhibits ribosomal translocation thereby causing miscoding. The gene coding for kanamycin resistance is Neomycin phosphotransferase II (NPT II/Neo). *E. coli* transformed with plasmid containing the kanamycin resistance gene can grow on media containing 25 µg/ml kanamycin.

e) P_CMV—The CMV promoter is a constitutive mammalian promoter and mediates strong expression in various cellular systems.

f) P_hU6.1—human A type 3 core promoter for RNA expression.

1.4—the Complete Process of Obtaining CRISPR Construct is Composed of the Following Steps:

1. CRISPR target designing.
2. Vector constructions with vector backbone, namely pD1401 vector with gRNA insert.
3. Transformation of CRISPR constructs pD1401 (gRNA 514-553), into *E coli* competent cells (DH10B or DH5alpha) and plating on LB (Luria Bertani)-Agar supplemented with kanamycin.
4. Inoculation of transformed cells (with CRISPR constructs) into LB broth with Kanamycin.
5. Isolation of Plasmid DNA pD1401 (gRNA 514-553 from DH10B or DH5alpha cells.
6. Transfection of CHO-S cells; screening and selection by LCA assay.
7. Genomic DNA isolation of selected clones using QIAGEN DNeasy Blood & Tissue Kit.
8. Quantification by Spectrophotometry.
9. Optimization of PCR Condition.
10. Cross checking the Genomic DNA sample by PCR,
11. Electrophoresis on agarose gel.
12. PCR amplification using Phusion polymerase and tailing using Taq polymerase.

13. PCR product gel elution using QIAGEN kit.
14. TA cloning using pTZ57R/T vector.
15. Transformation of ligated sample pTZ57R/T+CRISPR (PCR) in DH10B or D1-5alpha cells.
16. Inoculation of transformed cells (pTZ57R/T+CRISPR (PCR)) into LB with Ampicillin broth.
17. Isolation of plasmid DNA (pTZ57R/T+CRISPR (PCR) from DH5alpha and DH10B cells using QIAGEN plasmid DNA isolation kit.
18. Cross checking for the presence of insert by restriction digestion.
19. Sequencing primers; and
20. Confirmation of the INDELs by sequencing.

Example 2: Cho-S Cell Line Expressing High Titer of Antiher2 Antibody

The monoclonal antibody product could be produced in any Chinese Hamster ovary cell line using any technology. Examples for such technologies include but not are restricted to GPEx™, UCOE™, SURE™ technology, Light Path™ technology and many others. In this particular example, the anti Her2 antibody gene is expressed in Chinese Hamster Ovary (CHO-S) cell line utilizing the GPEx technology. GPEx® is based on a highly efficient retroviral vector that transfects 100% of target cells. The advantage of GPEx® is Single integration site for each copy of the vector
No selection marker required
Anti Her2 antibody heavy and light chain protein sequences are obtained from open-access public sources. The corresponding heavy and light chain gene sequences are codon-optimized using proprietary codon-enhancement system. The codon-optimized sequences for antibody heavy and light chain genes are synthesized by commercial vendor and cloned in pUC57 vector. The heavy and light chain sequences are represented by SEQ ID Nos. 16 and 17.

The heavy chain amino acid sequence of Anti-her2 antibody—SEQ ID No. 16

```
MGWSCIILFLVATATGVHSEVQLVESGGGLVQPGGSLRLSCAASGEN

IKDTYIHWVRQAPGKGLEWVARTYPTNGYTRYADSVKGRFTISADTS

KNTAYLQMNSLRAEDTAVYYCSRWGGDGFYAMDYWGQGTLVTVSSAS

TKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDK

KVEPKSCDKTHTCPPCPAPELLGGPSVFLEPPKPKDTLMISRTPEVT

CVVVDVSHEDPEVKFNWYVDGVEVHNAKTKPREEQYNSTYRVVSVLT

VLHQDWLNGKEYKCKVSNKALPAPIEKTISKAKGQPREPQVYTLPPS

REEMTKNQVSLTCLVKGFYPSDIAVEWESNGQPENNYKTTPPVLDSD

GSFFLYSKLTVDKSRWQQGNVFSCSVMHEALHNHYTQKSLSLSPGK.
```

The light chain amino acid sequence of Antiher2 antibody—SEQ ID No. 17

```
MGWSCIILFLVATATGVHSDIQMTQSPSSLSASVGDRVTITCRASQD

VNTAVAWYQQKPGKAPKLLIYSASFLYSGVPSRFSGSRSGTDFTLTI

SSLQPEDFATYYCQQHYTTPPTFGQGTKVEIKRTVAAPSVFIFPPSD
```

-continued
```
EQLKSGTASVVCLLNNFYPREAKVQWKVDNALQSGNSQESVTEQDSK

DSTYSLSSTLTLSKADYEKHKVYACEVTHQGLSSPVTKSFNRGEC.
```

Both genes coding DNA sequences (CDS) are synthesized with flanking Hind III and Xho I cloning sites for facilitated cloning. The pUC57 heavy and light chain encoding plasmids are digested with Hind III and Xho I restriction enzymes to isolate the two CDS. Anti Her2 antibody heavy and light chain DNA fragments are cloned into GPEx® plasmid pCS-newMCS-WPRE and digested with the same two enzymes for retroviral vector based expression. The new plasmid encoding full-length AntiHer2 antibody light chain CDS is named pCS-HighwayLC-WPRE and the validity of the CDS of both constructs is confirmed by DNA sequencing.

These two retroviral expression vectors are used for development of Anti Her2 antibody expressing producer cell lines. Production cell lines are made by performing multiple rounds of transduction of the Chinese Hamster Ovary (CHO-S) parental cell line with retroviral vector containing Anti Her2 antibody sequences coding for light chain (LC) and heavy chain (HC). Six transductions are performed in all. The pooled populations are seeded into 96-well cell culture plates to establish clonal cell lines that originated from single cells. The clonal cell lines are screened by ELISA for protein titer. The top thirty clones are expanded, tested in triplicate T175 flasks for growth and productivity and are cryopreserved. The top clone is tested for productivity by fed batch analyses in shake flasks.

The AntiHer2 antibody producer cell lines are used for generating afucosylated AntiHer2 antibody using the CRISPR/Cas construct targeting FUT8 gene, specifically Exon 7 of the Fut8 gene, of the parental CHO-S cell line. In this example, one of the high producing clonal cell lines is used for obtaining afucosylated AntiHer2.

Example 3: Transfection of Cells with CRISPR Constructs

This example contains procedure for transfection of CHO S cell line over expressing AntiHer2 Antibody. The CHO S cell line is transfected with the CRISPR/Cas construct targeting the FUT8 gene described in previous section. It also describes the method of selection and confirmation of single cell stable cell lines for developing FUT8 knock out CHO-S cell line over expressing AntiHer2 Antibody using CRISPR/Cas technology, and selection of positive clones by flow-cytometry based functional assay.

3.1—Transfection of CHO Cell Line with CRISPR Construct

This example contains transfection procedure for CHO-S cell line over expressing Anti Her2 antibody with CRISPR constructs. DNA concentration ranging from 0.5 µg to 5 µg are tested for various incubation times for e.g., 4 hrs, 24 hrs and 48 hrs. Liposome and modified liposome mediated transfection reagents are tested for e.g., Lipofectamine 2000, Lipofectamine 3000, Lipofectamine LTX with Plus' reagent, MIRUS TransIT X2, MIRUS TransIT 2020, MIRUS TransIT 293, MIRUS TransIT CHO transfection kit. Multiple DNA to transfection reagent ratios (µg: µl) are also tested. The optimum transfection efficiency is achieved using 1:5 DNA to transfection reagent ratio, 24 hrs incubation and Lipofectamine LTX with Plus™ reagent. Optimization experiments are performed with RFP expressing plasmid DNA.

FIG. 4 depicts transfection efficiency of CHO-S cell line using the method described in the present disclosure. Transfection efficiency is determined using a Green Fluorescent Protein expressing plasmid construct. Number of red fluorescence cells observed after transfection compared to the total number of viable cells determines transfection efficiency of the protocol established. Panel A represents the bright field image and panel B represents the same microscopic field for red channel fluorescence. FIG. 4 provides that CHO S cells transfected with Red Fluorescence protein expressing plasmid revealed high level of transfection efficiency. The method of the present disclosure is thus suitable for suspension cell transfection.

Transfection efficiency is calculated by the following formula:

Transfection efficiency=(Number of *RFP* expressing cells/Total number of cells)*100

Optimized transient transfection efficiency is about 50-70% in the Anti Her2 Antibody expressing CHO-S cell line.

Transfection Protocol:

CHO-S cells are seeded at more than 90% viability and at a density of $2\times10^6$ cells/well in a 6 well tissue culture plate and allowed to adhere for 24 hrs. pD1401 (gRNA 514-553) CRISPR Cas construct is transfected using Lipofectamine LTX with Plus™ reagent. 10 µg of construct is used with 1:5 DNA to transfection reagent ratio. The cells are incubated for 20-24 hrs after transfection. Prior to transfection DNA quantity and quality is estimated by UV spectrophotometry. $A_{260/280}$ value DNA represents quality and protein contamination. The ratio of absorbance at 260 nm and 280 nm is used to assess the purity of DNA. $A_{260/280}>1.8$ is generally accepted as "pure" or good quality DNA. 3-4 µl of DNA sample is placed on the micro cuvette and DNA concentration is estimated using Eppendorf Biophotometer D30 against suitable controls.

TABLE 4

| CRISPR DNA dilution | |
|---|---|
| For n wells | |
| pD1401 (gRNA 514-553) | 10 µg * n |
| Plus ™ reagent | 10 * n |
| Opti MEM Media without serum | Up to 1.5 ml * n |

TABLE 5

| Lipofectamine LTX dilution | |
|---|---|
| Lipofectamine LTX | 15 µl * n |
| Opti MEM Media without serum | Up to 1.5 ml * n |

CRISPR DNA and Lipofectamine LTX solution are diluted, mixed gently and incubated for 5-10 minutes at 20-25° C. DNA and transfection reagent dilutions (3 ml) are mixed and incubated for 20-30 minutes at Room Temperature for complex formation. The media is aspirated from the wells. 3 ml of DNA and transfection reagent complex is added drop wise to the plated cells.

The cells are incubated for 24 hours at 37° C. in a 5% $CO_2$ Incubator. The cells are centrifuged at 1400 rpm for 4 min and the spent media is removed. The pellet is re-suspended in 5-10 ml complete media/125 ml Erlenmeyer shake flask and incubated at 37° C. in a 5% $CO_2$ Incubator. Cell count is taken every 2-3 days and viability is monitored. Fresh media change is given every 2-3 days. RCB (Research Cell Banks) is prepared when cells attain a viability of 95%.

3.2—Single Cell Cloning

Serial Dilution and Plating:

Cells are splitted at a density of $0.25\times10^6$ cells/ml one day prior to cloning. Cell count is taken by Vicell XR automated cell counter and ensured viability more than 90% on the day of plating. Cell suspension is serially diluted to obtain a cell density of 1 cell/well. Dilutions are made at 1:10 ratio in each step. Cells are plated in Power CHO 2CD media with 10% FBS, 4 mM Glutamine, 1× PenStrep and 1× Clona Cell CHO ACF (animal component free) supplement in a non-treated 96 well round bottom plate in 100 µl/well. Plates are scanned under inverted phase contrast microscope to identify single cells. Wells containing single cell are visually confirmed and marked for further monitoring. Wells containing 2 cells and 6 cells are also marked and kept for amplification. The plates are incubated at 37° C. in a 5% $CO_2$ Incubator with 75% relative humidity for 10-15 days.

3.3—Amplification of Clones and Mini-Pools in 24 Well Plate:

After 10-15 days the clones are amplified from one well of 96 well plate to one well of 24 well plate in one ml culture volume. Media used for amplification is Power CHO2 CD with 10% FBS 4 mM Glutamine and 1× PenStrep. The 24 well plates are incubated at 37° C. in a 5% $CO_2$ Incubator with 75% relative humidity for 2-3 days.

3.4—Amplification of Clones and Mini-Pools in 6 Well Plates:

The clones and mini-pools are then amplified from one well of 24 well plate to one well of 6 well plate in 3 ml culture volume. The 6 well plates are incubated at 37° C. in a 5% $CO_2$ Incubator with 75% relative humidity for 4-5 days. Media used for amplification is Power CHO2 CD with 4 mM Glutamine and 1× PenStrep. From this step onwards, FBS free media is used for amplification.

3.5—Screening by Flow Cytometry

LCA-FITC binding profile of respective clones is determined and two 6 cell mini-pools (CR2TMCHO 6A, CR2TMCHO 6B) and two single cell clones (CR2TMCHO 1A, CR2TMCHO 1B) are selected for further studies. The details of LCA-FITC binding assay are described in the below section.

3.6—Amplification of Clones and Mini-Pools in 125 ml Erlenmeyer Shake Flasks

The clones and mini-pools are further amplified into 10 ml culture volume in a flat bottom 125 ml Erlenmeyer shake flask. The flasks are incubated at 37° C. in a 5% $CO_2$ Incubator shaker at 120 rpm with 75% relative humidity for 4-5 days. After that, the clones are amplified to 30 ml culture volume in 125 ml Erlenmeyer shake flasks and incubated at 37° C. in a 5% $CO_2$ Incubator shaker at 120 rpm with 75% relative humidity for 4-5 days. Power CHO2 CD media is used for amplification with 4 mM Glutamine and 1× PenStrep solution. Finally cell count, viability and LCA-FITC binding profile are determined. Cell supernatants are harvested by centrifugation at 1400 rpm for 4 minutes and used for protein A purification and further characterization. Research Cell Banks are prepared and cryopreserved following established protocols.

Example 4: LCA-FITC (*Lens Culinaris* Agglutin-Fluorescein Isothiocyanate) Binding Assay Fluorescein isothio cyanate (FITC) is a flurochrome conjugated to LCA. Therefore, presence of fucosylated proteins on cell membrane of control CHO S cells is recognized by fluorescein conjugated LCA. These cells fluoresce brighter in specific flow cytometer channel. The fluorescence observed is represented as fluorescence unit. The cells where fucose pathway is disrupted, the knockout lines are not able to produce fucosylated cellular proteins and hence the cell membrane proteins are non fucosylated. Testing these cells with Fluorescein-LCA conjugate results in fluorescence comparable to background. Therefore, the Fucose knock out cells fluoresce at a much lower level compared to control CHO S cell line.

Fluorescein Lens Culinary Agglutinin (LCA-FITC) stock 5 mg/ml is diluted to get 2 µg/ml final concentration in assay buffer (DPBS containing 2% BSA). Cells are spun at 1400 rpm for 4 minutes using Eppendorf minispin centrifuge. The media is aspirated and the pellet is re-suspended in 0.25-1 ml of assay buffer containing 2 µg/ml LCA-FITC. CHO S control cells are re-suspended in 0.25-1 ml of assay buffer alone (unstained control) and 0.25-1 ml of assay buffer containing 2 µg/ml LCA-FITC (stained control). All the samples are diluted to get $0.1$-$0.2 \times 10^6$ cells/ml in final assay buffer. The samples are then incubated in dark on ice for 30 minutes. Then each sample is analyzed by BD Accuri C6 benchtop flow cytometer for data acquisition. Data analysis is done using Accuri C6 software.

Fluorescein-streptavidin (Strep-FITC) negative staining is also performed. Fluorescein streptavidin (Strep-FITC) stock 1 mg/ml is diluted to get 2 µg/ml final concentration in assay buffer (DPBS containing 2% BSA). Cells are spun at 1400 rpm for 4 minutes using Eppendorf minispin centrifuge. Media is aspirated and the pellet is re-suspended in assay buffer containing 2 µg/ml Strep-FITC. CHO S control cells are re-suspended in assay buffer alone (unstained control), assay buffer containing 2 µg/ml LCA-FITC (stained control) and assay buffer containing 2 µg/ml Strep-FITC. All the samples are diluted to get $0.1$-$0.2 \times 10^6$ cell/ml in 0.25-1 ml assay buffer. The samples are then incubated in dark on ice for 30 minutes. Then each sample is analyzed by BD Accuri C6 benchtop flow cytometer for data acquisition. Data analysis is done using Accuri C6 software. The fluorescence data is presented in below Table 6.

TABLE 6

| Sample ID | Median RFU |
| --- | --- |
| TMCHO Unstained | 1715.50 |
| TMCHO LCA FITC | 130805.50 |
| CR2TMCHO 6A LCA FITC | 30972.00 |
| CR2TMCHO 6B LCA FITC | 24749.50 |
| CR2TMCHO 1A LCA FITC | 29624.00 |
| CR2TMCHO 1B LCA FITC | 29463.00 |

LCA-FITC Binding Profile of Single Cell Clones and Minipool Populations:

FIGS. 5A and 5B depict the fluorescence shift observed in CHO S cells over expressing AntiHer2 antibody and transfected with CRISPR/Cas system targeting FUT8 gene. The fluorescence shift indicates successful FUT8 gene knock out phenotype in the CHO S cells over expressing Anti Her2 antibody. The samples CR2TMCHO 1A and CR2TMCHO 1B indicate representative single cell clonal cell lines derived from CHO S cells over expressing AntiHer2 antibody transfected with CRISPR/Cas system targeting FUT8 gene. The samples CR2TMCHO 6A and CR2TMCHO 6B indicate representative minipools from cell populations derived from CHO S cells over expressing AntiHer2 antibody transfected with CRISPR/Cas system targeting FUT8 gene.

LCA-FITC Binding Profile of Transfected Pool Over Multiple Passages:

The CHO S cell line expressing Anti Her2 Antibody is transfected with CRISPR/Cas construct and is analyzed for Fucose knock out phenotype. The transfected cell line pools are analyzed for multiple passages to understand the stability of Fucose knock out phenotype.

The data suggests the transfected pools maintains Fucose knock out phenotype over multiple generations (FIG. 6). It is observed that higher than 82% CHO S cells maintained Fucose knock out phenotype. This is an unexpected observation. The observation of maintaining more than 82% fucose knock out phenotype is consistent over multiple generations.

The results indicate that the uniqueness of the CRISPR/Cas system designed and used in this disclosure has the ability to transform large number of cells (more than 82% of cells) to Fucose knock out cells. The uniqueness of the constructs and the unique methods are useful because the methodology and the CRISPR/Cas system are usable in any antibody over-expressing cell line to create a novel Afucosylated antibody product. This is a novel approach to create Afucosylated monoclonal antibody which is much simpler, very rapid and highly robust. This surprising achievement allows this methodology and CRISPR/Cas system to develop novel Afucosylated antibody products against any target antigen.

In comparison, for developing Afucosylated monoclonal antibodies, a special Fucose knock out platform needs to be created and be completely characterized before expressing monoclonal antibody genes in that platform. Processes of developing such Fucose knock out platforms are very complex and time consuming and success rate is quite minimal.

The simplification of this process enables development of Afucosylated monoclonal antibodies in a very short period of time from any CHO S cell line expressing any monoclonal antibody.

Therefore the methodologies described here and the CRISPR/Cas systems designed and developed in this disclosure are considered to be efficacious.

Example 5: Growth Curve Determination for Fut8 Knockout Clones $0.5 \times 10^{\wedge} 6$ cells/ml are seeded in 125 ml Erlenmeyer shake flasks. Viable cell count is performed using Vi-cell XR cell viability analyser on Day 1, 2, 3, and 4. Respective growth curves are generated and depicted in FIG. 7. The data suggested comparable growth curve of the parental CHO S cell line and the Fucose knock out CHO S cell line over-expressing Afucosylated Anti Her2 Antibody. The CRISPR/Cas mediated transformation of the parental CHO S cell line does not affect the growth curve and viability profiles. This data suggests the design of CRISPR/Cas has no harmful effects on cell growth and other cell biology parameters which influence monoclonal antibody production in the transfected cell lines described here.

Example 6: Genomic Sequencing Analysis of the Cho S Cell Lines Over Expressing Antiher2 Antibody Transfected with CRISPR/Cas System Targeting Fut8 Gene CRISPR/Cas transfected CHO S cell lines selected through functional assay, namely LCA-FITC flow cytometry assay are used for genomic sequence analysis. The FUT 8 genomic locus of Chinese Hamster is well reported in literature (NW_003613860) and is used as wild type sequence to understand type of gene modification in each cell line clone. The objective of this example is to analyse genomic DNA sequencing results obtained from CHO S cell lines transfected with CRISPR/Cas system and expressing Afucosylated AntiHer2 antibody product. All cell lines reported here are clonal cell lines and are selected from LCA-FITC flow cytometry assay.

Briefly, the selected clonal cell lines are grown in appropriate growth conditions for genomic DNA isolation, purified genomic DNA is used for PCR amplification using primers flanking the FUT8 target locus, the PCR amplified product is then purified and cloned in a suitable vector using *E. coli* competent cells, resulting ampicillin resistant *E. coli* colonies are selected and cultured, plasmid DNA are isolated from each bacterial clone, approximately 5-10 individual bacterial colonies are tested per clonal cell lines through automated sequencing to understand the type of modification at the FUT8 target genomic locus.

Following reagents and solutions are used to carry out genome sequencing of the selected clones The entire genome sequencing protocol is divided in following four processes
A. Genomic DNA isolation from selected clones
B. PCR strategy to amplify specific genomic locus for each cell line.
C. Cloning of PCR products in sequencing vectors
D. Sequence data analysis and identification of INDELs Genomic DNA Isolation from Selected Clones Clonal CHO S cell lines are grown in Power CHO2 CD media with 4 mM glutamine, 100 units/ml Penicillin and 100 µg/ml Streptomycin in shake flasks with 120 rpm at 37° C. in presence of 5% $CO_2$ and 75% relative humidity in controlled condition incubators. The cell growth is observed every day and viability is monitored. Cells are harvested at greater than 90% viability. On the day of isolation, culture media is removed by centrifuging the cell population. Cells are then mixed with 10 ml of DPBS and centrifuged at 1500 rpm for 5 min. The spent media is removed and cell pellet is resuspended in 10 ml DPBS. Cells are washed again using centrifugation at 1500 rpm for 5 min. DPBS is removed completely by aspiration. The final cell pellet is used for genomic DNA isolation.

Genomic DNA is isolated from CHO S parental cells and CHO S cell lines transfected with CRISPR/Cas system expressing Afucosylated AntiHer2 Antibody and selected through LCA flow cytometry assay. Commercially available QIAGEN gDNA extraction kit is used for isolating genomic DNA following manufacturers protocol.

PCR Strategy Design

Genomic DNA sequence of Chinese Hamster is analysed from publicly available database sequence NW_003613860. FUT8 Exon 7 DNA sequences and partial intron sequence is used for designing PCR strategy to amplify the FUT8 target locus.

Primers are designed based on primer length, PCR product length, GC content, melting temperature and potential homoduplex and heteroduplex formation. Primers are designed flanking the FUT8 target locus as provided below. The amplified PCR product is intended for mutation analysis due to CRISPR mediated SSB and subsequent DNA repair. Following nucleotide sequence represents the region of interest with primer sequences in bold letters.

Fut8 Exon 7 and associated intron sequences used for PCR primer design: SEQ ID NO. 20

<u>aagaaataagctgaatcagctctgac</u>ttattgtgtgattttcaatac ctgtgaccaaaatgagaagttaactccttatatctttatcttatttg tttctctggaagAATCCCAAGGACTGCAGCAAAGCCAGAAAGCTGGT

ATGTAATATCAACAAAGGCTGTGGCTATGGATGTCAACTCCATCATG

TGGTTTACTGCTTCATGATTGCTTATGGCAC<u>CCAGCGAACACTCATC</u>

<u>TTGGAAT</u>CTCAG<u>AATTGGCGCTATGCTACTGGAGG</u>ATGGGAGACTGT

GTTTAGACCTGTAAGTGAGACATGCACAGACAGGTCTGGCCTCTCCA

CTGGACACTGGTCAGgtaaggagcatgtgcaccatgaaagat<u>ctctg</u>

<u>gttaggtcagattagcac</u>

Introns are represented from base 21 to base 106 and from base 345 to base 371 in lower case letters. Exon 7 is represented from base 107 to base 344 in upper case letters. The primer binding sites of Left and Right are underlined.

Primer Design for Identifying the INDEL by PCR

Genomic PCR is performed using QIAGEN gDNA extraction kit using the following primers mentioned in table 7.

TABLE 7

| PCR Sets | Primer Name | Primer sequence (5' to 3') | PCR product size | Base | $T_m$ | %GC |
| --- | --- | --- | --- | --- | --- | --- |
| CRISPR primers at FUT8 Exon 7 | CRP_P1_Fw | AAGAAATAAGCTGAA TCAGCTCTGAC SEQ ID No. 18 | 394 bp | 26 | 55.2 | 38 |
| | CRP_P1_Rv | GTGCTAATCTGACCT AACCAGAG SEQ ID No. 19 | | 23 | 54.7 | 47.8 |

The following section provides experimental details for PCR product generation from CHO S genomic DNA from control cell lines and CHO S clonal cell lines expressing afucosylated AntiHer2 antibody, cloning of PCR products in *E coli* competent cells and sequencing of cloned PCR products.

Optimization of PCR Condition—

The experiments are designed to standardize PCR conditions. The parameters tested include, genomic DNA concentration (from 100 ng to 1000 ng), primer concentrations (2 nmole to 20 nmole), PCR annealing temperature (from 55.8° C. to 62.9° C.) and time (20 secs to 50 secs), PCR product extention time (30 secs to 60 secs) and PCR cycle number is set at 30 cycles. Arrived optimized condition is described in following section.

PCR reactions are carried out using proof reading polymerase Phusion polymerase to ensure that PCR mediated mutations are limited. Following PCR amplification cycles, Taq polymerase enzyme is added in the mix for tailing. The tailing step is important as the extra base added to the PCR products allows direct cloning in sequencing vector described in the next section. In order to add dATP overhangs to PCR product for cloning in TA cloning vector, the Phusion polymerase amplified product is incubated with Taq DNA polymerase for 20 minutes at 72° C.

Cross Checking the Genomic DNA Sample by PCR—

Genomic DNA PCR products are analysed in agarose gel electrophoresis and the product length is confirmed using a molecular weight standard. PCR samples with clear amplification profile are used in the next processing step.

PCR Product Gel Elution Using QIAGEN Kit—

The amplified PCR products are loaded in freshly prepared 1% agarose gel and electrophoresed at 100V for one hour to separate amplified PCR products from unused primers and any other dimers produced during the amplification process. The amplified products are excised from gel and eluted using commercially available Qiagen gel elution kit. DNA is eluted with highly pure molecular biology grade water.

Cloning of PCR Products in Sequencing Vectors—

Agarose gel purified PCR amplified products are then used for cloning in commercially available pTZ57R/T vector through DNA ligation process. Conditions for DNA ligation have been standardized previously.

Transformation of Ligated Sample pTZ57R/T+CRISPR (PCR) in DH5alpha E. coli Competent Cells—

Ligated DNA is transformed in E. coli DH5alpha competent cells, available commercially. Transformation protocol as described by manufacturer is followed to achieve high level transformation efficiency. After transformation, the E. coli cells are grown in presence of Ampicillin antibiotic for growth of transformed colonies.

Inoculation of Transformed Cells (pTZ57R/T+CRISPR (PCR)) into LB Media with Ampicillin—

Each separate colony is inoculated in LB+Ampicillin broth in 5 ml culture volume and grown overnight for plasmid DNA isolation.

Isolation of Plasmid DNA (pTZ57R/T+CRISPR(PCR)) from DH5alpha Transformed Cells—

4.5 ml of overnight grown cultures are used for plasmid DNA isolation using commercially available QIAGEN plasmid DNA isolation kit following manufacturers protocol. The plasmid DNA is eluted with highly pure molecular biology grade water.

Cross Checking of Plasmids for the Presence of Insert—

Each plasmid preparation is tested for presence of insert using suitable restriction enzyme digestion followed by agarose gel electrophoresis. The size of insert is compared with suitable molecular weight standards.

PCR Reaction

First, the double-stranded DNA template is denatured at a high temperature at 94° C. Sequence-specific primers mentioned in the Table 7 are then annealed (60.4° C.) to sites flanking the target sequence. A thermostable DNA polymerase (Phusion polymerase) extends (72° C.) the annealed primers, thereby doubling the amount of the original DNA sequence. This newly synthesized product then becomes an additional template for subsequent cycles of amplification. These three steps are repeated for 30 cycles, resulting in a $10^9$ fold increase in target DNA concentration. In order to add dATP overhangs to PCR product for cloning in TA cloning vector, the PCR Phusion polymerase amplified product is incubated with Taq polymerase for 20 minutes at 72° C.

TABLE 8

| PCR reaction condition | | | |
| --- | --- | --- | --- |
| Initial denaturation | 94° C. | 3 minutes | |
| Denaturation | 94° C. | 30 seconds | 30 Cycles |
| Annealing | 60.4° C. | 50 seconds | |
| Extension | 72° C. | 1 minute | |
| Final extension | 72° C. | 10 minutes | |
| Throughout the process | 4° C. | | |

TABLE 9

| PCR reaction mixture | | |
| --- | --- | --- |
| Reagents | Sample | Control |
| Template | Respectively | 0.0 µL |
| dNTPs | 1 µL | 1 µL |
| Fw primer | 1 µL | 1 µL |
| Rv primer | 1 µL | 1 µL |
| Phusion Polymerase | 1 µL | 1 µL |
| Phusion buffer HF (5X) | 10 µL | 10 µL |
| Purified water | Respectively | 36 µL |
| Total reaction mixture | 50 µL | 50 µL |

The PCR product is further modified with Taq DNA polymerase for tailing. Final PCR product is then electrophoresed in agarose gel for elution of amplified fragment. The amplified fragments are then gel eluted using QIAEX II Gel extraction kit.

Ligation

PCR amplified and gel eluted products are ligated in commercially available pTZ57R/T vector. Ligation protocol is described as follows

TABLE 10

| Ligation mixture | |
| --- | --- |
| DNA (pTZ57R/T) | 1 µL |
| DNA (CRISPR(PCR product)) | 4 µL |
| T4 DNA ligase | 1 µL |
| T4 DNA ligase buffer (10X) | 1 µL |
| Purified water | to 10 µL |
| Total | 10 µL |

The above ligation mix is incubated at 4° C. overnight and 50% of ligated mix is transformed into DH5alpha E. coli competent cells by heat shock method.

Transformation of Ligated Sample into Bacterial Cell by Heat Shock Method

The purpose to transform bacterial cells is to clone and propagate the plasmid DNA. 20 µL aliquot of competent E. coli cells (DH5alpha) are taken from −80° C. freezer and thawed on ice for 5 minutes. 50% of ligated sample (pTZ57R/T+CRISPR(PCR)) is added to the competent cells and gently mixed and incubated on ice for 20 minutes. The mix containing tube is placed on water bath/dry bath at 42° C. for 50 seconds. The tube is placed back on ice for 2 minutes. 0.950 ml of 37° C. warmed LB broth (without ampicillin antibiotic), is incubated at 37° C., 220 rpm for 1 hour, in shaker. 100 µL of the resulting culture is spread on warmed LB+ ampicillin culture plates. The plates are incubated overnight at 37° C. incubator.

Plasmid DNA Isolation from Bacterial Cells Using QIAPrep Spin Miniprep

The purpose of this procedure is to grow/culture bacteria that contain a specific DNA plasmid, which is used in following experiments. 5 mL of LB+ ampicillin broth is added into autoclaved tubes, isolated bacterial colonies are inoculated from the culture plates to the LB broth+Ampicillin culture tubes. Tubes are incubated at 220 rpm, at 37° C. overnight (approximately 16-18 hours depending on the growth of the bacterium). Overnight culture of 4.5 mL is centrifuged at 13 rpm for 1 minute. Plasmid DNA is isolated using commercially available QIAGEN plasmid isolation kit. Plasmid DNA is eluted with highly pure molecular biology grade water and stored at −20° C. freezer until further use.

Positive Clones Selected Using Restriction Digestion with EcoR I-HF and Hind III-HF Enzymes Plasmid DNA thus isolated is tested for presence of insert, in this case the PCR amplified fragment. The pTZ57R/T vector contains multiple restriction enzyme sites flanking the cloned PCR product. The restriction sites EcoRI and HindIII are selected for restriction digestion as described in below table. The reaction is carried out at 37° C. for 2 hours for complete digestion of the plasmid DNA. Following restriction digestion, the mixture is electrophoresed in 1% agarose gel for 1 hour. The PCR product insert, if present, separates from pTZ57R/T vector backbone and the confirmed bacterial clones are used for DNA sequencing.

TABLE 11

| Restriction enzyme digestion - reaction mix | |
|---|---|
| DNA (pTZ57R/T + CRISPR(PCR products)) | 2 µg |
| EcoRI-HF | 1 µL |
| Hind III-HF | 1 µL |
| Cut smart buffer (10X) from New England Biolabs | 2 µL |
| Purified water | to 20 µL |
| Total | 20 µL |

The present disclosure depicts the representative restriction enzyme digestion of PCR amplified product in pTZ57R/T vector to confirm presence of inserts from different CHO S cell lines. Plasmid DNA preparations from independent bacterial clones are digested with EcoRI and HindIII restriction enzymes flanking the PCR fragment cloned in the vector and the mixture is electrophoresed in 1% agarose gel. The size of resulting DNA fragments are estimated from the DNA molecular weight standards. The bacterial clones are used for automated sequencing to know the status of FUT8 locus in different CHO S cell lines.

Example 7: Sequence Data Analysis and Identification of INDELs

Sequencing—

The confirmed plasmids are then sequenced with specific sequencing primers present in the pTZ57R/T vector backbone. Sequence data is generated in automated DNA sequencing instruments following appropriate protocols. Sequencing is carried out with both forward and reverse sequencing primers to ensure proper sequence information.

DNA Sequence Analysis—

DNA sequencing data from all plasmids are analyzed. DNA sequence from plasmid DNA derived from CHO S parental cell line and various CRISPR/Cas mediated FUT8 knock out CHO S clonal cell lines are compared and differences in DNA sequences are identified. From each CHO S cell line clone, PCR products are generated and cloned in *E. coli*. Multiple *E. coli* clones are sequenced to confirm nucleotide sequence modification at the target genomic locus.

CHO S parental cell line—sequence of Exon-7 of FUT8 gene (SEQ ID No. 20) is in upper case. Intron sequence is in lower case and underlined.

<u>aagaaataagctgaatcagctctgac</u>ttattgtgtgattttcaatac

<u>ctgtgaccaaaatgagaagttaactccttatatctttatcttatttg</u>

<u>tttctctggaag</u>AATCCCAAGGACTGCAGCAAAGCCAGAAAGCTGGT

ATGTAATATCAACAAAGGCTGTGGCTATGGATGTCAACTCCATCATG

TGGTTTACTGCTTCATGATTGCTTATGGCACCCAGCGAACACTCATC

TTGGAATCTCAGAATTGGCGCTATGCTACTGGAGGATGGGAGACTGT

GTTTAGACCTGTAAGTGAGACATGCACAGACAGGTCTGGCCTCTCCA

CTGGACACTGGTCAGgt<u>aaggagcatgtgcaccatgaaagatctctg</u>

<u>gttaggtcagattagcac</u>

CHO-S FUT8 knockout clonal cell line sequences are provided below. It is observed that the Exon 7 sequence is mutated in the cell lines.

Clone CR2TMCHO 1A allelic version:
SEQ ID NO. 21
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCTGTTTAGACCTGTAA

GTGAGACATGCACAGACAGGTCTGGCCTCTCCACTGGACACTGGTCA

G

Clone CR2TMCHO 1A allelic version:
SEQ ID NO. 22
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGACTCACGGGGATTTCCAAGTCTCCACCCCATTGACGTCAATG

GGAGTTTGTTTTGGCACCAAAATCAACGGGACTTTCCAAAATGTCGT

AATAACCCCGCCCCGTTGACGCAAATGGGCGGTAGGCGTGTACGGTG

GGAGGTCTATATAAGCAGAGCTCGTTTAGTGAACCGTCAGATCACTA

GAAGCTTTATTGCGGTAGTTTATCACAGTTAAATTGCTAACGCAGTC

AGGCCAACAGAGACCACACCCAAGCTGGCCGCCACCATGGCCCCAAA

GAAGAAGCGGAAGGTCGGTATCCACGGAGTCCCAGCAGCCGACAAGA

AGTACAGCATCGGCCTGGCCATCGGCACCAACTCTGTGGGCTGGGCC

GTGATCACCGACGAGTACAAGGTGCCCAGCAAGAAATTCAAGGTGCT

GGGCAACACCGACCGGCACAGCATCAAGAAGAACCTGATCGGAGCCC

TGCTGTTCGACAGCGGCGAAACAGCCGAGGCCACCCGGCTGAAGAGA

ACCGCCAGAAGGATGGGAGACTGTGTTTAGACCTGTAAGTGAGACAT

GCACAGACAGGTCTGGCCTCTCCACTGGACACTGGTCAG

-continued

Clone CR2TMCHO 1B allelic version:
SEQ ID NO. 23
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCATCTGGAGGATGGGA

GACTGTGTTTAGACCTGTAAGTGAGACATGCACAGACAGGTCTGGCC

TCTCCACTGGACACTGGTCAAATCCCAAGGACTGCAGCAAAGCCAGA

AAGCTGGTATGTAATATCAACAAAGGCTGTGGCTATGGATGTCAACT

CCATCATGTGGTTTACTGCTTCATGATTGCTTATGGCACCCAGCGAA

CACTCATCTGGAGGATGGGAGACTGTGTTTAGACCTGTAAGTGAGAC

ATGCACAGACAGGTCTGGCCTCTCCACTGGACACTGGTCAG

Clone CR2TMCHO 1B allelic version:
SEQ ID NO. 24
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGTTGCCTAATAGAACAACCTTTGCC

TGGTTGTTACAAAATATATTCTCTGTACCAGTATCTAGTTTTACAAT

GAGCTATGGAATGTTAATGATTTATTTGTCTACATTATAAATTATAT

TGCTTTGATTTGCTCTAAGTGGAACAAACACTCATCTTGGAATCTCA

GAATTGGCGCTATGCTACTGGAGGATGGGAGACTGTGTTTAGACCTG

TAAGTGAGACATGCACAGACAGGTCTGGCCTCTCCACTGGACACTGG

TC

Sequence data is collected from analysis of 5-15 independent bacterial clones sequenced with both forward and reverse sequencing primers. The sequencing data suggests deletions of variable lengths in multiple clones compared to CHO S parental cell line. Deletion of bases is observed in clone CR2TMCHO 1A and CR2TMCHO 1B allelic versions. All deletions are located at the CRISPR/Cas target site.

The data suggests various INDELs present at the FUT8 genomic locus in CHO S cell lines transfected with CRISPR/Cas system targeting FUT8 gene and overexpressing Afucosylated AntiHer2 Antibody. In many cases, it is observed that there are modifications at the targeted bases. Such diversity of genomic modification through CRISPR/Cas complex is possible due to endogenous DNA single strand breaks at close proximity and repair through non homologous end joining. All of these cell lines are selected through functional screening assay, namely LCA-FITC flow cytometry assay. The results also imply high efficiency of the functional assays to isolate and identify CHO S FUT8 knock out cell lines over expressing AntiHer2 antibody.

It is also revealed that the design of the CRISPR/Cas complex depicted in this disclosure is highly efficacious as this one pair of CRISPR/Cas complex with the Cas9n endonuclease provides a highly sequence specific gene alteration at the targeted FUT8 locus in CHO S cell lines.

Composite analysis of the sequence data is used to identify potential FUT8 knock out CHO S cell lines where FUT8 genomic target locus is modified through deletion and/or insertions (INDELs). The DNA sequences are then aligned to show distinct differences. FIGS. 8A and 8B provides the alignment of nucleotide sequences of CHO S control cell line and FUT8 knocked out Afucosylated Anti Her2 antibody expressing CHO S cell line. The DNA sequence information is used to assign amino acid sequence of the FUT8 gene (exon 7). The amino acid sequences are then aligned to identify deletion, frame shift mutation, insertion of stop codons as well as amino acid substitutions at specific locations. FIGS. 8A and 8B depicts the extent of nucleotide modification observed in the CHO S FUT8 knock out cell lines when compared to CHO S parental cell line. The data provides a representation of FUT8 genomic DNA organization among CHO S FUT8 knock out cell lines.

Amino Acid Sequence Analysis of the CHO S Cell Lines Over Expressing AntiHer2 Antibody Transfected with CRISPR/Cas System Targeting FUT8 Gene Genomic DNA sequence at the FUT8 locus of CHO S parental cell line and CHO S cell lines over expressing Anti Her2 antibody and transfected with CRISPR/Cas system targeting FUT8 gene are further analyzed to understand the impact of DNA sequence INDEL on FUT8 protein status. DNA sequences at the targeted FUT8 locus is translated into amino acid sequences using vertebrate codon bias. The amino acid sequence of exon7 region is studied closely and the results are summarized in below table 12. When compared to CHO S parental cell line, the FUT8 knock out cell lines revealed modifications involving frame shift mutations and introduction of stop codons.

In many instances, frame shift mutations are observed, which alter the C-terminal region of the FUT8 protein to make it non-functional enzyme. In addition, stop codon is introduced as an effect of frame shift mutation and thereby the FUT8 protein is truncated and non-functional in these clones.

TABLE 12

Amino acid sequence data of the CHO S clonal cell lines

| Cell line information | Genetic makeup at FUT8 target genomic locus | Amino acid sequence derived from DNA sequencing data |
| --- | --- | --- |
| CHO S parental cell line | Wild type FUT8 amino acid sequence | NPKDCSKARKLVCNINKGC GYGCQLHHVVYCFMIAYGT QRTLILESQNWRYATGGWE TVFRPVSETCTDRSGLSTG HWS (SEQ ID NO. 5) |
| CR2TMCHO 1A; allelic version | Frame shift with STOP CODON | NPKDCSKARKLVCNINKGC GYGCQLHHVVYCFMIAYGT QRTLCLDL* (SEQ ID NO. 25) |
| CR2TMCHO 1A; allelic version | Frame shift with STOP CODON | NPKDCSKARKLVCNINKGC GYGCQLHHVVYCFMTHGDF QVSTPLTSMGVCFGTKING TFQNVVITPPR* (SEQ ID NO. 26) |
| CR2TMCHO 1B; allelic version | Frame shift with STOP CODON | NPKDCSKARKLVCNINKGC GYGCQLHHVVYCFMIAYGT QRTLIWRMGDCV* (SEQ ID NO. 27) |
| CR2TMCHO 1B; allelic version | Frame shift with STOP CODON | NPKDCSKARKLVCNINKGC GYGCQLHHVVYCFMIAYGT QLPNRTTFAWLLQNIFSVP VSSFTMSYGMLMIYLSTL* (SEQ ID NO. 28) |

Furthermore, it is observed that the selection of target amino acids in the FUT8 protein sequence is highly effective. Targeting conserved amino acids at positions of wild type FUT8 protein with only one pair of CRISPR/Cas complex has created mutations at the targeted locus in multiple knock out cell lines (FIG. 9).

All Fucose Knock out clonal CHO S cell lines over expressing Afucosylated AntiHer2 antibody and confirmed through the genome sequencing protocols described above are stored in liquid nitrogen storage as Research Cell Banks and Working Cell Banks. Multiple vials of Research Cell Banks and Working Cell Banks are stored in liquid nitrogen storage for future use.

Example 8: Upstream Process Development from the Single Cell Clonal Cell Line Expressing Afucosylated Anti Her2 Antibody Product A vial of working cell bank containing Fucose Knock out clonal CHO S cell line over expressing Afucosylated Anti-Her2 antibody is used to start the 2 liter Bioreactor culture protocol. The cells are thawed and seed train cultures are started in 150 ml baffled shake flask. The culture is further expanded to 250 ml baffled shake flask over a period of 11 days for inoculation of 2 L bioreactor. For each inoculum step a starting cell density of about 0.3 to about $0.5 \times 10^6$ viable cells per milliliter is used.

The production bioreactor is run in fed-batch mode. The bioreactor is a stirred tank reactor with a working volume of about 1.3 L to about 2 L. The media used is a commercially available chemically defined media. Aeration is performed by sparging. Process parameters such as pH, temperature, dissolved oxygen and agitation rate are controlled automatically. Some medium components are fed as separate sterile solutions to the bioreactor. These comprise glucose, amino acids, vitamins, and trace elements. After several days of fermentation with continuous monitoring of many in-process control parameters such as cell density, viability, pH, dissolved oxygen and metabolite levels such as Glucose, Glutamine, Lactate, Ammonia, Glutamate, IgG and LDH, the batch is harvested on day 10 with around 80% viability. The intact cells and cell debris are removed from the culture broth by centrifugation. The profile of in-process parameters are depicted below.

As shown in FIG. 10A, the cell count started increasing consistently from day to day 5, the maximum count obtained is around $6 \times 10^6$ cells/ml and then slowly started decreasing with production phase. On the day of harvest, the cell count is $4.5 \times 10^6$ cells/ml. Viability profile has been depicted in FIG. 10B. It is essential to maintain the fermentation culture above 80% viability so that cells remain healthy and active. The viability is maintained above 90% throughout the growth phase by providing the feed and the culture is harvested with 80% viability on day 10. Mammalian cells are typically cultured in conditions where the osmolality is in the range of 300-500 mOsm/kg. Higher osmolality can increase the specific productivity of recombinant proteins; however, this is often accompanied by an impact on cell growth. Therefore, osmolality is maintained below 500 mOsm/Kg throughout the fermentation batch, as shown in FIG. 11A. The composition of basal media and feeds had a substantial effect on antibody titers as shown in FIG. 11B. The highest Afucosylated Anti HER2 antibody product concentrations of 1.8 g/L is achieved in cultures grown for 10 days.

It is well known that cultured mammalian cells such as CHO S cell line culture frequently consume nutrients like glucose and glutamine beyond their stoichiometric needs and secrete the waste products lactate and ammonia in recombinant CHO S cell lines. Carbohydrates are the main source of energy in the medium. The most commonly used carbohydrate in mammalian cell culture is glucose. It provides the cells with energy and acts as the major source of carbon for synthesis of proteins. Amino acids, which form the building blocks required by the cell to produce proteins, form an important constituent. Concentration of amino acids in the media greatly influences the maximum cell density that a culture can achieve. Essential amino acids like L-Glutamine act as a nitrogen source for nucleotides and also as an alternate source of metabolism. The profile for glucose and glutamine consumption during fermentation run has been shown in FIG. 12A and FIG. 12B respectively. Glucose profile is maintained around 2 g/L during the fermentor run. Glutamine level is also maintained less than 1 mmol/L during the fed-batch.

Ammonium ion has a stronger impact on cell culture than lactate because high concentration of ammonium ion can inhibit growth and impair productivity. The precise mechanism of ammonium ion toxicity in cells is not clear, even though this effect has been shown to depend on pH. In the fermentation run, ammonium concentration is obtained as around 8 mmol/L as shown in FIG. 13A. Lactate also can cause a significant reduction of the pH of the medium, which inhibit the cell growth. Lactate concentration increased till day 5, but it slowly reduced to around 0.75 g/L on day 10, when the batch is harvested (FIG. 13B).

The present disclosure describes the optimal growth conditions required for over expression of Afucosylated Anti-Her2 antibody product at 2 liter fed batch bioreactor. The results revealed that these unique cell lines developed through transfection of CRISPR/Cas system maintain major biochemical parameters monitored during 2 liter fed batch bioreactor production. This observation again confirms that using the unique CRISPR/Cas system, the methodology has successfully developed a novel Afucosylated monoclonal antibody product from a CHO S cell line over expressing AntiHer2 antibody.

The CRISPR/Cas system and the methodology described herein has the potential to develop Afucosylated monoclonal antibody from any CHO S cell line over expressing any monoclonal antibody.

Example 9: Purification of Afucosylated AntiHer2 Antibody from Fed Batch Culture of Single Cell Clonal Cell Line The CHO S cell line over expressing AntiHer2 antibody is genetically modified to disrupt the Fucose biosynthetic pathway using CRISPR/Cas system targeting the FUT8 genomic locus. Cell culture material from 2 liter fed batch bioreactor production is harvested after 10 days of culture with more than 80% viability. The culture is processed for purification of Afucosylated AntiHer2 Antibody, the procedure is described below.

Quality attributes of monoclonal antibody or bio therapeutic proteins are highly affected by both process and product related impurities. Modern downstream purification processes are increasingly driven by economic factors. It's mandate to shorten the time to deliver the product to market means that the process development must be fast and inexpensive without compromising quality. Keeping this in view, a good product development workflow is very essential and will ensure a robust process where critical parameters have been identified and are under control. The concept of Quality by Design (QbD) with the support of Process analytical technology (PAT) in both upstream and downstream early stage process development has been employed in recent years by many biopharmaceutical companies.

The downstream process development of monoclonal antibodies (typically at the laboratory scale) involves optimization and integration of several unit operations that provide the desired purity, product quality, throughput and yield. CHO (Chinese Hamster Ovary) cells are widely used in monoclonal antibodies production, where proteins expressed using chemically defined media in fed batch mode. Other cell lines used for the production of therapeutic monoclonal antibodies include NS0, SP2/0 and PER.C6.

CHO cells are most commonly used for manufacturing of number of mAb products. In recent years, efforts made to increase the productivity by controlling fermentation process parameters and efficient feeding strategy. Once the CHO cell culture is harvested, the harvest is subjected to clarification to remove cells, cell debris, media components and impurities. This is accomplished by any of the methods namely centrifugation, depth filtration or tangential flow filtration (microfiltration). Each clarification method has its own advantages as well as drawbacks. Centrifugation step was used in earlier days for clarification. The clarification efficiency of the centrifugation process depends upon many factors which includes centrifuge feed rate, G-force, bowl geometry, operating pressures, discharge frequency and ancillary equipment used in the transfer of cell culture to the centrifuge. The cell culture characteristics such as total cell density and culture viability during the culture process and at harvest will also affect separation performance. The next method of choice is Tangential flow filtration, where the cell culture flows tangential to the microporous membrane under set pressure limit that leads to the separation of cells, cell debris and insoluble particles. A series of concentration and diafiltration steps is followed in cell separation. Control of pressure is very critical, since the pressure force can lyse the cell that leads to increased release of intracellular proteins, host cell DNA, proteases etc. Most commonly used pore size is 0.22 micron and 0.11 micron also used in recent years.

Depth filtration is the most commonly used clarification tool. Due to multiple mechanisms such as electrokinetic adsorption, size exclusion and hydrophobic interaction, this type of clarification step has been used extensively to separate or remove cells, cell debris, process contaminants and soluble as well as insoluble impurities. Depth filtration also helps in removal of host cell DNA. In recent days, precipitation/flocculation-based pretreatment of cell culture fluid had been employed to reduce the load onto the clarification stage. Initially in laboratory scale, optimization of filter type, pore size, surface area and flux will be done and then scaled up to pilot scale.

After clarification, the clarified sample is subjected to filtration using a filter of 0.22 μm pore size. The filtered sample is loaded onto Protein A affinity chromatography column, where the bound molecules are eluted by low pH buffer. Protein A affinity chromatography is a well-established capture step, which gives purity above 95% with highest recovery. Optimum acidic pH for monoclonal antibodies elution should be studied experimentally, since mAbs have a tendency to aggregate at low pH. The eluted protein is subjected to virus inactivation (low pH) and neutralization to remove viruses. There are number of Protein A resins commercially available and few are alkali tolerant with high protein binding capacity. Commercial Protein A resins are available from various suppliers namely GE Healthcare, Repligen, Merck Millipore, Tosoh Bioscience etc.

One or two chromatography polishing steps are generally employed to remove both product related impurities such as product isoforms, clipped species, charge variants and process related impurities such as host cell proteins (HCP), host cell DNA (HCD), endotoxins, adventitious viruses, protein A leachates. Generally, either anion or cation exchange chromatography is employed as a second chromatography step. Although, hydrophobic interaction chromatography, mixed mode chromatography and hydroxyapatite chromatography are used in few cases. The purification process flow includes two virus removal steps, one is low pH inactivation post capture Pro A chromatography stage and second one is nanofiltration (virus filtration) step after final polishing chromatography. In recent years, efforts have been made to use either ion exchange chromatography or mixed mode chromatography as a capture step instead of Pro A Chromatography. Anionic membrane absorbers are also used in downstream processing of mAbs as negative binding mode, where protein elute in flow through and impurities bind to the membrane. Lastly, the purified product after final polishing chromatography step is concentrated and diafiltered into the final formulation buffer using tangential flow filtration.

The present disclosure describes the methodologies to purify Afucosylated AntiHer2 antibody produced from CHO S cells transformed with CRISPR/Cas mediated FUT8 knock out cell line using Protein A Capture Chromatography and other purification technologies.

1. Afucosylated antiHer2 Antibody containing cell culture sample from 2 liter Bioreactor
2. Clarification (Centrifugation & Depth filtration
3. Affinity Chromatography
4. Low pH viral Inactivation
5. AEX chromatography (NB)
6. CEX Chromatography
7. Analysis of Afucosylated antiHer2 Antibody Clarification:

About 1410 ml of KO CHO cell culture harvest with viability of 79.7% is subjected to centrifugation to remove cells and cell debris. The supernatant with the turbidity of 22.5 NTU is collected carefully and passed though ZetaPlus BC25 depth filter (25 cm$^2$ Area) to remove host cell proteins and suspended solid particles. The secondary clarified sample is filtered using 0.22 μm filter (47 mm Area) and the filtrate collected in a sterile bottle to load on Protein A affinity column.

Affinity Chromatography:

12 miligram of Carboxypeptidase B is added to around 1400 milliliter of clarified sample (2400 miligram) and incubated at 37° C. for 1 hour to remove C-terminal lysine variants. After incubation, the clarified sample is loaded onto pre-equilibrated MabSelectSure ~70 ml XK 26/20 column in equilibration buffer (30 mM Sodium Phosphate buffer, 150 mM NaCl pH 7.20±0.20) at 8.8 ml/min flow rate. Around 1550 ml of flow through is collected. Next Passage is through equilibration buffer to remove loosely bound impurities and host cell proteins. Next Passage is through 1 column volume of high salt ish buffer (30 mM Sodium Phosphate buffer, 1 M NaCl pH 7.20±0.20) followed by 3 column volume of low pH Ish buffer (30 mM Sodium Phosphate buffer, 50 mM NaCl pH 6.0±0.20) to remove impurities. Bound proteins are eluted by elution buffer (30 mM Phosphate buffer, 50 mM NaCl pH 3.0±0.20).

Virus Inactivation:

The pH of Protein A elution is adjusted to 3.0±0.2 for virus inactivation and the sample is incubated for 30 minutes at 24° C.±2° C. The sample is then neutralized to pH 6.0±0.2 using 1M Tris to purify further.

Anion Exchange Chromatography:

After virus inactivation, sample at pH 6.0 is diluted using purified water to reduce the conductivity and again adjusted the pH to 6.±0.2. Diluted sample (~1000 milliliter) is loaded on pre-equilibrated XK16/40 Q Sepharose 6 FF column, collected flowthrough, where the product eluted in flow through since this chromatography step is set at negative binding mode. This step is followed by elution of bound impurities, host cell DNA and truncated species by elution buffer (30 mM Sodium Phosphate buffer, 1 M NaCl pH 7.20±0.20) in single step (100% of Concentration B). The elution is collected as single fraction.

Cation Exchange Chromatography:

Flow Through from AEX chromatography is loaded on pre-equilibrated XK26/40 Capto S Column in Equilibration buffer (50 mM Histidine buffer pH 6.0, ~2.23 milli siemens). Flow through sample is collected. Next passage is through equilibration buffer of ~2 column volume to remove traces of impurities. Elution is started from 0 to 20% Concentration B (Elution buffer: 50 mM Histidine buffer pH 6.0, ~14.50 milli siemens) in single step (~2.5 mS to ~7.30 milli siemens) followed by 20 to 22.5% in single step (~7.30 milli siemens to ~7.50 milli siemens). Gradient elution is started from 22.5% to 80% in gradient (20 column volume gradient length). The fractions are collected of about 6 ml size. 100% Concentration B is then passed followed by high salt elution buffer (30 mM Sodium Phosphate buffer pH 7.20 with 1 M NaCl).

Data Analysis

The secondary clarified sample reveals turbidity less than 5 nephlometric turbidometry unit (NTU) after clarification by depth filtration. The Protein A Affinity Chromatography profile (FIG. 14A) reveals the removal of some Host cell proteins (HCPs) in high salt ish and reasonable yield in Protein A elution is observed, when bound proteins eluted using low pH buffer (pH 3.0). Based on Protein A elution profile, extra tailing peak is not observed and this shows no aggregation of the product during elution. Based on $A_{280}$ analysis of Protein A eluted sample, it is observed that there is above 95% of recovery from the harvest.

AEX Chromatography (FIG. 14B) is operated in Flow through mode, where the product does not bind to the resin and loading at low pH gives more net positive charge. In this Chromatography step, observed product is completely eluted in AEX Chromatography in Flow through, where the product does not bind to the column as expected and only Host cell DNA (HCDs), Host cell proteins (HCPs) and some truncated species are bound to the resin. The bound impurities or contaminants are eluted from the column using high salt elution buffer.

In CEX Chromatography step (FIG. 14C), no protein elution is observed in flow through and the Afucosylated AnitHer2 Antibody product is bound to resin completely. One peak is observed during the wash step at low salt concentration in CEX Chromatography and gradient elution yielded a broad elution peak and a better separation of charge variants is observed when 20 column volume length of gradient is employed in elution. The products eluted completely within 200 mM NaCl concentration. After elution of Afucosylated AntiHer2 Antibody product a tiny elution peak is observed in high salt elution condition, indicating complete purification within 200 mM NaCl concentration.

Example 10: Characterization of Afucosylated AntiHer2 Antibody Product

Multiple analytical methods are used to characterize the Afucosylated AntiHer2 Antibody product produced from the CHO S cell line transformed with CRISPR/Cas system targeting FUT8 gene knock out.

Following methodologies are used for characterization of Afucosylated Anti Her2 Antibody product.

1. Isoelectric focusing of the antibody product
2. SDS PAGE Analysis of the Afucosylated AntiHer2 antibody product
3. Immunoblotting of the Afucosylated AntiHer2 antibody product
4. HER2 antigen binding ELISA with the afucosylated AntiHer2 Antibody product
5. Cell based ELISA assay showing Her2 antigen recognition on cell surface
6. Protein concentration of purified Afucosylated Anti-Her2 antibody product from CHO S cell line transformed with CRISPR/Cas system targeting FUT8 gene
7. Charge variant analysis by weak cation exchange of Afucosylated AntiHer2 antibody
8. N-glycan profiling of the Afucosylated AntiHer2 antibody product to establish 100% afucosylation
9. Flow cytometry analysis of the Afucosylated AntiHer2 antibody product to reveal Her2 antigen recognition in a dose dependent manner
10. SPR Binding Kinetics to ensure improved FcγRIII binding by the Afucosylated AntiHer2 Antibody
11. Antiproliferation assay of Her2 over expression cell line to ensure biological functionality of the Afucosylated AntiHer2 antibody product
12. ADCC assay with the Afucosylated AntiHer2 antibody product to establish improved cytotoxicity of tumor cells 1. Isoelectric Focusing Isoelectric focusing methods are widely applied for the separation of proteins based on their charge difference. Isoelectric focusing (IEF) is an electrophoretic technique for separation of proteins based on their isoelectric point (pI). The principle of isoelectric focusing is that in a pH gradient, the sample components migrate towards the anode or the cathode to the pH values, where their net charges are become zero (their pI).

Method Protocol

The samples used in the study for identification of charge variants are Trastuzumab (obtained from Roche), and afucosylated Anti-HER2 antibody developed from CHO S cell line transfected with CRISPR/Cas system targeting FUT8 gene. All samples are diluted and kept at a concentration of 1 mg/ml using ultra-pure milli Q water as diluent and 20 μg protein samples are loaded on to IEF sample applicator. Standard IEF conditions are used. 1M sodium hydroxide and 1M ortho-phosphoric acid are used as the cathode buffer and anode buffer respectively. Gel mixture used in this study is 5%. After the run, the gels are fixed with 2% trichloroacetic acid for 30 minutes. Coomassie brilliant blue solution is used for staining solution.

2. SDS Page Analysis

Antibody samples are analyzed by SDS-PAGE under reducing and non-reducing conditions using 10% (v/v) resolving gels. Tris Glycine SDS PAGE is carried out with the supplier's protocol (Biorad). Polyacrylamide gels are prepared from acrylamide and bis-acrylamide stock solution (29:1), Stacking buffer (1M Tris-HCl pH 6.8), Resolving buffer (2M Tris-HCl pH 8.8), 10% SDS, APS and TEMED as the catalyst. Stacking gel is used at 4% concentration.

5 μg of the antibody samples are mixed with 5× sample buffer (1M Tris-HCl pH 6.8, 10% SDS, β-mercaptoethanol (in case of reducing condition), 50% glycerol, 2% (w/v) bromophenol blue). The mixture is then heated for 5 min and loaded on to the gel. The SDS-PAGE of antibody samples is carried out at a voltage of 150 volts for 60 minutes. Protein Marker Standard (Biorad) with molecular weight ranged between 10-250 kDa is used. Protein staining is performed with Coomasie brilliant blue 0.2% (w/v). The stained gels are then washed with a mixture of methanol:acetic acid solution (40%: 10%) and then photographed by Canon digital camera to visualize the protein bands.

3. Immunoblotting

Antibody samples that are resolved in SDS-polyacrylamide gels are transferred to a PVDF membrane. After blocking with 1% (w/v) BSA in 0.05% Tween/PBS (PBST) for 30 minutes, the membrane is ished 1 time with PBST for 10 min and incubated further with a 1:5000 dilution of Goat anti-mouse IgG secondary antibody HRP conjugated antibody for 30 minutes at RT and detected using DAB substrate.

4. Quantification of Afucosylated Anti-Her2 Antibody by Her2 Binding ELISA

Anti-HER2 IgG1 Trastuzumab, a humanized anti-human epidermal growth factor receptor-2 (HER2) monoclonal antibody, is used for treatment of metastatic breast cancer patients overexpressing HER2 on tumor cells. Quantification of anti-HER2 monoclonal antibody can be carried out using different methods, for example, an ELISA based method. Human Her2/ErbB2 Protein (Human Her2, His Tag) Thr 23-Thr 652 (Accession #AAA75493) produced in human 293 cells (HEK293) at ACROBiosystems is used to coat on the 96 well plates. The receptor is Human Her2; His Tag is fused with a poly-histidine tag at the C-terminus, and has a calculated MW of 70.2 kDa. The predicted N-terminus is Thr 23. DTT-reduced Protein migrates as 110-115 kDa in SDS-PAGE due to glycosylation Method Protocol 100 µl HER 2 protein (Acro bio systems, US) is coated onto the 96 well plates (cell culture delta surface treated plates) at a concentration of 1 µg/ml (diluted with 100 mM bicarbonate buffer, pH 9.6). Plate is kept for overnight incubation at 2-4° C. followed by wash with wash buffer (PBS+0.05% Tween 20) 2×200 µl. Nonspecific binding is blocked with blocking buffer (wash buffer+0.1% BSA) for 2 hours (200 µl) and washed with wash buffer twice. 100 µl of standard/samples are added and kept for incubation for 1.5 hours. Samples and standards are serially diluted in two folds with the range of 1.953-250 ng/ml. Secondary antibody is added to the plates and kept for incubation for 1 hour. TMB is used as a substrate. And the plates are read at 450 nm with 620 nm as background. All the measurements are done in duplicates. The sample/standard concentrations measured are determined using the four parameter nonlinear regression curve fitting program to generate the binding curves (Gen 5).

5. Cell Based Binding ELISA

Cell based ELISA is one of the method to estimate the binding potency of specific target molecule with specific receptor expressing cells. SKBR3 and BT474 cell lines (obtained from ATCC) over express HER2 receptors on cell surface. The cell lines are used to evaluate the binding potency of anti-HER2 antibody. Below protocol is followed in cell based ELISA assay,
 1. The cells are seeded into micro-titer plates;
 2. Overnight incubation at 37° C. in CO2 incubator;
 3. The cells are fixed with 10% formalin;
 4. The surface is ished and blocked;
 5. The target anti-HER2 antibody is added;
 6. Ishing and enzyme conjugated antibody is added;
 7. Substrate is added and reading is taken.

Method Protocol

Two cell lines are used in this study, namely SKBR3 and BT474 cells. SKBR3 and BT474 cells are passaged and maintained in the RPMI 1640 and DMEM medium respectively, supplemented with 10% FBS at 37° C. and 5% CO2. The cells are plated at a density of 5000 cells per well (100 µL) in 96 well plate delta treated surface and allowed to adhere overnight at 37° C. and 5% CO2. The following day the cells are washed with 2×200 µL cold PBS to remove the non-adherent particles. Next the cells are fixed with 100 µL of 10% formalin and incubated for 10 minutes at room temperature. The fixing solution is removed and washed with 2×200 µL of cold PBS and the plates are blocked with 200 µL of blocking solution [PBS+Tween 20 (0.05%)+0.1% BSA] for one hour. The plates are washed with 2×200 µL of wash buffer (PBS+0.05% Tween 20) to remove the excess blocking solution. 100 µL of sample/standard added in each well and incubated for 30 minutes in plate shaker. The plates are ished with 2×200 µL of ish buffer (PBS+0.05% Tween 20) to remove the non-specific interaction. 100 µL of secondary antibody (anti human Fc IgG1) is added and incubated for 1 hour. 100 µL of TMB substrate is added and the color developed is read at 450 nm with 620 nm as background. All the samples/standard is done in duplicates. The sample/standard concentrations measured are determined using the four parameter nonlinear regression curve fitting program to generate the binding curves (Gen 5). Table 13 shows the Sample/standard concentrations used for both cell lines (BT474 and SKBR3)

TABLE 13

Sample or standard concentrations used in cell based ELISA experiment

| S. No | Standard/Sample concentration (µg/ml) |
|---|---|
| 1 | 200.000000 |
| 2 | 50.000000 |
| 3 | 12.500000 |
| 4 | 3.125000 |
| 5 | 0.781250 |
| 6 | 0.195313 |
| 7 | 0.048828 |
| 8 | 0.012207 |
| 9 | 0.003052 |
| 10 | 0.000763 |
| 11 | 0.000191 |

6. Protein Concentration Measurements

The protein concentration is determined by Protein-A affinity chromatography using MAbPac Protein-A column (12 µm; 4×35 mm) on an Shimadzu Prominence-i HPLC. The mobile phase is Dulbecco's Phosphate Buffered Saline at a flow rate of 2.5 mL/min. The monoclonal antibody is eluted with 3% glacial acetic acid gradient. The column temperature is 25° C. and detection is at 280 nm. Chromatograms are integrated using Lab Solution Software and the concentration is estimated using standard curve plotted with Area under the peak against concentration of known standard.

7. Ion Exchange Chromatography

Charge variants are separated on a 4.0×250 mm Dionex ProPac cation exchange (IEC) column WCX-10. The mobile phase-A is 10 mM MES buffer at pH 6.8 and mobile phase-B is 10 mM IVIES buffer at pH 6.8 with 250 mM Sodium Chloride and the flow rate is 1.0 mL/min with run time of 21 min. The column temperature is 30° C. and detection is at 280 nm. Chromatograms are integrated using Lab Solution Software and relative percent peak area obtained.

8. Enzymatic N-Glycan Release and Labeling by Glycoworks RapiFluor-Ms N-Glycan Kit The sample preparation for N-Glycan profiling is performed using GlycoWorks RapiFluor-MS N-Glycan Kit (Waters, Milford, Mass., USA). The kit has four steps.
STEP 1: Rapid Deglycosylation,
STEP 2: Rapid Labeling of Glycosylamines,
STEP 3: HILIC Clean-Up of Labeled Glycosylamines,
STEP 4: Preparing Labeled Glycan for HILIC-FLR UPLC analysis.

9. UPLC-Fluorescence HILIC N-Glycan Profiling

2-AB derivatised N-glycans are separated by ultra-performance liquid chromatography (UPLC) with fluorescence detection on a Waters Acquity™ UPLC H-Class instrument consisting of a Quaternary solvent manager, sample manager and fluorescence detector under the control of Empower 3 chromatography workstation software (Waters, Milford, Mass., USA). The HILIC separations are performed using Thermo Accucore-150-Amide-HILIC column, 100×2.1 mm i.d., 2.6 µm particles, using a linear gradient of 80-60% acetonitrile at 1 mL/min in 26 minutes. Solvent A is 50 mM Ammonium Formate which is adjusted to pH4.4 with ammonia solution and Solvent B is acetonitrile. The injection volume of sample is 10 µL. Samples are maintained at 5° C. prior to injection and the column temperature is 60° C. The fluorescence detection excitation/emission wavelengths are ex=265 nm and em=425 nm, respectively.

10. Flow Cytometry Analysis

Specific binding of the mAb samples to HER2 antigen is investigated using indirect flow cytometry method. BT-474 cell line is obtained from ATCC which expresses high levels of HER2 receptors on its cell surface. BT-474 cells are cultured in DMEM/F12 Growth medium containing 10% FBS.

For the experiment, cells are trypsinized with 0.25% Trypsin-EDTA. After centrifugation at 1000 rpm for 3 min, pellet is suspended in 2% BSA in DPBS buffer to achieve a desired concentration of 0.1 million cells/ml. Then the cells are treated with varying concentration viz., 0.05 mg/ml, 0.025 mg/ml and 0.00125 mg/ml of biotin labelled Innovator Herclon and Anti-HER2 Antibody. Biotinylation of the antibody samples are performed using EZ SulfoLink Biotinylation kit (Thermo Scientific).

Volume of the antibody samples and cells are maintained at ratio of 1:1 and incubated at RT for 1 hr. 20 µl of 0.1 mg/ml Strep-FITC is added to the reaction mixture and incubated on ice bath for 30 min. All treated samples are analyzed with BD Accuri Flow Cytometer (BD Biosciences).

11. SPR Binding Kinetics

Binding kinetics studies for different charge variants are performed by Surface Plasmon Resonance (SPR) using a Biacore 3000 instrument. Variants and main species are analyzed for HER-2 binding kinetics and Fc gamma RIII (CD16a) binding kinetics. HER2 and CD16a ligands are immobilized on CM5 chip (GE Healthcare) using standard amine coupling procedure described by the manufacturer protocol.

12. Her2 Binding Kinetics

HER2, also known as neu and c-erbB2, is a member of the epidermal growth factor (EGF) receptor or HER family of tyrosine kinase receptors that also includes HER1 (EGFR/c-erbB1), HER3 (c-erbB3) and HER4 (c-erbB4). Overexpression of HER2 is frequently observed in breast and ovarian cancers and is associated with an unfavorable prognosis.

HER2 ecto-domine receptor (Sino Biologicals) is diluted to 2 ug/mL in Acetate buffer pH5.0 and the amine coupling protocol followed as mentioned in GE amine coupling procedure. The ligand immobilization is aimed for 500 RU with flow cell 2 (FC2) and flow cell 1 (FC1) serves as background without any ligand. All anti-HER2 Mabs are diluted with the running buffer (EMS P+1× buffer from GE Healthcare) in different concentrations from 100 nM to 6.25 nM with 2 fold dilutions. These individual concentrations are injected in duplicate for 5 minutes of association kinetics and then only running buffer is passed for 15 minutes of dissociation kinetics and the surface is regenerated with 30 sec injection of glycine buffer pH 1.5, 90 sec of glycine buffer pH 2.0 and with running buffer stabilization time of 1 minute.

Therapeutic antibodies are typically molecules of the IgG class and comprise an antigen-binding fragment (Fab) that engages the tumor cell antigen and a crystalline fragment (Fc) that binds to Fc gamma receptor (FcγR) on an effector cell such as a natural killer (NK) cell, monocyte, or macrophage. Fcγ receptors are well known molecule of the Immunoglobulin superfamily familiar to be involved in antibody-dependent cellular cytotoxicity (ADCC). The contribution of IgG Fc-mediated effector functions in ADCC has motivated the efforts being made to enhance interactions with Fc gamma receptors (FcγRs) for the development and manufacturing of therapeutic antibodies.

FcγRIII (CD16a V158) valine variant is used in this study, Ectodomain of CD16a receptor is procured from Acro bio systems, USA. All Afucosylated anti-HER2 antibody is serially diluted with the running buffer (HBS EP+1× buffer from GE Healthcare) in different concentrations from 0.833 µM to 0.05 µM (2 fold dilution). Analyte kinetics is determined using the Langmuir binding kinetics (1:1 binding model).

13. Antiproliferation Assay

BT474 cell line is used in the study and the cells are propagated and maintained using DMEM medium supplemented with 10% FBS at 37° C. and 5% $CO_2$. 2000 cells per well is used in the study. The sample/standard dilutions are performed in DMEM assay media (containing 2% FBS). 100 µL of sample/standard is added in 96 well plates along with 100 µL of cells and kept for 6 days incubation at 37° C., 5% CO2. After 6 days, 30 µL of Alamar blue is added and kept for 6 hours incubation. Then the plates are read at excitation wavelength of 530 nm and excitation wavelength of 590 nm. Four point nonlinear regression curve is obtained from PLA software. Below Table 14 shows the Sample/standard concentrations used for BT474 Antiproliferation assay

TABLE 14

Sample and standard concentrations used in antiproliferation assay

| S. No | Standard/Sample concentration (µg/ml) |
|---|---|
| 1 | 10.000000 |
| 2 | 2.500000 |
| 3 | 0.625000 |
| 4 | 0.156250 |
| 5 | 0.039063 |
| 6 | 0.009766 |
| 7 | 0.002441 |
| 8 | 0.000610 |
| 9 | 0.000153 |

Isolation of Effector Cells

Peripheral blood mononuclear cells (PBMC) are isolated by ficoll gradient centrifugation from heparinized blood. Cells are ished in DPBS (1×) and then again in complete media and then adjusted to the cell concentrations required to obtain the optimal effector:target (E:T) ratios.

14. ADCC Assay

BT-474 target cells (10,000 cells per well) are mixed with afucosylated monoclonal antibody samples in RPMI 1640 assay medium and distributed in 96 well plate. After 30 min of incubation, effector cells are added at a ratio of 1:20 (BT474 cells to effector cells) to cell and drug reaction mixture. Assay plate is incubated in $CO_2$ incubator at 370 C for 7 hours. The dead cell protease levels (indicator of cell death) released by the cells are measured using Cytotoxglo assay kit (Promega). After incubation, plates are kept on shaker for 30 minutes for uniform mixing. 20 μl of lysis buffer added to the control well for determining maximum cytotoxicity level. 20 μl of the Cytotoxglo reagent is added to each sample and control wells and incubated for 15 minutes at room temperature. Luminescence is measured using Biotek ELISA reader. Percentage Cytotoxicity values are calculated as follows: [(Test Sample−Low Control)/(Maximum Control−Low Control)]×100. Low control represents spontaneous cell death and Maximum control represents complete cell death.

Results and Discussion

The prospect of the afucosylated anti Her2 antibody are tested and characterized with the series of analytical experiments. Afucosylated AntiHer2 antibody is compared with Trastuzumab to compare biological activity.

IEF

IEF is performed to identify the charge variants (acidic and basic species) present. Four bands are clearly visible in innovator. The main band (FIG. 15) is observed in both Trastuzumab and Afucosylated Anti-Her2 Antibody product.

SDS Page

Under non-reducing conditions, a single major band corresponding to a molecular weight (MW) of 150 kDa is observed indicating the intact antibody (FIG. 16). While under reducing conditions, two bands are evident at 25 kDa and 50 kDa which are associated with light chain and heavy chains of the antibody, respectively. The band patterns observed for the Afucosylated Anti-Her2 Antibody product resembles the band pattern of the Trastuzumab.

Western Blotting

Western Blotting analysis is performed for the specific detection of the antibody samples. Trastuzumab is used for the evaluation of and comparison of protein patterns. The non-reduced antibody samples show a single distinct band when probed with secondary antibody. However, in the case of reduced samples, only a single band of heavy chain (around 50 kDa) is detected and not the light chain of the monoclonal antibody. This is because the secondary antibody that is used is specific only against Fc region of the antibody and not the light chain region. In FIG. 17, Afucosylated AntiHer2 antibody product reveals exactly same banding pattern in western blot experiment.

Anti Her2 Binding ELISA

Serially diluted different concentrations (60 ng/mL to 0.48 ng/mL) of Trastuzumab and Afucosylated anti-HER2 antibodies are analyzed for binding efficiency in HER2 coated ELISA plates. Observed result (FIG. 18) shows the similar interaction of Afucosylated anti-HER2 antibody to immobilized HER2 domain compared to Trastuzumab.

Cell Based ELISA

Cell based ELISA (FIGS. 19A and 19B) reveals comparable activity for afucosylated anti-HER2 Antibody and Trastuzumab. This method determines the binding activity between afucosylated anti-HER2 Antibody and Trastuzumab with the HER2 antigen expressed on breast cancer cells. Ideally BT474 cells have higher expression of HER2 antigens on the surface when compared with SKBR3 cells. Afucosylated anti-HER2 Antibody molecule shows equivalent binding potency in both cell lines, The binding potency for Afucosylated anti-HER2 Antibody against SKBR3 and BT474 cells are 89.1% and 80.3% respectively. The binding potency criteria for cell based ELISA is set at 75-125% in parallel line assay calculation software (PLA software).

Protein Concentration Measurements

The prototype Protein A column is used to measure the monoclonal antibody titer from harvested cell culture (HCC) till Drug Product stage. In the chromatogram (FIG. 20), 50 μL of each sample is injected onto prototype Protein A column. The first peak which eluted in the initial portion of the method and represents unbound material. The monoclonal antibody is released by passing a low pH 3% Glacial acetic acid. The monoclonal antibody titer is determined using a calibration curve previously generated. The typical chromatogram of each sample is shown in FIG. 20 and titer of each sample is tabulated below (Table 15).

TABLE 15

Results from Protein A concentration measurements

| Sample Details | FINAL Concentration (mg/ml) |
|---|---|
| INNOVATOR | 22.44 |
| ANTI-HER2 ANTIBODY.1 SAMPLE | 5.20 |

Ion Exchange Chromatography

The peaks of the ion exchange profiles are typically denoted into three distinct components. Early and late-eluting peaks are called acidic and basic variants, respectively. The most abundant peak is designated as the main peak. The ProPac WCX-10 column provides excellent peak efficiencies and high resolution for acidic and basic variant analysis of monoclonal antibodies as shown in FIG. 21, where the acidic, basic and main peaks are resolved in 21 minute run time and the percentage of each is tabulated in below Table 16.

TABLE 16

Results of Ion exchange chromatography

| Sample Name | Acidic Variant % Area | Main Peak RT | Main Peak % Area | Basic Variant % Area |
|---|---|---|---|---|
| ANTI-HER2 ANTIBODY.1 SAMPLE | 17.22 | 7.05 | 57.45 | 25.33 |
| INNOVATOR | 32.57 | 7.03 | 53.44 | 13.99 |

HILIC N-Glycan Profiling

One of the important quality attributes for therapeutic monoclonal antibodies is Glycosylation profile. To check the glycan distributions in Trastuzumab and Afucosylated Anti-Her2 Antibody products are analyzed by HILIC N-glycan profiling method. The major glycan such as G0, G1, G1', G2, G0F, G1F, G1F' and G2F are listed in the following Table 17 for Trastuzumab and Afucosylated Anti-Her2 Antibody product. Overall percentage of afucosylated glycan for Trastuzumab and Afucosylated Anti-Her2 Antibody samples are 8.95% and 100%, respectively. Glycan profile for Trastuzumab and Afucosylated Anti-Her2 Antibody is shown in FIG. 22

TABLE 17

Results of glycan profiles

| Sample name | | Trastuzumab | Afucosylated Anti-her2 antibody |
|---|---|---|---|
| GLYCAN VARIANTS | G0 | 4.32% | 55.83% |
| | G0F | 41.61% | — |
| | MAN-5 | 2.95% | 0.79% |
| | G1 | 1.97% | 24.49% |
| | G1' | 0.84% | 13.73% |
| | G1F | 27.63% | — |
| | G1F' | 12.71% | — |
| | G2 | 0.58 | 5.17% |
| | G2F | 7.39% | — |
| % of Afucosylation | | 10.66% | 100% |

Flow Cytometry

This method provides a means of measuring the ligand binding affinity of Her2 receptors expressed on BT-474, a breast cancer cell line through a flow cytometry-based assay. The level of receptor binding by the biotinylated antibody samples are assessed by probing with FITC labeled Streptavidin and measuring the level of fluorescence using a flow cytometer. The Afucosylated Anti-Her2 Antibody product shows a shift in their peak towards right side in comparison with 'unstained cells only' control indicating the specificity of these samples towards Her2 receptors on breast cancer cells. The overlay data (FIG. 23) of Trastuzumab and Afucosylated Anti-Her2 Antibody is comparable suggesting that the Afucosylated Anti-Her2 Antibody product has similar binding affinity as Trastuzumab. These results also indicate the proper folding, correct assembly and biological activity of produced Afucosylated Anti-Her2 Antibody product.

SPR Data

SPR data (FIG. 24A) reveals comparable binding of HER2 against afucosylated Anti-HER2 antibody product to Trastuzumab. KD value for afucosylated Anti-HER2 antibody is 4.21E-09 (4.2 nM) and for Trastuzumab it is found to be 3.69E-09 (3.6 nM). Association and dissociation (ka and kd) values indicate that Afucosylated Anti HER2 antibody has very strong affinity to HER2 ligand. But for FcγRIII receptor (CD16a ligand), SPR sensorgram exhibits marked difference in binding with Trastuzumab and Afucosylated AntiHer2 Antibody product. The data suggests that Trastuzumab generally havsa very weak binding against FcγRIII receptor (CD16a ligand) and a strong binding with HER2 ligand. While the Afucosylated AntiHer2 Antibody described in this disclosure reveals a significantly higher level of binding with FcγRIII receptor. The kinetics data (FIG. 24B) suggests afucosylated Anti-HER2 antibody (KD 4.00E-08 M) which is nearly three times higher binding affinity than Trastuzumab (KD 1.08E-07 M).

Antiproliferation Assay

The antiproliferation assay (FIG. 25) examined the capability of the drug to inhibit the cell growth of breast cancer cell line. Afucosylated anti-HER2 Antibody shows comparable cytostatic potency (ability of the drug to prevent the cancer cells to proliferate) when compared with the Trastuzumab and the relative potency value shows 85.2% against Trastuzumab. Potency specification for antiproliferation assay is set between 70-130% in parallel line assay calculation software (PLA software).

Antibody Dependent Cellular Cytotoxicity (ADCC)Assay with PBMC Samples

FIG. 26 reveals the biological potential of Afucosylated AntiHer2 Antibody product developed from CHO S cell line overproducing AntiHer2 Antibody and transformed with CRISPR/Cas system targeting FUT8 gene. The Afucosylated AntiHer2 antibody product and Trastuzumab is used to assay the cytotoxity levels at different drug concentrations. Graphpad prism software is used for data analysis. The results suggest more than 8 fold improvement in ADCC with Afucosylated antiHer2 antibody product. This data establishes that afucosylation of monoclonal antibody has a direct influence in biological function of the monoclonal antibody.

Large numbers of tumor antigenic targets are currently being studied for possible monoclonal antibody mediated treatment. Traditional monoclonal antibody therapeutics is developed in CHO S cell expression systems, which has an intrinsic fucosylation activity through fucose biosynthetic pathway.

The methodologies and CRISPR/Cas system described in this disclosure therefore bring novel product development approaches where any monoclonal antibody product which has poor biological efficiency due to fucosylation is significantly improved by developing an afucosylated version of the monoclonal antibody. The novel approaches described here, open up new product development routes to develop afucosylated monoclonal antibodies from existing high expression eukaryotic protein expression platforms.

---

We claim:

1. An antibody producing cell comprising
   a gene encoding an antibody having Antibody-dependent cell-mediated cytotoxicity (ADCC) activity and
   a vector comprising:
   a nucleotide sequence encoding a Clustered Regularly Interspaced Short Palindromic Repeat (CRISPR) RNA (crRNA) consisting of SEQ ID No. 12,
   a nucleotide sequence encoding a crRNA consisting of SEQ ID No. 14,
   a nucleotide sequence encoding tracrRNA, and
   a nucleotide sequence encoding a Cas9n nuclease, wherein the nucleotide sequence encoding the Cas9n nuclease consists of SEQ ID No. 3.

2. The cell as claimed in claim 1, wherein the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

3. The cell as claimed in claim 1, wherein the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from Spodoptera fugiperda (Sf), Pichia, Saccharomyces and Schizosaccharomyces.

4. The cell as claimed in claim 2, wherein the cell is a CHO cell; and wherein the antibody is anti-Her2 antibody.

5. A method of obtaining an antibody producing cell, said method comprising transfecting a cell comprising a gene encoding an antibody having ACDD activity with a vector comprising: a nucleotide sequence encoding a crRNA consisting of SEQ ID NO:12, a nucleotide sequence encoding a crRNA consisting of SEQ ID NO:14, a nucleotide sequence encoding tracrRNA, and a nucleotide sequence encoding a Cas9n nuclease, wherein the nucleotide sequence encoding the Cas9n nuclease consists of SEQ ID No. 3 to obtain the antibody producing cell.

6. The method as claimed in claim 5, wherein the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody;

wherein expression of the crRNAs, the tracrRNA, and the Cas9n nuclease disrupts a Fut8 gene of the cell; and wherein the Fut8 gene sequence is disrupted by cleavage at Exon 7; and wherein the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

7. A method of obtaining an afucosylated antibody having ADCC activity, said method comprising obtaining an antibody expressed by an antibody producing cell, said antibody producing cell comprising:

a gene encoding an antibody having ADCC activity, and a vector comprising:

a nucleotide sequence encoding a crRNA consisting of SEQ ID No. 12, a nucleotide sequence encoding a crRNA consisting of SEQ ID No. 14, a nucleotide sequence encoding tracrRNA, and a nucleotide sequence encoding a Cas9n nuclease, wherein the nucleotide sequence encoding the Cas9n nuclease consists of SEQ ID No. 3.

8. The method as claimed in claim 7, wherein the antibody is selected from the group consisting of anti-CD20 antibody, anti-EGFR antibody, anti-Her2 antibody, anti-CD19 antibody, anti-LAG3 antibody, anti-CD40 antibody, anti-EpHA3 antibody, anti-HIV neutralizing antibody, anti-HCV neutralizing antibody and anti-dengue neutralizing antibody.

9. The method as claimed in claim 7, wherein the antibody producing cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

* * * * *

SEQUENCE LISTING

<160> NUMBER OF SEQ ID NOS: 43

<210> SEQ ID NO 1
<211> LENGTH: 3126
<212> TYPE: DNA
<213> ORGANISM: Cricetulus griseus
<220> FEATURE:
<221> NAME/KEY: Cricetulus griseus Fut8 mRNA
<222> LOCATION: (1)..(3126)

<400> SEQUENCE: 1
caggttgctg ctctggctta ggccatctat gaccctggtg gtgttttcat tcactataag     60
tccttcccat ctttattaac tgagcaagtt cagctagtaa ttttagagac cgaggttcaa    120

| | |
|---|---|
| gcaataacac ctatctctgc aataccgtgt ggctttcttc aatgtcttac atcctaagga | 180 |
| aaggaagcat gtagagccca ggaagcacag gacaagaaag ctgcctcctt gtatcaccag | 240 |
| gaagatcttt ttgtaagagt catcacagta taccagagag actaattttg tctgaagcat | 300 |
| catgtgttga acaacagaa acttattttc ctgtgtggct aactagaacc agagtacaat | 360 |
| gtttccaatt ctttgagctc cgagaagaca gaagggagtt gaaactctga aaatgcgggc | 420 |
| atggactggt tcctggcgtt ggattatgct cattctttt gcctggggga ccttattgtt | 480 |
| ttatataggt ggtcatttgg ttcgagataa tgaccaccct gaccattcta gcagagaact | 540 |
| ctccaagatt cttgcaaagc tggagcgctt aaaacaacaa aatgaagact gaggagaat | 600 |
| ggctgagtct ctccgaatac cagaaggccc tattgatcag gggacagcta caggaagagt | 660 |
| ccgtgtttta gaagaacagc ttgttaaggc caaagaacag attgaaaatt acaagaaaca | 720 |
| agctaggaat gatctgggaa aggatcatga atcttaagg aggaggattg aaaatggagc | 780 |
| taaagagctc tggtttttc tacaaagtga attgaagaaa ttaagaaat tagaaggaaa | 840 |
| cgaactccaa agacatgcag atgaaattct tttggattta ggacatcatg aaaggtctat | 900 |
| catgacagat ctatactacc tcagtcaaac agatggagca ggtgagtggc gggaaaaaga | 960 |
| agccaaagat ctgacagagc tggtccagcg gagaataaca tatctgcaga atcccaagga | 1020 |
| ctgcagcaaa gccagaaagc tggtatgtaa tatcaacaaa ggctgtggct atggatgtca | 1080 |
| actccatcat gtggttact gcttcatgat tgcttatggc acccagcgaa cactcatctt | 1140 |
| ggaatctcag aattggcgct atgctactgg aggatgggag actgtgttta gacctgtaag | 1200 |
| tgagacatgc acagacaggt ctggcctctc cactggacac tggtcaggtg aagtgaagga | 1260 |
| caaaaatgtt caagtggtcg agctcccat gtagacagc ctccatcctc gtcctcctta | 1320 |
| cttacccttg gctgtaccag aagacttgc agatcgactc ctgagagtcc atggtgatcc | 1380 |
| tgcagtgtgg tgggtatccc agtttgtcaa atacttgatc cgtccacaac cttggctgga | 1440 |
| aagggaaata gaagaaacca ccaagaagct tggcttcaaa catccagtta ttggagtcca | 1500 |
| tgtcagacgc actgacaaag tgggaacaga agcagccttc catcccattg aggaatacat | 1560 |
| ggtacacgtt gaagaacatt ttcagcttct cgaacgcaga atgaaagtgg ataaaaaaag | 1620 |
| agtgtatctg ccactgatg acccttcttt gttaaggag gcaaagacaa agtactccaa | 1680 |
| ttatgaattt attagtgata actctatttc ttggtcagct ggactacaca accgatacac | 1740 |
| agaaaattca cttcggggcg tgatcctgga tatacacttt ctctcccagg ctgacttcct | 1800 |
| tgtgtgtact ttttcatccc aggtctgtag ggttgcttat gaaatcatgc aaacactgca | 1860 |
| tcctgatgcc tctgcaaact tccattcttt agatgacatc tactattttg gaggccaaaa | 1920 |
| tgcccacaac cagattgcag tttatcctca ccaacctcga actaaagagg aaatcccat | 1980 |
| ggaacctgga gatatcattg gtgtggctgg aaaccattgg aatggttact ctaaaggtgt | 2040 |
| caacagaaaa ctaggaaaaa caggcctgta cccttcctac aaagtccgag agaagataga | 2100 |
| aacagtcaaa taccctacat atcctgaagc tgaaaaatag atgggagtg taagagatta | 2160 |
| acaacagaat ttagttcaga ccatctcagc caagcagaag acccagacta acatatggtt | 2220 |
| cattgacaga catgctccgc accaagagca agtgggaacc ctcagatgct gcactggtgg | 2280 |
| aacgcctctt tgtgaagggc tgctgtgccc tcaagcccat gcacagtaaa ataatgtact | 2340 |
| cacacataac atacaaatgg attatttct actttgccct ttaaatattc tgtccccatg | 2400 |
| aaacaaaac tgccacatta tgtaatttaa gtgacacaga cgttttgtgt gagacttcaa | 2460 |
| acatggtgcc tatatctgag agacctctgt gatttactga gaagatgaga acagctccct | 2520 |

-continued

```
tctgtgggga agttggttct tagtcagtgg tggactggcc actgaattca ctgcaatcaa    2580
cagattcaga atgagaatgg atgttttttcc tttatatggt tgtctggatt ttttttaaag    2640
taatttcatc agttcagttc atccacctca ttaataaatg aaggaatata ccaataaaat    2700
caaatgaaat attcactgtc cattaggaag ttttataaaa caatgccatg aacaaaaaat    2760
tctttagtac tcaatgtttc tggacattct ctttgataac aaaaataaat tttaaaagg    2820 aattttgtaa agtttctggg attctgtatc actggatgat gtagttataa gctttgtagt    2880
agaaatatgg gaagtgggtt tatagctttt aagatttttt tctacttttg tcctactttt    2940
tctatttctg atagaataat catatttcaa gagaagcatt ggtcccctct aatactagta    3000 actgcctta gtcatgcata ttatatgaag ttgctaagaa cacgctttgg gggaggtgtt    3060
cactctctta gtttgatatt gttgacttga tataattgaa tgaaatagtc attctcttgc    3120
ttccag                                                               3126
```

<210> SEQ ID NO 2
<211> LENGTH: 4101
<212> TYPE: DNA
<213> ORGANISM: Streptococcus pyogenes
<220> FEATURE:
<221> NAME/KEY: Cas9 nucleotide sequence
<222> LOCATION: (1)..(4101)

<400> SEQUENCE: 2

```
gacaagaagt acagcatcgg cctggccatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca cggcgaaac agccgaggcc     180 acccggctga gagaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaacccatc     600 aacgccagcg gcgtggacgc caaggccatc ctgtctgcca ctgagcaa gagcagacgg     660 ctggaaaatc tgatcgccca gctgcccggc gagaagaaga tggcctgtt cggaaacctg     720 attgccctga gcctgggcct gaccccaac ttcaagagca cttcgacct ggccgaggat     780 gccaaactgc agctgagcaa ggacacctac gacgacgacc tggacaacct gctggcccag     840
atcggcgacc agtacgccga cctgtttctg gccgccaaga acctgtccga cgccatcctg     900
ctgagcgaca tcctgagagt gaacaccgag atcaccaagg ccccctgag cgcctctatg     960 atcaagagat acgacgagca ccaccaggac ctgaccctgc tgaaagctct cgtgcggcag    1020
cagctgcctg agaagtacaa agagattttc ttcgaccaga gcaagaacgg ctacgccggc    1080
tacattgacg gcggagccag ccaggaagag ttctacaagt tcatcaagcc catcctggaa    1140
aagatggacg gcaccgagga actgctcgtg aagctgaaca gagaggacct gctgcggaag    1200
cagcggacct tcgacaacgg cagcatcccc caccagatcc acctgggaga gctgcacgcc    1260
attctgcggc ggcaggaaga ttttttaccca ttcctgaagg acaaccggga aaagatcgag    1320
aagatcctga ccttccgcat cccctactac gtgggccctc tggccagggg aaacagcaga    1380
```

```
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga agaggactac cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa acgaggacat tctggaagaa tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctttta agaggacat ccagaaagcc caggtgtccg ccagggcga tagcctgcac   2160 gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga gaacagccg cgagagaatg   2340 aagcggatcg aagagggcat caaagagctg ggcagccaga tcctgaaaga cacccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca gtacttcttt ctacagcaac   3120
atcatgaact ttttcaagac cgagattacc ctggccaacg gcgagatccg gaagcggcct   3180
ctgatcgaga caaacggcga aaccggggag atcgtgtggg ataagggccg ggattttgcc   3240
accgtgcgga aagtgctgag catgccccaa gtgaatatcg tgaaaaagac cgaggtgcag   3300
acaggcggct tcagcaaaga gtctatcctg cccaagagga cagcgataa gctgatcgcc   3360 agaaagaagg actgggaccc taagaagtac ggcggcttcg acagccccac cgtggcctat   3420
tctgtgctgg tggtggccaa agtggaaaag ggcaagtcca agaaactgaa gagtgtgaaa   3480
gagctgctgg gatcaccat catggaaaga agcagcttcg agaagaatcc catcgacttt   3540
ctggaagcca gggctacaa agaagtgaaa aaggacctga tcatcaagct gcctaagtac   3600
tccctgttcg agctggaaaa cggccggaag agaatgctgg cctctgccgg cgaactgcag   3660
aagggaaacg aactggccct gccctccaaa tatgtgaact tcctgtacct ggccagccac   3720
```

| | |
|---|---|
| tatgagaagc tgaagggctc ccccgaggat aatgagcaga acagctgtt tgtggaacag | 3780 |
| cacaagcact acctggacga gatcatcgag cagatcagcg agttctccaa gagagtgatc | 3840 |
| ctggccgacg ctaatctgga caaagtgctg tccgcctaca caagcaccg ggataagccc | 3900 |
| atcagagagc aggccgagaa tatcatccac ctgtttaccc tgaccaatct gggagcccct | 3960 |
| gccgccttca gtactttga caccaccatc gaccggaaga ggtacaccag caccaaagag | 4020 |
| gtgctggacg ccaccctgat ccaccagagc atcaccggcc tgtacgagac acggatcgac | 4080 |
| ctgtctcagc tgggaggcga c | 4101 |

<210> SEQ ID NO 3
<211> LENGTH: 4101
<212> TYPE: DNA
<213> ORGANISM: Streptococcus pyogenes
<220> FEATURE:
<221> NAME/KEY: Cas9n nucleotide sequence
<222> LOCATION: (1)..(4101)

<400> SEQUENCE: 3

| | |
|---|---|
| gacaagaagt acagcatcgg cctggccatc ggcaccaact ctgtgggctg ggccgtgatc | 60 |
| accgacgagt acaaggtgcc cagcaagaaa ttcaaggtgc tgggcaacac cgaccggcac | 120 |
| agcatcaaga gaacctgat cggagccctg ctgttcgaca cggcgaaac agccgaggcc | 180 |
| acccggctga gagaaccgc cagaagaaga tacaccagac ggaagaaccg gatctgctat | 240 |
| ctgcaagaga tcttcagcaa cgagatggcc aaggtggacg acagcttctt ccacagactg | 300 |
| gaagagtcct tcctggtgga agaggataag aagcacgagc ggcacccat cttcggcaac | 360 |
| atcgtggacg aggtggccta ccacgagaag taccccacca tctaccacct gagaaagaaa | 420 |
| ctggtggaca gcaccgacaa ggccgacctg cggctgatct atctggccct ggcccacatg | 480 |
| atcaagttcc ggggccactt cctgatcgag gcgacctga ccccgacaa cagcgacgtg | 540 |
| gacaagctgt tcatccagct ggtgcagacc tacaaccagc tgttcgagga aaaccccatc | 600 |
| aacgccagcg gcgtggacgc caaggccatc ctgtctgcca gactgagcaa gagcagacgg | 660 |
| ctggaaaatc tgatcgccca gctgcccggc gagaagaaga tggcctgtt cggaaacctg | 720 |
| attgccctga gcctgggcct gaccccaac ttcaagagca cttcgacct ggccgaggat | 780 |
| gccaaactgc agctgagcaa ggacacctac gacgacgacc tggacaacct gctggcccag | 840 |
| atcggcgacc agtacgccga cctgtttctg gccgccaaga acctgtccga cgccatcctg | 900 |
| ctgagcgaca tcctgagagt gaacaccgag atcaccaagg cccccctgag cgcctctatg | 960 |
| atcaagagat acgacgagca ccaccaggac ctgaccctgc tgaaagctct cgtgcggcag | 1020 |
| cagctgcctg agaagtacaa agagattttc ttcgaccaga gcaagaacgg ctacgccggc | 1080 |
| tacattgacg gcggagccag ccaggaagag ttctacaagt tcatcaagcc catcctggaa | 1140 |
| aagatggacg gcaccgagga actgctcgtg aagctgaaca gagaggacct gctgcggaag | 1200 |
| cagcggacct tcgacaacgg cagcatcccc caccagatcc acctgggaga gctgcacgcc | 1260 |
| attctgcggc ggcaggaaga ttttttaccca ttcctgaagg acaaccggga aaagatcgag | 1320 |
| aagatcctga ccttccgcat cccctactac gtgggccctc tggccagggg aaacagcaga | 1380 |
| ttcgcctgga tgaccagaaa gagcgaggaa accatcaccc cctggaactt cgaggaagtg | 1440 |
| gtggacaagg gcgcttccgc ccagagcttc atcgagcgga tgaccaactt cgataagaac | 1500 |
| ctgcccaacg agaaggtgct gcccaagcac agcctgctgt acgagtactt caccgtgtat | 1560 |
| aacgagctga ccaaagtgaa atacgtgacc gagggaatga gaaagccggc cttcctgagc | 1620 |

```
ggcgagcaga aaaaggccat cgtggacctg ctgttcaaga ccaaccggaa agtgaccgtg    1680
aagcagctga agaggactac cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa acgaggacac ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100
ctgaccttta agaggacatc ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccacccag aagggacaga gaacagccg cgagagaatg    2340 aagcggatcg aagagggcat caaagagctg ggcagccaga tcctgaaaga caccccgtg    2400 gaaaacaccc agctgcagaa cgagaagctg tacctgtact acctgcagaa tgggcgggat    2460
atgtacgtgg accaggaact ggacatcaac cggctgtccg actacgatgt ggaccatatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga aaagttcga caatctgacc    2700 aaggccgaga gaggcggcct gagcgaactg gataaggccg gcttcatcaa gagacagctg    2760
gtggaaaccc ggcagatcac aaagcacgtg gcacagatcc tggactccg gatgaacact    2820 aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact tttcaagac cgagattacc ctggccaacg gcgagatccg gaagcggcct    3180
ctgatcgaga caaacggcga aaccggggag atcgtgtggg ataagggccg ggatttgcc    3240 accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagccccac cgtggcctat    3420
tctgtgctgg tggtggccaa agtggaaaag ggcaagtcca gaaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gcctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagccct    3960 gccgccttca gtactttga caccaccatc gaccggaaga ggtacaccag caccaaagag    4020
```

```
gtgctggacg ccaccctgat ccaccagagc atcaccggcc tgtacgagac acggatcgac    4080
ctgtctcagc tgggaggcga c                                              4101
```

<210> SEQ ID NO 4
<211> LENGTH: 238
<212> TYPE: DNA
<213> ORGANISM: Cricetulus griseus
<220> FEATURE:
<221> NAME/KEY: Fut8 Exon 7 nucleotide sequence
<222> LOCATION: (1)..(238)

<400> SEQUENCE: 4

```
aatcccaagg actgcagcaa agccagaaag ctggtatgta atatcaacaa aggctgtggc      60
tatggatgtc aactccatca tgtggtttac tgcttcatga ttgcttatgg cacccagcga     120
acactcatct tggaatctca gaattggcgc tatgctactg gaggatggga gactgtgttt    180
agacctgtaa gtgagacatg cacagacagg tctggcctct ccactggaca ctggtcag      238
```

<210> SEQ ID NO 5
<211> LENGTH: 79
<212> TYPE: PRT
<213> ORGANISM: Cricetulus griseus
<220> FEATURE:
<221> NAME/KEY: Fut8 Exon 7 amino acid sequence
<222> LOCATION: (1)..(79)

<400> SEQUENCE: 5

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Ile Leu Glu Ser Gln Asn
        35                  40                  45

Trp Arg Tyr Ala Thr Gly Gly Trp Glu Thr Val Phe Arg Pro Val Ser
    50                  55                  60

Glu Thr Cys Thr Asp Arg Ser Gly Leu Ser Thr Gly His Trp Ser
65                  70                  75
```

<210> SEQ ID NO 6
<211> LENGTH: 20
<212> TYPE: DNA
<213> ORGANISM: Artificial Sequence
<220> FEATURE:
<223> OTHER INFORMATION: CRISPR recognition sequence 1

<400> SEQUENCE: 6

```
aattggcgct atgctactgg                                                 20
```

<210> SEQ ID NO 7
<211> LENGTH: 23
<212> TYPE: RNA
<213> ORGANISM: Artificial Sequence
<220> FEATURE:
<223> OTHER INFORMATION: gRNA1

<400> SEQUENCE: 7

```
aauuggcgcu augcuacugg agg                                             23
```

<210> SEQ ID NO 8
<211> LENGTH: 23
<212> TYPE: DNA
<213> ORGANISM: Artificial Sequence -continued

```
<220> FEATURE:
<223> OTHER INFORMATION: CRISPR recognition sequence 2

<400> SEQUENCE: 8
ccagcgaaca ctcatcttgg aat                                                  23

<210> SEQ ID NO 9
<211> LENGTH: 23
<212> TYPE: RNA
<213> ORGANISM: Artificial Sequence
<220> FEATURE:
<223> OTHER INFORMATION: gRNA2

<400> SEQUENCE: 9
ccagcgaaca cucaucuugg aau                                                  23

<210> SEQ ID NO 10
<211> LENGTH: 499
<212> TYPE: DNA
<213> ORGANISM: Artificial Sequence
<220> FEATURE:
<223> OTHER INFORMATION: gRNA + scaffold for Fut8 Exon 7
<220> FEATURE:
<221> NAME/KEY: misc_feature
<222> LOCATION: (1)..(499)

<400> SEQUENCE: 10
attccaagat gagtgttcgc gttttagagc tagaaatagc aagttaaaat aaggctagtc          60
cgttatcaac ttgaaaaagt ggcaccgagt cggtgctttt ttgctccgcg gcacgagaac         120
tcaaagcccc ggggcctggg tcccacgcgg ggtcccttac ccagggtgcc ccgggcgctc         180
atttgcatgt cccacccaac aggtaaacct gacaggtcat cgcggccagg tacgacctgg         240
cggtcagagc accaaacata cgagccttgt gatgagttcc gttgcatgaa attctcccaa         300
aggctccaag atggacagga aagggcgcgg ttcggtcacc gtaagtagaa taggtgaaag         360
actcccgtgc cttataaggc ctgtgggtga cttcttctca ccgaattggc gctatgctac         420
tgggttttag agctagaaat agcaagttaa ataaggctag tccgttatc aacttgaaaa         480 agtggcaccg agtcggtgc                                                     499

<210> SEQ ID NO 11
<211> LENGTH: 20
<212> TYPE: DNA
<213> ORGANISM: Artificial Sequence
<220> FEATURE:
<223> OTHER INFORMATION: CRISPR DNA binding domain 1

<400> SEQUENCE: 11
attccaagat gagtgttcgc                                                     20

<210> SEQ ID NO 12
<211> LENGTH: 20
<212> TYPE: RNA
<213> ORGANISM: Artificial Sequence
<220> FEATURE:
<223> OTHER INFORMATION: Target specific crRNA sequence

<400> SEQUENCE: 12
auuccaagau gaguguucgc                                                     20

<210> SEQ ID NO 13
<211> LENGTH: 20
<212> TYPE: DNA
<213> ORGANISM: Artificial Sequence
```

```
<220> FEATURE:
<223> OTHER INFORMATION: DNA Binding domain 2

<400> SEQUENCE: 13
aattggcgct atgctactgg                                              20

<210> SEQ ID NO 14
<211> LENGTH: 20
<212> TYPE: RNA
<213> ORGANISM: Artificial Sequence
<220> FEATURE:
<223> OTHER INFORMATION: Target specific crRNA sequence

<400> SEQUENCE: 14
aauuggcgcu augcuacugg                                              20

<210> SEQ ID NO 15
<211> LENGTH: 76
<212> TYPE: DNA
<213> ORGANISM: Artificial Sequence
<220> FEATURE:
<223> OTHER INFORMATION: gRNA scaffold

<400> SEQUENCE: 15
gttttagagc tagaaatagc aagttaaaat aaggctagtc cgttatcaac ttgaaaaagt   60
ggcaccgagt cggtgc                                                  76

<210> SEQ ID NO 16
<211> LENGTH: 469
<212> TYPE: PRT
<213> ORGANISM: Artificial Sequence
<220> FEATURE:
<223> OTHER INFORMATION: Anti-her2 antibody heavy chain amino acid
      sequence

<400> SEQUENCE: 16
```

Met Gly Trp Ser Cys Ile Ile Leu Phe Leu Val Ala Thr Ala Thr Gly
 1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly Lys
465

<210> SEQ ID NO 17
<211> LENGTH: 233
<212> TYPE: PRT
<213> ORGANISM: Artificial Sequence
<220> FEATURE:
<223> OTHER INFORMATION: Antiher2 antibody light chain amino acid
      sequence

<400> SEQUENCE: 17

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Val
        35                  40                  45

Asn Thr Ala Val Ala Trp Tyr Gln Gln Lys Pro Gly Lys Ala Pro Lys
    50                  55                  60

Leu Leu Ile Tyr Ser Ala Ser Phe Leu Tyr Ser Gly Val Pro Ser Arg

```
                65                  70                  75                  80
Phe Ser Gly Ser Arg Ser Gly Thr Asp Phe Thr Leu Thr Ile Ser Ser
                    85                  90                  95

Leu Gln Pro Glu Asp Phe Ala Thr Tyr Tyr Cys Gln Gln His Tyr Thr
                100                 105                 110

Thr Pro Pro Thr Phe Gly Gln Gly Thr Lys Val Glu Ile Lys Arg Thr
                115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 18
<211> LENGTH: 26
<212> TYPE: DNA
<213> ORGANISM: Artificial Sequence
<220> FEATURE:
<223> OTHER INFORMATION: FORWARD PRIMER

<400> SEQUENCE: 18
aagaaataag ctgaatcagc tctgac                                            26

<210> SEQ ID NO 19
<211> LENGTH: 23
<212> TYPE: DNA
<213> ORGANISM: Artificial Sequence
<220> FEATURE:
<223> OTHER INFORMATION: REVERSE PRIMER

<400> SEQUENCE: 19
gtgctaatct gacctaacca gag                                               23

<210> SEQ ID NO 20
<211> LENGTH: 394
<212> TYPE: DNA
<213> ORGANISM: Cricetulus griseus
<220> FEATURE:
<221> NAME/KEY: Fut8 Exon 7 and associated intron sequences
<222> LOCATION: (1)..(394)

<400> SEQUENCE: 20
aagaaataag ctgaatcagc tctgacttat tgtgtgattt tcaatacctg tgaccaaaat      60
gagaagttaa ctccttatat ctttatctta tttgtttctc tggaagaatc ccaaggactg     120
cagcaaagcc agaaagctgg tatgtaatat caacaaaggc tgtggctatg gatgtcaact     180
ccatcatgtg gtttactgct tcatgattgc ttatggcacc cagcgaacac tcatcttgga     240
atctcagaat ggcgctatg ctactggagg atgggagact gtgtttagac ctgtaagtga     300
gacatgcaca gacaggtctg gcctctccac tggacactgg tcaggtaagg agcatgtgca     360
```

```
ccatgaaaga tctctggtta ggtcagatta gcac                              394
```

<210> SEQ ID NO 21
<211> LENGTH: 189
<212> TYPE: DNA
<213> ORGANISM: Cricetulus griseus
<220> FEATURE:
<221> NAME/KEY: Clone CR2TMCHO 1A allelic version
<222> LOCATION: (1)..(189)

<400> SEQUENCE: 21

```
aatcccaagg actgcagcaa agccagaaag ctggtatgta atatcaacaa aggctgtggc    60
tatggatgtc aactccatca tgtggtttac tgcttcatga ttgcttatgg cacccagcga   120
acactctgtt tagacctgta agtgagacat gcacagacag gtctggcctc tccactggac   180
actggtcag                                                           189
```

<210> SEQ ID NO 22
<211> LENGTH: 697
<212> TYPE: DNA
<213> ORGANISM: Cricetulus griseus
<220> FEATURE:
<221> NAME/KEY: Clone CR2TMCHO 1A allelic version
<222> LOCATION: (1)..(697)

<400> SEQUENCE: 22

```
aatcccaagg actgcagcaa agccagaaag ctggtatgta atatcaacaa aggctgtggc    60
tatggatgtc aactccatca tgtggtttac tgcttcatga ctcacgggga tttccaagtc   120
tccaccccat tgacgtcaat gggagtttgt tttggcacca aaatcaacgg gactttccaa   180
aatgtcgtaa taaccccgcc ccgttgacgc aaatgggcgg taggcgtgta cggtgggagg   240
tctatataag cagagctcgt ttagtgaacc gtcagatcac tagaagcttt attgcggtag   300
tttatcacag ttaaattgct aacgcagtca ggccaacaga gaccacaccc aagctggccg   360
ccaccatggc cccaaagaag aagcggaagg tcggtatcca cggagtccca gcagccgaca   420
agaagtacag catcggcctg gccatcggca ccaactctgt gggctgggcc gtgatcaccg   480
acgagtacaa ggtgcccagc aagaaattca aggtgctggg caacaccgac cggcacagca   540
tcaagaagaa cctgatcgga gccctgctgt tcgacagcgg cgaaacagcc gaggccaccc   600
ggctgaagag aaccgccaga aggatgggag actgtgttta gacctgtaag tgagacatgc   660
acagacaggt ctggcctctc cactggacac tggtcag                            697
```

<210> SEQ ID NO 23
<211> LENGTH: 417
<212> TYPE: DNA
<213> ORGANISM: Cricetulus griseus
<220> FEATURE:
<221> NAME/KEY: Clone CR2TMCHO 1B allelic version
<222> LOCATION: (1)..(417)

<400> SEQUENCE: 23

```
aatcccaagg actgcagcaa agccagaaag ctggtatgta atatcaacaa aggctgtggc    60
tatggatgtc aactccatca tgtggtttac tgcttcatga ttgcttatgg cacccagcga   120
acactcatct ggaggatggg agactgtgtt tagacctgta agtgagacat gcacagacag   180
gtctggcctc tccactggac actggtcaaa tcccaaggac tgcagcaaag ccagaaagct   240
ggtatgtaat atcaacaaag gctgtggcta tggatgtcaa ctccatcatg tggtttactg   300
cttcatgatt gcttatggca cccagcgaac actcatctgg aggatgggag actgtgttta   360
```

```
gacctgtaag tgagacatgc acagacaggt ctggcctctc cactggacac tggtcag         417
```

<210> SEQ ID NO 24
<211> LENGTH: 378
<212> TYPE: DNA
<213> ORGANISM: Cricetulus griseus
<220> FEATURE:
<221> NAME/KEY: Clone CR2TMCHO 1B allelic version
<222> LOCATION: (1)..(378)

<400> SEQUENCE: 24

```
aatcccaagg actgcagcaa agccagaaag ctggtatgta atatcaacaa aggctgtggc          60
tatggatgtc aactccatca tgtggtttac tgcttcatga ttgcttatgg cacccagttg         120
cctaatagaa caacctttgc ctggttgtta caaatatat tctctgtacc agtatctagt         180
tttacaatga gctatggaat gttaatgatt tatttgtcta cattataaat tatattgctt         240
tgatttgctc taagtggaac aaacactcat cttggaatct cagaattggc gctatgctac         300
tggaggatgg gagactgtgt ttagacctgt aagtgagaca tgcacagaca ggtctggcct         360
ctccactgga cactggtc                                                      378
```

<210> SEQ ID NO 25
<211> LENGTH: 46
<212> TYPE: PRT
<213> ORGANISM: Cricetulus griseus
<220> FEATURE:
<221> NAME/KEY: Frame shift with STOP CODON
<222> LOCATION: (1)..(46Frame shift with STOP CODON)

<400> SEQUENCE: 25

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Cys Leu Asp Leu
        35                  40                  45
```

<210> SEQ ID NO 26
<211> LENGTH: 68
<212> TYPE: PRT
<213> ORGANISM: Cricetulus griseus
<220> FEATURE:
<221> NAME/KEY: Frame shift with STOP CODON
<222> LOCATION: (1)..(68)

<400> SEQUENCE: 26

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Thr His Gly Asp Phe Gln Val Ser Thr Pro Leu Thr Ser Met Gly
        35                  40                  45

Val Cys Phe Gly Thr Lys Ile Asn Gly Thr Phe Gln Asn Val Val Ile
    50                  55                  60

Thr Pro Pro Arg
65
```

<210> SEQ ID NO 27
<211> LENGTH: 50
<212> TYPE: PRT
<213> ORGANISM: Cricetulus griseus
<220> FEATURE:

<221> NAME/KEY: Frame shift with STOP CODON
<222> LOCATION: (1)..(50)

<400> SEQUENCE: 27

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Ile Trp Arg Met Gly Asp
        35                  40                  45

Cys Val
    50

<210> SEQ ID NO 28
<211> LENGTH: 75
<212> TYPE: PRT
<213> ORGANISM: Cricetulus griseus
<220> FEATURE:
<221> NAME/KEY: Frame shift with STOP CODON
<222> LOCATION: (1)..(75)

<400> SEQUENCE: 28

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Leu Pro Asn Arg Thr Thr Phe Ala Trp
        35                  40                  45

Leu Leu Gln Asn Ile Phe Ser Val Pro Val Ser Ser Phe Thr Met Ser
    50                  55                  60

Tyr Gly Met Leu Met Ile Tyr Leu Ser Thr Leu
65                  70                  75

<210> SEQ ID NO 29
<211> LENGTH: 325
<212> TYPE: DNA
<213> ORGANISM: Cricetulus griseus
<220> FEATURE:
<221> NAME/KEY: gene
<222> LOCATION: (1)..(325)
<223> OTHER INFORMATION: FUT8 exon 7 genomic locus

<400> SEQUENCE: 29
agagctggtc cagcggagaa taacatatct gcagaatccc aaggactgca gcaaagccag      60
aaagctggta tgtaatatca acaaaggctg tggctatgga tgtcaactcc atcatgtggt    120
ttactgcttc atgattgctt atggcaccca gcgaacactc atcttggaat ctcagaattg    180
gcgctatgct actggaggat gggagactgt gtttagacct gtaagtgaga catgcacaga    240
caggtctggc ctctccactg gacactggtc aggtgaagtg aaggacaaaa atgttcaagt    300
ggtcgagctc cccattgtag acagc                                          325

<210> SEQ ID NO 30
<211> LENGTH: 575
<212> TYPE: PRT
<213> ORGANISM: Cricetulus griseus
<220> FEATURE:
<221> NAME/KEY: PEPTIDE
<222> LOCATION: (1)..(575)
<223> OTHER INFORMATION: Fut8 full length amino acid sequence

<400> SEQUENCE: 30

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Ile Glu Asn Gly Ala Lys Glu Leu Trp Phe
            115                 120                 125

Phe Leu Gln Ser Glu Leu Lys Lys Leu Lys Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Thr Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
```

```
                420             425             430
Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Gln Pro Arg Thr Lys Glu Glu Ile Pro Met Glu Pro Gly Asp Ile
            515                 520                 525

Ile Gly Val Ala Gly Asn His Trp Asn Gly Tyr Ser Lys Gly Val Asn
            530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 31
<211> LENGTH: 150
<212> TYPE: DNA
<213> ORGANISM: Cricetulus griseus
<220> FEATURE:
<221> NAME/KEY: Part of CHOS FUT8 Exon 7 sequence depicted in figure 8A
<222> LOCATION: (1)..(150)

<400> SEQUENCE: 31
ccatcatgtg gtttactgct tcatgattgc ttatggcacc cagcgaacac tcatcttgga      60
atctcagaat tggcgctatg ctactggagg atgggagact gtgtttagac ctgtaagtga     120
gacatgcaca gacaggtctg gcctctccac                                      150

<210> SEQ ID NO 32
<211> LENGTH: 609
<212> TYPE: DNA
<213> ORGANISM: Cricetulus griseus
<220> FEATURE:
<221> NAME/KEY: Part of CR2TMCHO1A clone allelic version sequence
      depicted in figure 8A
<222> LOCATION: (1)..(609)

<400> SEQUENCE: 32
ccatcatgtg gtttactgct tcatgactca cggggatttc caagtctcca ccccattgac      60
gtcaatggga gtttgttttg gcaccaaaat caacgggact ttccaaaatg tcgtaataac     120
cccgccccgt tgacgcaaat gggcggtagg cgtgtacggt gggaggtcta tataagcaga     180
gctcgtttag tgaaccgtca gatcactaga agctttattg cggtagttta tcacagttaa     240
attgctaacg cagtcaggcc aacagagacc acacccaagc tggccgccac catggcccca     300
aagaagaagc ggaaggtcgg tatccacgga gtcccagcag ccgacaagaa gtacagcatc     360
ggcctggcca tcggcaccaa ctctgtgggc tgggccgtga tcaccgacga gtacaaggtg     420
cccagcaaga aattcaaggt gctgggcaac accgaccggc acagcatcaa gaagaacctg     480
atcggagccc tgctgttcga cagcggcgaa acagccgagg ccaccgggct gaagagaacc     540
gccagaagga tgggagactg tgtttagacc tgtaagtgag acatgcacag acaggtctgg     600
cctctccac                                                            609
```

<210> SEQ ID NO 33
<211> LENGTH: 292
<212> TYPE: DNA
<213> ORGANISM: Cricetulus griseus
<220> FEATURE:
<221> NAME/KEY: Part of CR2TMCHO1B clone allelic version sequence
      depicted in figure 8A
<222> LOCATION: (1)..(292)

<400> SEQUENCE: 33
ccatcatgtg gtttactgct tcatgattgc ttatggcacc cagttgccta atagaacaac      60 cttttgcctgg ttgttacaaa atatattctc tgtaccagta tctagtttta caatgagcta    120
tggaatgtta atgatttatt tgtctacatt ataaattata ttgctttgat ttgctctaag    180
tggaacaaac actcatcttg aatctcaga attggcgcta tgctactgga ggatgggaga     240
ctgtgtttag acctgtaagt gagacatgca cagacaggtc tggcctctcc ac             292

<210> SEQ ID NO 34
<211> LENGTH: 101
<212> TYPE: DNA
<213> ORGANISM: Cricetulus griseus
<220> FEATURE:
<221> NAME/KEY: Part of CR2TMCHO1A clone allelic version sequence
      depicted in figure 8B
<222> LOCATION: (1)..(101)

<400> SEQUENCE: 34
ccatcatgtg gtttactgct tcatgattgc ttatggcacc cagcgaacac tctgtttaga      60
cctgtaagtg agacatgcac agacaggtct ggcctctcca c                         101

<210> SEQ ID NO 35
<211> LENGTH: 121
<212> TYPE: DNA
<213> ORGANISM: Cricetulus griseus
<220> FEATURE:
<221> NAME/KEY: Part of CR2TMCHO1B clone allelic version sequence
      depicted in figure 8B
<222> LOCATION: (1)..(121)

<400> SEQUENCE: 35
ccatcatgtg gtttactgct tcatgattgc ttatggcacc cagcgaacac tcatctggag      60
gatgggagac tgtgtttaga cctgtaagtg agacatgcac agacaggtct ggcctctcca    120
c                                                                     121

<210> SEQ ID NO 36
<211> LENGTH: 59
<212> TYPE: PRT
<213> ORGANISM: Cricetulus griseus
<220> FEATURE:
<221> NAME/KEY: Part of CHOS FUT8 Exon 7 amino acid sequence depicted in
      figure 9
<222> LOCATION: (1)..(59)

<400> SEQUENCE: 36

Tyr Gly Cys Gln Leu His His Val Val Tyr Cys Phe Met Ile Ala Tyr
1               5                   10                  15

Gly Thr Gln Arg Thr Leu Ile Leu Glu Ser Gln Asn Trp Arg Tyr Ala
            20                  25                  30

Thr Gly Gly Trp Glu Thr Val Phe Arg Pro Val Ser Glu Thr Cys Thr
        35                  40                  45

Asp Arg Ser Gly Leu Ser Thr Gly His Trp Ser

<210> SEQ ID NO 37
<211> LENGTH: 26
<212> TYPE: PRT
<213> ORGANISM: Cricetulus griseus
<220> FEATURE:
<221> NAME/KEY: Part of CR2TMCHO1A clone allelic version amino acid
      sequence depicted in figure 9
<222> LOCATION: (1)..(26)

<400> SEQUENCE: 37

Tyr Gly Cys Gln Leu His His Val Val Tyr Cys Phe Met Ile Ala Tyr
1               5                   10                  15

Gly Thr Gln Arg Thr Leu Cys Leu Asp Leu
            20                  25

<210> SEQ ID NO 38
<211> LENGTH: 30
<212> TYPE: PRT
<213> ORGANISM: Cricetulus griseus
<220> FEATURE:
<221> NAME/KEY: Part of CR2TMCHO1B clone allelic version amino acid
      sequence depicted in figure 9
<222> LOCATION: (1)..(30)

<400> SEQUENCE: 38

Tyr Gly Cys Gln Leu His His Val Val Tyr Cys Phe Met Ile Ala Tyr
1               5                   10                  15

Gly Thr Gln Arg Thr Leu Ile Trp Arg Met Gly Asp Cys Val
            20                  25                  30

<210> SEQ ID NO 39
<211> LENGTH: 55
<212> TYPE: PRT
<213> ORGANISM: Cricetulus griseus
<220> FEATURE:
<221> NAME/KEY: Part of CR2TMCHO1B clone allelic version amino acid
      sequence variant depicted in figure 9
<222> LOCATION: (1)..(55)

<400> SEQUENCE: 39

Tyr Gly Cys Gln Leu His His Val Val Tyr Cys Phe Met Ile Ala Tyr
1               5                   10                  15

Gly Thr Gln Leu Pro Asn Arg Thr Thr Phe Ala Trp Leu Leu Gln Asn
            20                  25                  30

Ile Phe Ser Val Pro Val Ser Ser Phe Thr Met Ser Tyr Gly Met Leu
        35                  40                  45

Met Ile Tyr Leu Ser Thr Leu
50                  55

<210> SEQ ID NO 40
<211> LENGTH: 48
<212> TYPE: PRT
<213> ORGANISM: Cricetulus griseus
<220> FEATURE:
<221> NAME/KEY: Part of CR2TMCHO1A clone allelic version amino acid
      sequence variant depicted in figure 9
<222> LOCATION: (1)..(48)

<400> SEQUENCE: 40

Tyr Gly Cys Gln Leu His His Val Val Tyr Cys Phe Met Thr His Gly
1               5                   10                  15

Asp Phe Gln Val Ser Thr Pro Leu Thr Ser Met Gly Val Cys Phe Gly
            20                  25                  30

```
Thr Lys Ile Asn Gly Thr Phe Gln Asn Val Val Ile Thr Pro Pro Arg
        35                  40                  45

<210> SEQ ID NO 41
<211> LENGTH: 57
<212> TYPE: DNA
<213> ORGANISM: Cricetulus griseus
<220> FEATURE:
<221> NAME/KEY: Sequence in figure 3B containing CRISPR recognition seqs
      of the invention
<222> LOCATION: (1)..(57)

<400> SEQUENCE: 41
cacccagcga acactcatct tggaatctca gaattggcgc tatgctactg gaggatg          57

<210> SEQ ID NO 42
<211> LENGTH: 325
<212> TYPE: DNA
<213> ORGANISM: Cricetulus griseus
<220> FEATURE:
<221> NAME/KEY: gene
<222> LOCATION: (1)..(325)
<223> OTHER INFORMATION: FUT8 exon 7 genomic locus

<400> SEQUENCE: 42
gctgtctaca atggggagct cgaccacttg aacattttg tccttcactt cacctgacca        60
gtgtccagtg gagaggccag acctgtctgt gcatgtctca cttacaggtc taaacacagt     120
ctcccatcct ccagtagcat agcgccaatt ctgagattcc aagatgagtg ttcgctgggt     180
gccataagca atcatgaagc agtaaaccac atgatggagt tgacatccat agccacagcc     240
tttgttgata ttacatacca gctttctggc tttgctgcag tccttgggat tctgcagata     300
tgttattctc cgctggacca gctct                                           325

<210> SEQ ID NO 43
<211> LENGTH: 57
<212> TYPE: DNA
<213> ORGANISM: Cricetulus griseus
<220> FEATURE:
<221> NAME/KEY: Sequence in figure 3B containing CRISPR recognition seqs
      of the invention
<222> LOCATION: (1)..(57)

<400> SEQUENCE: 43
catcctccag tagcatagcg ccaattctga gattccaaga tgagtgttcg ctgggtg          57
```